United States Patent
Offerhaus et al.

(10) Patent No.: US 11,439,693 B2
(45) Date of Patent: Sep. 13, 2022

(54) VASOCONSTRICTIVE AND ANTIBACTERIAL COMBINATION TREATMENT FOR ROSACEA

(71) Applicant: Micreos Human Health B.V., The Hague (NL)

(72) Inventors: Mark Leonard Offerhaus, The Hague (NL); Bjorn Lars Herpers, Haarlem (NL)

(73) Assignee: MIGREOS HUMAN HEALTH B.V., Ev Den Haag (NL)

( * ) Notice: Subject to any disclaimer, the term of this patent is extended or adjusted under 35 U.S.C. 154(b) by 26 days.

(21) Appl. No.: 16/339,812

(22) PCT Filed: Oct. 5, 2017

(86) PCT No.: PCT/EP2017/075407
§ 371 (c)(1),
(2) Date: Apr. 5, 2019

(87) PCT Pub. No.: WO2018/065546
PCT Pub. Date: Apr. 12, 2018

(65) Prior Publication Data
US 2019/0307858 A1 Oct. 10, 2019

(30) Foreign Application Priority Data

Oct. 7, 2016 (WO) ................ PCT/EP2016/074036

(51) Int. Cl.
| | | |
|---|---|---|
| *A61K 38/47* | (2006.01) | |
| *A61K 31/498* | (2006.01) | |
| *A61K 45/06* | (2006.01) | |
| *A61K 31/4164* | (2006.01) | |
| *A61K 31/4174* | (2006.01) | |
| *A61K 38/48* | (2006.01) | |
| *A61P 31/04* | (2006.01) | |

(52) U.S. Cl.
CPC .......... *A61K 38/47* (2013.01); *A61K 31/4164* (2013.01); *A61K 31/4174* (2013.01); *A61K 31/498* (2013.01); *A61K 38/4886* (2013.01); *A61K 45/06* (2013.01); *A61P 31/04* (2018.01); *C12Y 302/01017* (2013.01); *C12Y 304/24075* (2013.01)

(58) Field of Classification Search
None
See application file for complete search history.

(56) References Cited

U.S. PATENT DOCUMENTS

| | | | |
|---|---|---|---|
| 2002/0187136 A1* | 12/2002 | Loomis ................ | A61K 38/46 424/94.1 |
| 2012/0082625 A1 | 4/2012 | Graeber et al. | |
| 2014/0343067 A1 | 11/2014 | Scherer et al. | |

FOREIGN PATENT DOCUMENTS

| | | | | |
|---|---|---|---|---|
| WO | 2015/005787 A1 | 1/2015 | | |
| WO | WO-2015005787 A1 * | 1/2015 | ........... | A61K 38/162 |

OTHER PUBLICATIONS

Moustafa, F.A. et al. 2014. Rosacea: new and emerging treatments. Drugs 74: 1457-1465. specif, pp. 1457, 1459, 1460.*
Vollmer, W. et al. 2008. Bacterial peptidoglycan (murein) hydrolases. FEMS Microbiological Reviews 32: 259-286; specif, pp. 259, 260.*
Wild, C.P. et al. 1996. Etiology of cancer in humans and animals. Experimental and Toxicologic Pathology 48: 95-100; specif, pp. 95, 96, 97.*
Anonymous: "DrugBank: Bacitracin (DB00626)", 2015, 4 pages, XP055256703, retrieved from the Internet: URL:http://web.archive.org/web/20151001171959/http://www.drugbank.ca/drugs/DB00626 [retrieved on Mar. 9, 2016].
Weinkle et al., "Update on the management of rosacea", Clinical, Cosmetic and Investigational Dermatology, 2015, vol. 8, 159-177.
Anonymous: "Staphefekt (TM) by Micreos", 2015, 2 pages, XP055256709, Retrieved from the Internet: URL:http://web.archive.org/web/20150528021547/https://www.staphefekt.com/en [retrieved on Mar. 9, 2016].
International Search Report for International Application No. PCT/EP2017/075407 dated Dec. 22, 2017, 5 pages.
Written Opinion for International Application No. PCT/EP2017/075407 dated Dec. 22, 2017, 8 pages.

* cited by examiner

*Primary Examiner* — Olivia M. Wise
*Assistant Examiner* — Sharon M. Papciak
(74) *Attorney, Agent, or Firm* — McDonnell Boehnen Hulbert and Berghoff LLP

(57) ABSTRACT

The invention relates to the field of medicine, specifically to the field of treatment of rosacea. The invention relates to a novel composition and a novel kit of parts, both comprising a vasoconstrictive compound and a compound specifically targeting a bacterial cell, preferably a gram positive bacterial cell. The invention further relates to said composition and/or kit of parts for medical use, preferably for treating an individual suffering from rosacea.

8 Claims, 1 Drawing Sheet

Specification includes a Sequence Listing.

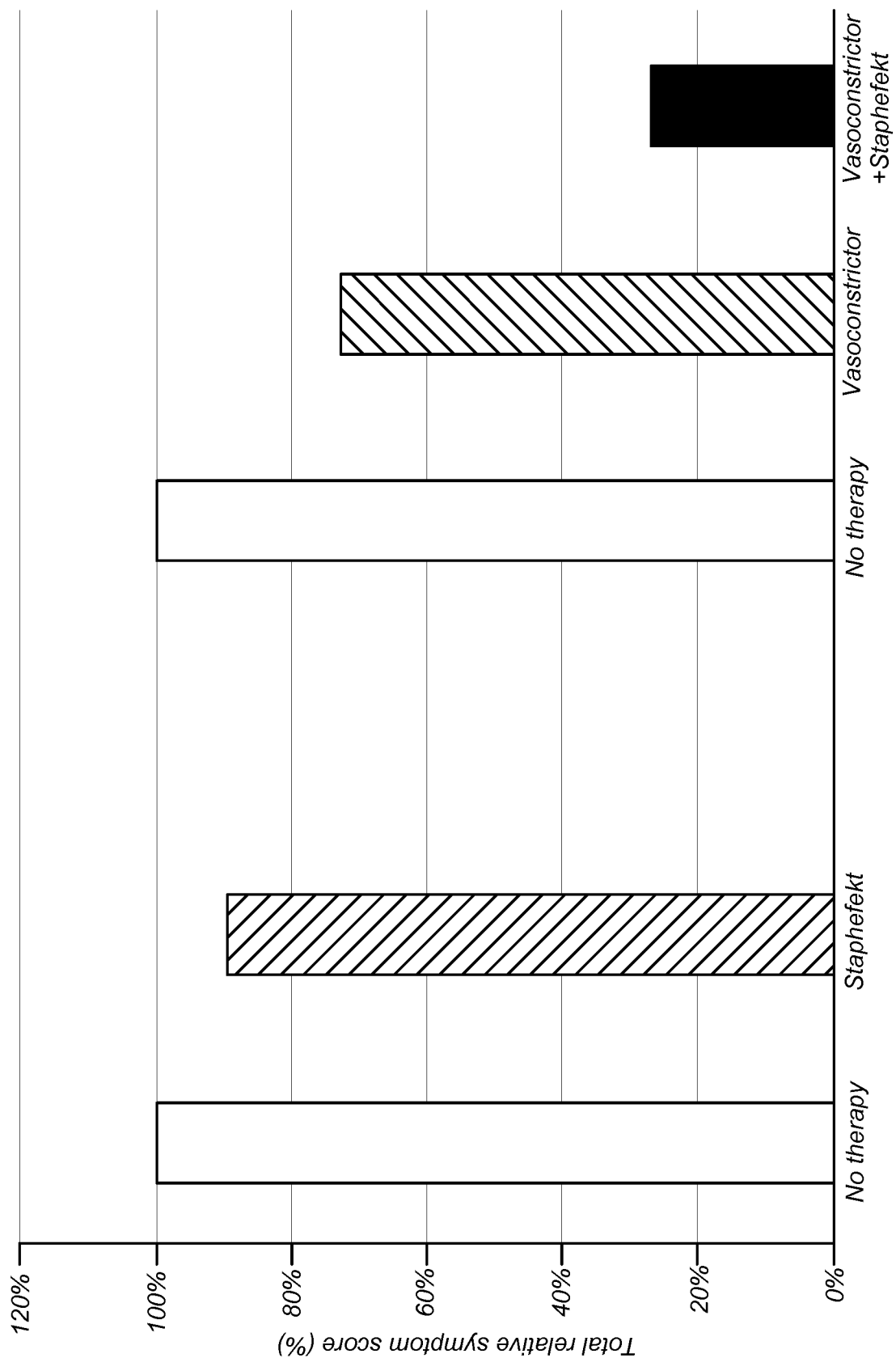

VASOCONSTRICTIVE AND ANTIBACTERIAL COMBINATION TREATMENT FOR ROSACEA

CROSS REFERENCE TO RELATED APPLICATIONS

The present application is a US national phase under 35 U.S.C. § 371 of international application PCT/EP2017/075407, filed Oct. 5, 2017, which claims priority to international application PCT/EP2016/074036, filed Oct. 7, 2016, which are incorporated herein by reference in their entirety.

FIELD OF THE INVENTION

The invention relates to the field of medicine, specifically to the field of treatment of rosacea. The invention relates to a novel composition and a novel kit of parts, both comprising a vasoconstrictive compound and a compound specifically targeting a bacterial cell, preferably a gram positive bacterial cell. The invention further relates to said composition and/or kit of parts for medical use, preferably for treating an individual suffering from rosacea.

BACKGROUND OF THE INVENTION

Rosacea is a chronic inflammatory condition of the facial skin affecting the blood vessels and pilosebaceous units. Rosacea is more common in persons of northern and western European descent with a fair complexion, but it can affect skin of any color. Although symptoms may wax and wane during the short term, rosacea can progress with time.

Patients usually have complaints of flushing, blushing, and sensitive skin. They may even be unaware of these symptoms prior to diagnosis, but a variety of triggers, or factors that induce or exacerbate rosacea, exist. Rosacea is manifested as erythematous flushing, blushing, telangiectasia, papules, and pustules affecting the central third of the face. In areas of long-standing disease, yellow-orange plaques (phymas) can develop, resulting from sebaceous hyperplasia, most commonly on the nose (rhinophyma). The red papules, pustules, and telangiectasia appear in the same distribution, albeit it with a lower frequency, in Asians and Hispanics; however, because of the pigmentation, they may not appear as erythematous. African-Americans generally do not have red papules and erythema; instead, they have the granulomatous form of rosacea. Many experts report that rosacea can occur in areas other than the face. In erythemato-telangiectatic rosacea (ETR), one may observe macular redness of the ears, the lateral facial contours, the neck, the upper portion of the chest, and the scalp. These extra facial manifestations in ETR are uncommon and are usually seen only in areas affected by flushing and by chronic sun damage. Acneiform lesions have been observed on the central part of the chest and on the scalp, the neck and, occasionally, the limbs.

Possible treatments of rosacea include azelaic acid, topical metronidazole, and oral tetracyclines, in particular minocycline and doxycycline. Other topical treatments include topical clindamycin, subantimicrobial-dose doxycycline and sulfur products. Azithromycin and controlled-release minocycline are other possible options for treating rosacea. For an extensive and comprehensive review on rosacea, see Culp and Scheinfeld, 2009; Pharmacy and Therapeutics, Vol 34 No. 1, page 38-45, which is herein incorporated by reference [8].

Rosacea is thus a complex inflammatory skin disorder and no precise treatment algorithm has become standard; treatment remains empirical. Treatment with e.g. topical and/or oral antibiotics is rather based on their symptomatic effect than on their antibacterial efficacy. Symptomatic treatment of erythematous flares, stinging and burning with the $alpha_1$-agonist oxymetazoline has been reported [9].

Accordingly, there is a need for improved treatment of rosacea extending mere symptomatic and empirical treatment.

FIGURE LEGENDS

FIG. 1. Total symptom scores of rosacea during monotherapy and combination therapy with a vasoconstrictor and Staphefekt™.

The symptom scores are expressed relative to the total score without therapy.

No therapy: White bars
Vasoconstrictor therapy: Shaded bar (left)
Staphefekt™ therapy: Shaded bar (right)
Combination therapy of vasoconstrictor and Staphefekt™: Black bar

DESCRIPTION OF THE INVENTION

An inappropriate innate immune response against environmental triggers is considered to play a major role in the pathogenesis of rosacea [1, 2]. Antigens of microbes are considered to act as an environmental trigger by stimulating Toll Like Receptor 2 (TLR 2) that is found to be over-present in the rosacea skin, resulting in inflammatory effects [3-5]. *Staphylococcus aureus* (*S. aureus*) is known for its ability to stimulate TLR 2 and its presence could thus attribute to inflammation in rosacea [2, 6, 7].

The inventors have established that a combination of an antibacterial agent and a vasoconstrictor results in effective treatment of rosacea, telangiectasia, erythema and/or flushing. Without being bound to theory, it is believed that the bacterial trigger for inflammation is suppressed by the antibacterial agent, resulting in less inflammation-related vasodilatation, in turn allowing a lower need for a vasoconstrictive compound. The combined effect of said combination of compound has a surprising synergistic effect. Accordingly, in a first aspect, the invention provides for a novel composition comprising a first and a second compound, wherein said first compound is a vasoconstrictor and said second compound is a compound specifically targeting a bacterial cell, preferably a gram positive bacterial cell. Preferably, said gram positive bacterial cell is a *Staphylococcus*, more preferably a *Staphylococcus aureus*. Preferably, said composition is a medicament preferably for use in the treatment of rosacea, more preferably for use in the treatment of telangiectasia, erythema and/or flushing, preferably telangiectasia, erythema and/or flushing associated with inflammation induced vasodilatation, as further detailed herein. The invention provides for a novel composition comprising both a vasoconstrictive compound and a compound specifically targeting a bacterial cell, preferably a gram positive bacterial cell, preferably a *Staphylococcus aureus*, which combats most, if not all, of the disadvantages of using either an effective dosage regime of a vasoconstrictive compound and/or a conventional topical or oral agent alone or in combination and provides a unexpected synergy. In comparison to the use of vasoconstrictive compound alone, a combination according to the invention decreases the risk and/or is more effective in treating rosacea, more preferably telangiectasia, erythema and/or flushing, preferably telangiectasia, erythema and/or flushing associated with inflammation induced vasodilatation. Furthermore, in comparison to the use of a vasoconstrictor alone, a composition according to the invention may be as effective as using a vasoconstrictor alone while making use of a substantially lower dosage and/or a shorter administration regimen resulting in a shorter exposure time of the vasoconstrictor thereby reducing possible side-effects.

In comparison to the use of a vasoconstrictor in combination with conventional antibiotics and/or conventional antibiotics alone, the composition of the invention selectively targets a bacterial cell, preferably a gram positive bacterial cell, preferably a *Staphylococcus*, more preferably a *Staphylococcus aureus*, without affecting surrounding commensal and/or beneficial microflora. In addition, the risk of developing resistance against antibiotics is diminished or at least reduced since lower amounts of antibiotics or even no antibiotics at all are used.

An agent that specifically targets a gram positive bacterial cell preferably is an agent that shows at least 2, 5, 10, 50 or 100 times higher lytic activity towards a gram positive bacterial cell as compared to a gram negative bacterial cell. Preferably, an agent that specifically targets a gram positive bacterial cell is an agent that does not affect a gram negative bacterial cell in a concentration that is affective in lysing a gram positive bacterial cell. An agent that specifically targets a *Staphylococcus* bacterial cell preferably is an agent that shows at least 2, 5, 10, 50 or 100 times higher lytic activity towards a *Staphylococcus* bacterial cell as compared to a non-*Staphylococcus* bacterial cell. Preferably, an agent that specifically targets a *Staphylococcus* bacterial cell is an agent that does not affect a non-*Staphylococcus* bacterial cell in a concentration that is effective in lysing a *Staphylococcus* bacterial cell. An agent that specifically targets a *Staphylococcus aureus* bacterial cell preferably is an agent that shows at least 2, 5, 10, 50 or 100 times higher lytic activity towards a *Staphylococcus aureus* bacterial cell as compared to a non-*Staphylococcus aureus* bacterial cell. Preferably, an agent that specifically targets a *Staphylococcus aureus* bacterial cell is an agent that does not affect a non-*Staphylococcus aureus* bacterial cell in a concentration that is effective in lysing a *Staphylococcus aureus* bacterial cell. Lytic activity is preferably assessed by a turbidity assay as described elsewhere herein.

Preferably, the invention provides a composition comprising a first and a second compound, wherein said first compound is an a vasoconstrictive compound and said second compound is a compound specifically targeting a bacterial cell, preferably a gram positive bacterial cell, and wherein said second compound comprises at least one cell wall binding domain specifically binding the peptidoglycan cell wall of said bacterial cell, preferably gram positive bacterial cell. A cell wall-binding domain of the invention is defined as an element, preferably a polypeptide within said second compound that directs said second compound to the bacterial wall of a bacterial cell.

A cell wall-binding domain encompassed within the invention may be any cell wall-binding domain known by the person skilled in the art. Preferably, a cell wall-binding domain of the invention is an element, preferably a polypeptide within said second compound, that directs said second compound to the peptidoglycan cell wall of a gram-positive bacterial cell, preferably the peptidoglycan cell wall of a *Staphylococcus* bacterial cell, more preferably the peptidoglycan cell wall of a *Staphylococcus aureus* bacterial cell.

Preferably, the invention provides a composition comprising a first and a second compound, wherein said first compound is a vasoconstrictive compound and said second compound is a compound specifically targeting a bacterial cell, preferably a gram positive bacterial cell, and wherein said second compound comprises at least one cell wall binding domain specifically binding the peptidoglycan cell wall of *Staphylococcus*, more preferably, a *Staphylococcus aureus*.

Binding of a domain to the peptidoglycan cell wall of *Staphylococcus* genera may be assessed using assays well known to the person skilled in the art. In a preferred embodiment, an immunohistochemical technique and/or a gene fusion technique resulting in labelled constructs are used for assessing specific binding of compounds such as peptides, polypeptides, proteins or bacteriophages to the peptidoglycan cell wall of *Staphylococcus* genera. Quantification methods of signals used in the above mentioned immunohistochemical or fusion techniques are well known in the art.

In one embodiment, *Staphylococcus* peptidoglycan cell wall-binding is quantified using a fluorescent fusion construct comprising a cell wall-domain of interest. Such a cell wall-binding assay is described in detail by Loessner et al (Molecular Microbiology 2002, 44(2): 335-349). In this assay a solution comprising said fluorescent fusion construct or a negative control, preferably Green Fluorescent Protein (GFP), is subjected to *Staphylococcus* cells, preferably *S. aureus* cells, more preferably *S. aureus* BB255 for an indicated time period where after the cells are sedimented by centrifugation together with the bound fluorescent fusion constructs. The fluorescent signal of the *Staphylococcus* cells exposed to a fluorescent fusion construct subtracted by the fluorescence signal of the *Staphylococcus* cells exposed to a negative control, preferably GFP, is a measure for cell binding as meant in this disclosure. Preferably, within the context of the invention, a domain is said to bind the peptidoglycan cell wall of *Staphylococcus* genera when using this assay an increase in fluorescent signal of the sedimented cells above the negative control as defined herein is detected. Preferably, the invention relates to a cell wall-binding domain which exhibits binding as defined herein of at least 50, 60, 70, 80, 90 or 100, 150 or 200% of peptidoglycan cell wall-binding of *S. aureus* bacteriophage (I2638a endolysin (Ply2638 endolysin defined by SEQ ID NO: 2) preferably encoded by SEQ ID NO: 1. Preferably, a fusion construct as represented by SEQ ID NO: 95 and encoded by SEQ ID NO: 96 serves as a positive control in this assay. An overview of all sequences included and their SEQ ID NO is given in table 1.

Preferably, the invention provides for a composition comprising a first and a second compound, wherein said first compound is a vasoconstrictive compound and said second compound is a compound specifically targeting a bacterial cell, preferably a gram positive bacterial cell, and wherein said second compound comprises at least one cell wall binding domain that originates from or is a homologue of a *Staphylococcus* phage endolysin, preferably said *Staphylococcus* phage endolysin is selected from, but not limited to, *S. aureus* bacteriophage Φ2638a endolysin, *S. aureus* bacteriophage Φ11 endolysin, *S. aureus* bacteriophage ΦTwort endolysin, *S. haemolyticus* JCSC1435, *S. aureus* Phage K endolysin, *S. warneri* phage WMY endolysin, *S. aureus* phage NM3 endolysin and *S. aureus* 80alpha endolysin.

Also preferred is a cell wall binding domain originating from or a homologue of *S. simulans* lysostaphin (represented by SEQ ID NO: 76, preferably encoded by SEQ ID NO: 75).

A known homologue of *S. simulans* lysostaphin having cell wall binding properties is *S. capitis* ALE-1 enzyme.

Preferably, said cell wall binding domain has at least 80% identity to any of SEQ ID NO: 4, 6 or 8 and/or wherein said one or more enzymatic active domains has at least 80% identity to any of SEQ ID NO: 10, 12, 14, 16, 18, 98 or 100. A preferred cell wall-binding domain of the invention is a cell wall-binding domain having at least 80, 81, 82, 83, 84, 85, 86, 87, 88, 89, 90, 91, 92, 93, 94, 95, 96, 97, 98, 99 or 100% identity with the cell wall binding domain of *S. simulans* lysostaphin defined herein by SEQ ID NO: 4 and preferably encoded by SEQ ID NO: 3. Also preferred is a cell wall-binding domain isolated from a native *Staphylococcus* bacteriophage endolysin. Also preferred is a cell wall-binding domain of the invention that has at least 80, 81, 82, 83, 84, 85, 86, 87, 88, 89, 90, 91, 92, 93, 94, 95, 96, 97, 98, 99 or 100% identity with the cell wall-binding domain of *S. aureus* bacteriophage Φ2638a endolysin defined herein by SEQ ID NO: 6 and preferably encoded by SEQ ID NO: 5. Also preferred is a cell wall-binding domain isolated from a native *Staphylococcus aureus* phage phiNM3 endolysin. Preferably, a cell wall-binding domain of the invention has at least 80, 81, 82, 83, 84, 85, 86, 87, 88, 89, 90, 91, 92, 93, 94, 95, 96, 97, 98, 99 or 100% identity with the cell wall-binding domain of *S. aureus* phage phiNM3 endolysin defined herein by SEQ ID NO: 8 and preferably encoded by SEQ ID NO: 7.

Preferably, the invention provides for a composition comprising a first and a second compound, wherein said first compound is a vasoconstrictive compound and said second compound is a compound specifically targeting a bacterial cell, preferably a gram positive bacterial cell, wherein said second compound comprises one or more enzymatic active domains exhibiting target bond specificity. 'An enzymatic active domain' is defined herein is a domain having lytic activity, preferably exhibiting peptidoglycan hydrolase activity. Lytic activity can be assessed by methods well known by the person skilled in the art. In an embodiment, lytic activity is assessed spectrophotometrically by measuring the drop in turbidity of substrate cell suspensions. Turbidity is assessed by measuring optical density at a wavelength of 595 nm, typically a culture as turbid when it exhibits an optical density of at least 0.3 OD at a wavelength of 595 nm. Preferably, lytic activity is assessed spectrophotometrically measuring the drop in turbidity of a *S. aureus* suspension, wherein turbidity is quantified by measuring $OD_{595}$ spectrophotometrically (Libra S22, Biochrom). More preferably, 200 nM polypeptide comprising an enzymatic active domain of the invention as identified herein is incubated together with an *S. aureus* suspension having an initial $OD_{595}$ of 1±0.05, as assessed spectrophotometrically (Libra S22, Biochrom), in PBS buffer pH 7.4, 120 mM sodium chloride for 30 min at 37° C. The drop in turbidity is calculated by subtracting the $OD_{595}$ after 30 min of incubation from the $OD_{595}$ before 30 min of incubation. Within the context of the invention a polypeptide comprising an enzymatic active domain of the invention as identified herein will be said to have lytic activity if, when using this assay, a drop in turbidity of at least 10, 20, 30, 40, 50 or 60% is detected. Preferably, a drop in turbidity of at least 70% is detected. Preferably, a polypeptide comprising an enzymatic active domain of the invention exhibits a lytic activity of at least 30, 40, 50, 60, 70, 80, 90, 100, 150 or 200% or more of a lytic activity of *S. aureus* bacteriophage (I2638a endolysin (Ply2638 endolysin identified by SEQ ID NO: 2) preferably encoded by SEQ ID NO: 1. Preferably, the invention provides for a composition comprising a first and a second compound, wherein said first compound is a vasoconstrictive compound and said second compound is a compound specifically targeting a bacterial cell, preferably a gram positive bacterial cell, wherein said second compound comprises one or more enzymatic active domains exhibiting target bond specificity, and wherein said target bond is an essential bond in a peptidoglycan layer of said bacterial cell, preferably gram positive bacterial cell. An essential bond in a peptidoglycan layer of a bacterial cell, preferably a gram-positive bacterial cell is defined herein as a linkage within said peptidoglycan that is essential for said peptidoglycan to provide said bacterial cell shape and a rigid structure resistance to osmotic shock. Preferably, said essential bond in a peptidoglycan layer of a gram-positive bacterial cell is a bond between a D-alanine of the stem peptide and a glycine of the cross-bridge peptide (defined herein also as a bond between an N-terminal alanine and a glycine), a bond in a pentaglycin cross-bridge (defined herein also as a pentaglycin bridge glycyl-glycyl bond, a bond between an N-acetylmuramoyl and an L-alanine or a bond between an N-acetylmuramine and a N-acetylglucosamine or between a N-acetylglucosamine and an N-acetylmuramine. Other preferred essential bonds in a peptidoglycan layer of a gram-positive bacterial cell are a bond in a gamma-glutamyl stem peptide, a bond between an L-alanyl-iso-D-glutamic acid in a stem peptide and a bond between an iso-D-glutamic acid-L-Lysine in a stem peptide.

Most native *Staphylococcus* bacteriophage endolysins exhibiting peptidoglycan hydrolase activity consist of a C-terminal cell wall-binding domain (CBD), a central N-acetylmuramoyl-L-Alanine amidase domain, and an N-terminal alanyl-glycyl endopeptidase domain with cysteine, histidine-dependent amidohydrolases/peptidase (CHAP) homology, or in case of Ply2638, of an N-terminal glycyl-glycine endopeptidase domain with Peptidase_M23 homology, the latter three domains exhibiting peptidoglycan hydrolase activity each with distinct target bond specificity and generally named herein as enzymatically active domains. Preferably, said one or more enzymatic active domains is/are selected from or is/are a permutation of a domain of the group consisting of a cysteine, histidine dependent amidohydrolases/peptidase domain, an endopeptidase domain, an amidase domain and a glycosylhydrolase domain. Said glycosylhydrolase domain can be a muramidase domain or a glycosaminidase domain. Preferably, said CHAP domain cleaves a bond between an N-terminal alanyl and a glycyl within a peptidoglycan layer. More preferably, said CHAP domain specifically cleaves a bond between an N-terminal alanyl and a glycyl within a peptidoglycan layer. Preferably, said endopeptidase domain cleaves pentaglycin bridge glycyl-glycyl bond within a peptidoglycan layer. More preferably, said endopeptidase domain specifically cleaves pentaglycin bridge glycyl-glycyl bond within a peptidoglycan layer. Preferably, said amidase domain cleaves a bond between a central N-acetlymuramoyl and an L-Alanine within a peptidoglycan layer. More preferably, said amidase domain specifically cleaves a bond between a central N-acetlymuramoyl and an L-Alanine within a peptidoglycan layer. Preferably, said murimidase domain cleaves a bond between an N-acetylmuramine and a N-acetylglucosamine within a peptidoglycan layer. More preferably, said murimidase domain specifically cleaves a bond between an N-acetylmuramine and a N-acetylglucosamine within a peptidoglycan layer. Preferably, said glucosaminidase domain cleaves a bond between an N-acetlyglucosamine and an N-acetylmuramine within a peptidoglycan layer. More preferably, said glucosaminidase domain specifically cleaves a bond between an N-acetlyglucosamine and an N-acetylmuramine within a peptidoglycan layer. Preferably said peptidoglycan layer is of a bacterial cell, preferably a gram positive bacterial cell, more preferably of a *Staphylococcus*, most preferably of a *Staphylococcus Aureus*. Preferably, the cleavage of a bond by an enzymatic active domain as defined herein is specific if such a bond is hydrolyzed at least 2, 5, 10, 50 or a 100 times more efficient with said enzymatic active domain as compared to the hydrolyses of any other bond as defined herein above with said enzymatic active domain.

Preferably, a CHAP domain encompassed within the invention originates from *Staphylococcus* phage K, *Staphylococcus* phage Twort and/or *S. aureus* bacteriophage phi 11. Preferably, a CHAP domain encompassed within the invention, is a domain that has at least 80, 81, 82, 83, 84, 85, 86, 87, 88, 89, 90, 91, 92, 93, 94, 95, 96, 97, 98, 99 or 100% identity with SEQ ID NO: 10, 12 or 98 and/or is preferably encoded by SEQ ID NO: 9 or 11. Preferably, an endopeptidase domain encompassed within the invention originates from *S. aureus* bacteriophage (2638a and/or *S. simulans*. Preferably, an endopeptidase domain encompassed by the invention has at least 80, 81, 82, 83, 84, 85, 86, 87, 88, 89, 90, 91, 92, 93, 94, 95, 96, 97, 98, 99 or 100% identity with SEQ ID NO: 14 or 16 and/or is preferably encoded by SEQ ID NO: 13 or 15. Preferably, an amidase domain encompassed within the invention originates from *S. aureus* bacteriophage (2638a or *S. aureus* bacteriophage phi 11. Preferably an amidase domain of the invention has at least 80, 81, 82, 83, 84, 85, 86, 87, 88, 89, 90, 91, 92, 93, 94, 95, 96, 97, 98, 99 or 100% identity with SEQ ID NO: 18 or 100 and/or is preferably encoded by SEQ ID NO: 17 or 99.

Preferably, the invention provides for a composition comprising a first and a second compound, wherein said first compound is an a vasoconstrictive compound and said second compound is a compound specifically targeting a bacterial cell, preferably a gram positive bacterial cell, wherein said second compound is a naturally occurring or mutant bacteriophage, a naturally occurring endolysin or a mutant polypeptide.

A naturally occurring bacteriophage of the invention may be any bacteriophage specifically targeting and infecting a bacterial cell, preferably bacterial cell, preferably a *Staphylococcus*, most preferably a *Staphylococcus aureus*. Preferably, a naturally occurring bacteriophage of the invention is selected from, but not limited to, a group consisting of *S. aureus* bacteriophage Φ2638a, *S. aureus* bacteriophage Φ11, *S. aureus* bacteriophage ΦTwort, *S. haemolyticus* JCSC1435, *S. aureus* Phage K, *S. warneri* phage WMY, *S. aureus* phage NM3 and *S. aureus* 80alpha. Said naturally occurring endolysin may be synthesized and/or purified. A bacteriophage according to the invention may be a mutant, chimeric and/or recombinant bacteriophage. The person skilled in the art may construct a bacteriophage of the invention by placing mutations in the genome and/or deleting and/or inserting coding sequences or parts thereof into the genome using methods known in the art.

A naturally occurring endolysin may be any wild type or native endolysin exhibiting peptidoglycan hydrolase activity. Preferred is a *Staphylococcus* phage endolysin, preferably said *Staphylococcus* phage endolysin is selected from, but not limited to, the group consisting of *S. aureus* bacteriophage Φ2638a endolysin, *S. aureus* bacteriophage Φ11 endolysin, *S. aureus* bacteriophage ΦTwort endolysin, *S. haemolyticus* JCSC1435, *S. aureus* Phage K endolysin, *S. warneri* phage WMY endolysin, *S. aureus* phage NM3 endolysin and *S. aureus* 80alpha endolysin. Also preferred is *S. simulans* lysostaphin and/or a homologue of *S. simulans* lysostaphin such as *S. capitis* ALE-1 enzyme. Most native *Staphylococcus* bacteriophage endolysins exhibiting peptidoglycan hydrolase activity consist of a C-terminal cell wall-binding domain (CBD), a central N-acetylmuramoyl-L-Alanine amidase domain, and an N-terminal Alanyl-glycyl endopeptidase domain with CHAP homology, or in case of Ply2638, of an N-terminal endopeptidase domain with Peptidase_M23 homology, the latter three domains exhibiting peptidoglycan hydrolase activity each with distinct target bond specificity and generally named herein as enzymatically active domains.

A mutant polypeptide as encompassed within the invention may be a chemically synthesized polypeptide or a recombinant or retrofitted polypeptide produced in vitro. A retrofitted construct is defined herein as a polynucleotide comprising heterologous nucleotide sequences. As used herein the term heterologous sequence or heterologous polynucleotide is one that is not naturally found operably linked as neighboring sequence of said first nucleotide sequence. As used herein, the term heterologous may mean recombinant. Recombinant refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature. Preferably, a mutant polypeptide to the invention comprises at least an enzymatic active domain and a cell binding domain as defined herein.

An endolysin or mutant polypeptide of the invention may be in a purified form or may be comprised within a crude composition, preferably of biological origin, such as a bacterial lysate, yeast lysate, fungal lysate, sonicate or fixate. Alternatively, said endolysin or mutant polypeptide may be a chemically synthesized endolysin or polypeptide or a recombinant polypeptide produced in vitro.

An endolysin or mutant polypeptide of the invention preferably comprises or consists of at least one enzymatic active domain and at least one cell binding domain and optionally a tag for ease of purification. Preferably, said tag is selected from, but is not limited to, the group consisting of a FLAG-tag, poly(His)-tag, HA-tag and Myc-tag. More preferably said tag is a 6×His-tag. Even more preferably, said tag is an N-terminal 6×His-tag (indicated herein as HXa) identical to SEQ ID NO: 74 and preferably encoded by SEQ ID NO: 73).

Preferably, a cell wall-binding domain according to the invention is located on the C-terminal side of the enzymatic active domain within said naturally occurring endolysin or a mutant polypeptide. Preferably, said mutant naturally occurring or mutant polypeptide comprises at least two or more enzymatic active domains with distinct target bond specificities as distinct target bond specificities confer synergistic effects. In an embodiment of the invention, a composition comprises at least two distinct compounds targeting a bacterial cell, preferably a gram positive bacterial cell, preferably a *Staphylococcus*, more preferably a *Staphylococcus aureus*. Preferably said at least two distinct compounds are naturally occurring endolysin, which are optionally synthesized. Preferably said at least two distinct compounds are recombinant polypeptides each comprising a distinct enzymatic active domain and/or a different multiplicity of at least two distinct enzymatic active domains as defined herein below.

Preferably, the invention provides for a composition comprising a first and a second compound, wherein said first compound is a vasoconstrictive compound and said second compound is a compound specifically targeting a bacterial cell, preferably a gram positive bacterial cell, wherein said second compound is a recombinant polypeptide comprising a multiplicity of said one or more enzymatic active domains exhibiting target bond specificity. "Multiplicity" is to be understood as a number of copies and may be any integer varying from 1 to 20, preferably from 1 to 10, more preferably from 1 to 3, most preferably said multiplicity is 2, i.e. a duplicate. Polypeptides comprising a multiplicity of enzymatic active domains show superior lytic activity as compared to polypeptides comprising a single enzymatic active domain.

Preferably, said second compound is a polypeptide comprising and/or consisting of an enzymatic active domain, a cell wall binding and optionally a tag for ease of purification as defined herein, preferably said enzymatic active domain being a cysteine, histidine-dependent amidohydrolases/peptidase domain, an endopeptidase domain or an amidase domain, and preferably polypeptide comprises a multiplicity of said enzymatic active domain, preferably said multiplicity being 2, i.e. a duplicate. More preferably said polypeptide comprises and/or consists of a duplicated amidase domain and a cell wall binding domain and optionally a tag for ease of purification as defined herein, preferably said amidase is from S. aureus bacteriophage (I2638a endolysin and said cell wall binding domain is of S. simulans lysostaphin. Most preferably said polypeptide comprises and/or consists of a duplicated endopeptidase domain and a cell wall binding domain and optionally a tag for ease of purification as defined herein, preferably said endopeptidase domain is a Peptidase_M23 domain of S. simulans lysostaphin and said cell wall binding domain is of S. simulans lysostaphin.

Preferably, said second compound is a polypeptide has at least 80, 81, 82, 83, 84, 85, 86, 87, 88, 89, 90, 91, 92, 93, 94, 95, 96, 97, 98, 99 or 100% identity with SEQ ID NO: SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 76, 78, 80, 82, 84, 86, 88, 90, 92, 94, 98, 100 and 101 and/or is encoded by a polynucleotide having at least 80, 81, 82, 83, 84, 85, 86, 87, 88, 89, 90, 91, 92, 93, 94, 95, 96, 97, 98, 99 or 100% identity to any of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 75, 77, 79, 81, 83, 85, 87, 89, 91, 93, 97 or 99. Preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 28, 34, 46, 52, 58, 70, 84 or 101; more preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 28, 46, 52, 70, 84 or 101; even more preferably, said polypeptide has at least 80, 81, 82, 83, 84, 85, 86, 87, 88, 89, 90, 91, 92, 93, 94, 95, 96, 97, 98, 99 or 100% identity with SEQ ID NO: 46, 70, 84 or 101; most preferably said polypeptide has at least 80, 81, 82, 83, 84, 85, 86, 87, 88, 89, 90, 91, 92, 93, 94, 95, 96, 97, 98, 99 or 100% identity with SEQ ID NO: 70 or 101.

In all embodiments of the invention, the second compound according to the invention may be an endolysin polypeptide that comprises a protein transduction domain enabling the endolysin polypeptide to enter a cell that harbors an intracellular bacterium. Protein transduction domains are extensively described in EP158880.3 and these are preferred protein transduction domains. When the second compound according to the invention is an endolysin polypeptide comprising a protein transduction domain enabling the endolysin polypeptide to enter a cell that harbors an intracellular bacterium, treatment preferably comprises administration of an effective amount of an agent that increases the intracellular pH of a host cell and/or of an intracellular compartment of a host cell, wherein the increase in pH activates a non-replicating intracellular bacterium and the endolysin kills the activated intracellular bacterium. Such treatment is extensively described in EP15158880.3, which is herein incorporated by reference.

All embodiments of the invention relating to preventing, delaying and/or curing of telangiectasia, erythema and/or flushing, preferably telangiectasia, erythema and/or flushing associated with inflammation induced vasodilatation, can be combined with the combination treatment for topical dermatitis as described in WO2015/005787, which is herein incorporated by reference. WO2015/005787 describes preventing, delaying and/or curing of atopic dermatitis, preferably eczema using a composition comprising a first and a second compound, wherein said first compound is an anti-inflammatory compound and said second compound is a compound specifically targeting a bacterial cell, preferably a gram positive bacterial cell. The second compound may be a second compound according to the invention.

Preferably, the invention provides for a composition comprising a first and a second compound, wherein said first compound is a vasoconstrictive compound and said second compound is a compound specifically targeting a bacterial cell, preferably a gram positive bacterial cell, wherein said first compound is a sympathomimetic compound. A sympathomimetic compound (also referred to as sympathomimetic drug) is a stimulant compound which mimics the effects of an agonist of the sympathetic nervous system such as a catecholamine. (epinephrine (adrenaline), norepinephrine (noradrenaline), dopamine, etc.). The mechanism of a sympathomimetic drug can be direct-acting, such as an α-adrenergic agonist, β-adrenergic agonist, and a dopaminergic agonist; or indirect-acting, such as an MAOI (Mono-AmineOxidase Inhibitor), a COMT (Catechol-O-Methyl Transferase) inhibitor, a release stimulant, and a reuptake inhibitor that increases the level of an endogenous catecholamine.

The first compound preferably is a sympathomimetic compound selected from the group consisting of alpha(1)- and alpha(2)-adrenergic receptor-mediated vasoconstrictive compounds, such as Brimonidine, Tetrahydrozoline and Oxymetazoline; 25I-NBOMe; Amphetamines; 5-methoxy-α-methyltryptamine 5-MeO-AMT (5-methoxy-α-methyltryptamine); Antihistamines; Caffeine; Cocaine; DOM (2,5-dimethoxy-4-methylamphetamine); LSA (Lysergic acid amide); Methylphenidate; Mephedrone; Phenylephrine; Propylhexedrine; Pseudoephedrine; Psycho stimulants; Benzylpiperazine; Cathine; Cathinon; Ephedrine; Lisdexamfetatime; maprotiline; Methamphetamine; methcathinone; methylenedioxypyrovalerone; methylphenidate (Ritalin); 4-methylaminorex; Pemoline; Phenmetrazine; and Propylhexedrine; or a combination of two or more of these. A more preferred first compound is a vasoconstrictive compound selected from the group consisting of alpha(1)- and alpha(2)-adrenergic agonists such as Brimonidine, Tetrahydrozoline and Oxymetazoline. A most preferred first compound is a vasoconstrictive compound selected from the group consisting of Brimonidine, Tetrahydrozoline and Oxymetazoline. The compounds listed here above are herein referred to as a vasoconstrictive compound according to the invention or a sympathomimetic compound according to the invention and are applicable to all embodiments of the invention.

In all embodiments of the invention, the second compound specifically targeting a bacterial cell, preferably a gram positive bacterial cell may be comprised of a combination of a source of a first enzymatic active domain and a source of a second enzymatic active domain, wherein said first and second enzymatic active domains exhibit distinct target bond specificities and are comprised on a distinct first and second polypeptide, i.e. said first enzymatic active domain is comprised on a first polypeptide and said second enzymatic domain is comprised on a second polypeptide, wherein said first and second polypeptide each have a distinct amino acid sequence. In addition, the second compound according to the invention may be comprised of a combination of a source of a first enzymatic active domain, a source of a second enzymatic active domain and a source of a third enzymatic active domain, wherein said first, second and third enzymatic active domain exhibit distinct target bond specificities and are comprised on a distinct first, second and third polypeptide, i.e. said first enzymatic active domain is comprised on a first polypeptide, said second enzymatic domain is comprised on a second polypeptide, and said third enzymatic domain is comprised on a third polypeptide, wherein said first, second and third polypeptide each have a distinct amino acid sequence. Furthermore, the second compound according to the invention may be comprised of a combination of a source of a first enzymatic active domain, a source of a second enzymatic active domain, a source of a third enzymatic active domain, and a source of a further enzymatic active domain, wherein said first, second, third and further enzymatic active domain exhibit distinct target bond specificities and are comprised on a distinct first, second, third and further polypeptide, i.e. said first enzymatic active domain is comprised on a first polypeptide, said second enzymatic domain is comprised on a second polypeptide, said third enzymatic domain is comprised on a third polypeptide, and said further enzymatic active domain is comprised on a further polypeptide, wherein said first, second, third and further polypeptide each have a distinct amino acid sequence. A further enzymatic active domain is meant herein as a fourth, fifth, sixth, seventh, eighth, ninth, tenth or more enzymatic active domain, preferably a fourth enzymatic active domain. A further polypeptide is meant herein as a fourth, fifth, sixth, seventh, eighth, ninth, tenth or more polypeptide, preferably a fourth polypeptide.

The inventors surprisingly found for the second compound according to the invention, that simultaneous application of two or more enzymatically active domains with distinct target bond specificities confers synergistic effects. Surprisingly, this works not only when enzymatically active domains with different specificities are located on the same molecule as in native *Staphylococcus* endolysins, but works also when the enzymatically active domains with different specificities are separated on distinct polypeptides. The benefit of having distinct enzymatic active domains located on separate individual polypeptides is that the resulting polypeptides are smaller which can be more easily produced. Furthermore, these smaller polypeptides have better diffusion properties in specific environments and can be more resistant to degradation and feature higher thermostability. Another advantage is that independent distinct enzymatic active domains located on separate distinct polypeptide molecules can be mixed and pooled in variable compositions, at a ratio that is best suited to hydrolyse the specific bacterial target cells. The second compound according to the invention comprised of a combination as described herein can be supplemented and/or complemented by the use of virtually any functional enzymatic active domain with virtually any target bond specificity from many different origins including phage lysins, bacteriocins, autolysins, or any other cell wall lytic enzymes.

Within the context of the second compound according to the invention 'a combination' means that a source of a first enzymatic active domain and a source of a second enzymatic active domain are contemplated and encompassed. In addition, within the context of the second compound according to invention 'a combination' means that a source of a first enzymatic active domain, a source of a second enzymatic active domain and optionally a source of a third and/or further enzymatic active domain are contemplated and encompassed. Each source may be together or present together or combined together or physically in contact with the other source forming one single composition. Each source may alternatively be comprised within a distinct composition. However the invention provides the insight that both sources of a first and a second enzymatic active domain are preferably needed or are used in order to get an effect of the invention as defined herein.

If each source is not present in a same single composition, each source and/or each distinct composition comprising a source of a combination encompassing the second compound according to the invention may be used sequentially or simultaneously. 'A source of a first enzymatic active domain', 'a source of a second enzymatic active domain', 'a source of a third enzymatic active domain' and 'a source of a further enzymatic active domain' preferably comprises a protein-based source, i.e. a polypeptide, a protein, digest of a protein and/or fragment of a protein or digest, or a source not being protein based, i.e. a nucleic acid encoding a protein or derived peptide or protein fragment. Below we define preferred sources of a first enzymatic active domain, a source of a second enzymatic active domain, a source of a third enzymatic active domain and a source of a further enzymatic active domain that are encompassed by the invention. When the second compound according to the invention relates to a combination of a source of a first enzymatic active domain, a source of a second enzymatic active domain and optionally a source of a third and/or further enzymatic active domain, each of the sources of a first enzymatic active domain defined herein may be combined with each of the sources of a second and optionally third and/or further enzymatic active domain defined herein. It is also encompassed by the invention to use a combination of a source of a first enzymatic active domain being protein-based with a source of a second and optionally a third and/or further enzymatic active domain being not protein-based, and vice versa.

'Comprised on distinct polypeptides' is meant herein as any of said first, second and optionally third and/or further enzymatic active domain is comprised on a polypeptide which is distinct from the polypeptide that any of the other of said first, second and optionally third and/or further enzymatic active domain is comprised on.

In all embodiments according to the invention, a polypeptide can be a natural polypeptide or an isolated polypeptide, preferably an isolated polypeptide. A nucleic acid according to the invention may be a natural nucleic acid or an isolated nucleic acid, preferably an isolated nucleic acid. A nucleic acid construct according to the invention can be a natural or an isolated construct, preferably an isolated nucleic acid construct.

Preferably, a first, a second and optionally a third and/or further enzymatic active domain together encompassing the second compound according to the invention is a domain selected from the group consisting of a cysteine, histidine-dependent amidohydrolases/peptidase (CHAP) domain, an endopeptidase domain, and an amidase domain; all preferably as described previously herein.

Preferably, a first, second, third and/or further polypeptide together encompassing the second compound according to the invention comprises a different multiplicity of a first, second, third and/or further enzymatic active domain according to the invention. A "multiplicity" is herein defined as a number of copies. A "different multiplicity" is defined herein as a multiplicity or number of copies of a specific enzymatic active domain according to the invention, i.e. a first, second, third or further enzymatic active domain as defined herein, comprised within a specific polypeptide of the invention, i.e. a first, second, third or further polypeptide as defined herein, to be different form a multiplicity or number of copies of that same enzymatic active domain within another polypeptide of the combination encompassing the second compound of the invention. For example, a combination encompassing the second compound of the invention comprises a first polypeptide comprising a specific number of copies of a first enzymatic active domain, and a second polypeptide comprising a different number of copies of said first enzymatic active domain. Furthermore, said first polypeptide of said exemplified combination encompassing the second compound of the invention may further comprise a specific number of copies of second enzymatic active domain, which is different from the number of copies of said second enzymatic active domain as comprised on said second polypeptide of said combination. Furthermore, any further polypeptide of said exemplified combination encompassing the second compound of the invention may comprise a number of copies of further enzymatic active domain, which is different from the number of copies of said further enzymatic active domain as comprised on said first and second polypeptide of said combination. Although a combination of distinct polypeptides each comprising a single distinct enzymatic active domain showed synergistic lytic activity as compared to the lytic activity of each separate polypeptide, it was surprisingly found by the present inventors that polypeptides comprising a multiplicity of enzymatic active domains show superior lytic activity as compared to polypeptides comprising a single enzymatic active domain.

Moreover, a combination of distinct enzymatic domains on distinct polypeptides wherein at least one of said distinct polypeptides comprises a multiplicity of enzymatic active domains was found superior over a combination wherein all said distinct polypeptides comprise a single distinct enzymatic active domain. Moreover, a combination encompassing the second compound according to the invention, wherein a first, second, third and/or further polypeptide comprise a multiplicity of a first, second, third and/or further enzymatic active domain according to the invention, respectively, was found superior over a combination encompassing the second compound according to the invention, wherein said first, second, third and/or further polypeptide comprise a single copy of said first, second, third and/or further enzymatic active domain, respectively, and preferably wherein said multiplicity, as defined herein, is 2, i.e. a duplicate. In a preferred embodiment, the synergistic effect of a combination encompassing the second compound according to the invention, wherein a first, second, third and/or further polypeptide according to the invention comprise a multiplicity of a first, second, third and/or further enzymatic active domain according to the invention, respectively, was found superior over a combination encompassing the second compound according to the invention, wherein said first, second, third and further polypeptide comprise a single copy of said first, second, third and further enzymatic active domain, respectively, and preferably wherein said multiplicity, as defined herein below, is 2, i.e. a duplicate.

Preferably, a first and/or second polypeptide of a combination encompassing the second compound according to the invention, comprises a different multiplicity of a first and/or second enzymatic active domain according to the invention. Multiplicity of said first and second domain is defined as previously herein as a number of copies, preferably indicated by k, l, n and p, of said first and second domain indicated as follows:

k indicates the number of copies of said first enzymatic active domain on said first polypeptide;
l indicates the number of copies of said second enzymatic active domain on said first polypeptide;
n indicates the number of copies of said first enzymatic active domain on said second polypeptide;
p indicates the number of copies of said second enzymatic active domain on said second polypeptide;
and wherein k and p are independent integers from 1-10, 1-9, 1-8, 1-7, 1-6, 1-5, 1-4, 1-3, or preferably 1-2, and l and n are independent integers from 0-10, 0-9, 0-8, 0-7, 0-6, 0-5, 0-4, 0-3, or preferably 0-2, and wherein k is a different integer than n and/or l is a different integer than p, most preferably k and p are 2 and l and n are 0.

Preferably, a first, second and third polypeptide encompassing the second compound of the invention comprise a different multiplicity of a first, second and third enzymatic active domain according to the invention.

Multiplicity of said first, second and third domain is defined as previously herein as a number of copies, preferably indicated by k, l, m, n, p, q, r, s and t, of said first, second and third domain indicated as follows:

k indicates the number of copies of said first enzymatic active domain on said first polypeptide;
l indicates the number of copies of said second enzymatic active domain on said first polypeptide;
m indicates the number of copies of said third enzymatic active domain on said first polypeptide;
n indicates the number of copies of said first enzymatic active domain on said second polypeptide;
p indicates the number of copies of said second enzymatic active domain on said second polypeptide;
q indicates the number of copies of said third enzymatic active domain on said second polypeptide;
r indicates the number of copies of said first enzymatic active domain on said third polypeptide;
s indicates the number of copies of said second enzymatic active domain on said third polypeptide;
t indicates the number of copies of said third enzymatic active domain on said third polypeptide;
and wherein k, p and t are independent integers from 1-10, 1-9, 1-8, 1-7, 1-6, 1-5, 1-4, 1-3, or preferably 1-2, and l, m, n, q, r, and s are independent integers from 0-10, 0-9, 0-8, 0-7, 0-6, 0-5, 0-4, 0-3, or preferably 0-2, and wherein k is a different integer than n and/or r, and/or l is a different integer than p and/or s, and/or t is a different integer than m or q, most preferably k, p and t are 2 and l, m, n, q, r, and s are 0.

Preferably, a first, second, third and further polypeptide encompassing the second compound of the invention comprise a different multiplicity of a first, second, third and further enzymatic active domain according to the invention. Multiplicity of said further enzymatic active domain in view of said first, second and third enzymatic active domain is to be construed herein in an analogous manner as defined herein above for a first, second and third enzymatic active domain.

Preferably a first, second, third or further polypeptide encompassing the second compound according to the invention has a length of at least 140, 150, 160, 170, 180, 190, 200, 210, 220, 230, 240, 250, 260, 270, 280, 290, 300, 310, 320 or 330 amino acids and/or a length of at most 850, 800, 750, 700, 650, 600, 550, 500, 490, 480, 470, 460, 450, 440, 430, 420, 410, 400, 390, 380 or 370 amino acids. More preferably, a first, second or third polypeptide encompassing the second compound according to the invention has a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first and second polypeptide encompassing the second compound according to the invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first and second polypeptide according to the invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first, second and third polypeptide encompassing the second compound according to the invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first, second and third polypeptides encompassing the second compound according to the invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

Preferably a first, second, third and further polypeptide encompassing the second compound according to the invention each have a length of at least 140, 150, 160, 170, 180, 190, 200, 210, 220, 230, 240, 250, 260, 270, 280, 290, 300, 310, 320 or 330 amino acids and/or a length of at most 800, 850, 700, 650, 600, 550, 500, 490, 480, 470, 460, 450, 440, 430, 420, 410, 400, 390, 380 or 370 amino acids. More preferably, a first, second, third and further polypeptides encompassing the second compound according to the invention each have a length of 140-850, 140-800, 140-750, 140-700, 140-650, 140-600, 140-550 140-500, 140-490, 140-480, 140-470, 140-460, 140-450, 140-440, 140-430, 140-420, 140-410, 140-400, 140-390, 140-380, 140-370, 150-850, 160-850, 170-850, 180-850, 190-850, 200-850, 210-850, 220-850, 230-850, 240-850, 250-850, 260-850, 270-850, 280-850, 290-850, 300-850, 310-850, 320-850 or 330-850 amino acids.

An embodiment provides a combination of a source of a first and a second enzymatic active domain encompassing the second compound according to the invention, wherein said first and second enzymatic active domains are comprised on distinct, first and second polypeptides of the invention, wherein said first polypeptide is free of said second enzymatic active domain and said second polypeptide is free of said first enzymatic active domain. Moreover, provided is a combination according to the invention, wherein l and n are 0.

Another embodiment provides a combination of a source of a first, second and third enzymatic active domain encompassing the second compound according to the invention, wherein said first, second and third enzymatic active domains are comprised on distinct, first, second and third polypeptides, wherein said first polypeptide is free of said second and third enzymatic active domain, said second polypeptide is free of said first and third enzymatic active domain, and said third polypeptide is free of said first and second enzymatic active domain. Moreover, provided is a combination according to the invention, wherein l, m, n, q, r and s are 0. Even more preferably, the invention provides a combination encompassing the second compound according to the invention, wherein l, m, n, q, r and s are 0 and k, p and t are 2.

Another embodiment provides a combination of a source of a first, second, third and further enzymatic active domain encompassing the second compound according to the invention, wherein said first, second, third and further enzymatic active domains are comprised on a distinct, first, second, third and further polypeptide, respectively, wherein preferably said first polypeptide is free of said second, third and further enzymatic active domain;
  preferably said second polypeptide is free of said first, third and further enzymatic active domain;
  preferably said third polypeptide is free of said first, second and further enzymatic active domain; and,
  preferably said further polypeptide is free of said first, second and third enzymatic active domain.

Preferably said first, second, third and further enzymatic active domain are comprised within said first, second, third and further polypeptide, respectively, in duplicate, i.e. wherein the multiplicity as identified herein is 2. Also encompassed is a combination encompassing the second compound according to the invention, wherein a first, second and/or third polypeptide according to the invention are not free of a first, second and/or third enzymatic active domain according to the invention, but said first, second and/or third polypeptide differ in multiplicity of said first, second and/or third enzymatic active domain. Moreover, encompassed is a combination encompassing the second compound according to the invention, wherein at least one of k, l, m, n p, q, r, s or t is 2 and wherein any of the other k, l, m, n p, q, r, s and/or t is 1 or 0. Preferred is a combination encompassing the second compound according to the invention, wherein a first, second, third and/or further polypeptide is a polypeptide that has at least 80, 81, 82, 83, 84, 85, 86, 87, 88, 89, 90, 91, 92, 93, 94, 95, 96, 97, 98, 99 or 100% identity with a polypeptide selected from the group consisting of SEQ ID NO: 26, 28, 30, 32, 34, 36, 38, 40, 42, 44, 46, 48, 50, 52, 54, 56, 58, 60, 62, 64, 66, 68, 70, 72, 76, 78, 80, 82, 84, 86, 88, 90, 92, 94, 98 or 100.

Within the context of the invention, several preferred, non-limiting, combinations encompassing the second compound according to the invention are envisaged, which are listed here below.

Preferred is a combination of a source of first enzymatic active domain and a second enzymatic active domain, wherein said first and second enzymatic active domains are comprised on distinct first and second polypeptides, and wherein said first enzymatic active domain is a cysteine, histidine-dependent amidohydrolases/peptidase domain and said second enzymatic active domain is an endopeptidase domain or wherein said first enzymatic active domain is a cysteine, histidine-dependent amidohydrolases/peptidase domain and said second enzymatic active domain is amidase domain or wherein said first enzymatic active domain is an endopeptidase domain and said second enzymatic active domain is amidase domain, wherein said distinct first and second each further comprises a cell wall-binding domain, and wherein each of said distinct first and second polypeptides comprises a multiplicity of said first or second enzymatic active domain, preferably said multiplicity being 2, i.e. a duplicate.

Also preferred is a combination of a source of first and second enzymatic active domain, wherein said first and second enzymatic active domains are comprised on distinct first and second polypeptides, and wherein said first enzymatic domain is histidine-dependent amidohydrolases/peptidase domain and said second enzymatic active domain is an endopeptidase domain or said first enzymatic active domain is a cysteine, histidine-dependent amidohydrolases/peptidase domain and said second enzymatic active domain is amidase domain or said first enzymatic active domain is an endopeptidase domain and said second enzymatic active domain is amidase domain, and wherein said first and second polypeptide each further comprise a cell wall binding domain.

Also preferred is a combination of a source of first enzymatic active domain and a second enzymatic active domain, wherein said first and second enzymatic active domains are comprised on distinct first and second polypeptides, and wherein said first enzymatic active domain is a cysteine, histidine-dependent amidohydrolases/peptidase domain and said second enzymatic active domain is an endopeptidase domain, and wherein said combination further comprises a source of a third enzymatic active domain comprised on a distinct third polypeptide, wherein said third enzymatic active domain is an amidase domain and said distinct first, second and third polypeptide each further comprises a cell wall-binding domain, and wherein each of said distinct first, second and third polypeptides comprises a multiplicity of said first, second or third enzymatic active domain, preferably said multiplicity being 2, i.e. a duplicate.

Also preferred is a combination of a source of first, second and third enzymatic active domain, wherein said first, second and third enzymatic active domains are comprised on distinct first, second and third polypeptides, and wherein said first enzymatic domain is histidine-dependent amidohydrolases/peptidase domain, said second enzymatic active domain is an endopeptidase domain and said third enzymatic active domain is an amidase domain, and wherein said first, second and third polypeptide each further comprise a cell wall binding domain.

Also preferred is a combination wherein, a first enzymatic active domain according to the invention has at least 80, 81, 82, 83, 84, 85, 86, 87, 88, 89, 90, 91, 92, 93, 94, 95, 96, 97, 98, 99 or 100% identity with SEQ ID NO: 10 and a second enzymatic active domain according to the invention as at least 80, 81, 82, 83, 84, 85, 86, 87, 88, 89, 90, 91, 92, 93, 94, 95, 96, 97, 98, 99 or 100% identity with SEQ ID NO: 16.

Also preferred is a combination wherein, a first enzymatic active domain according to the invention has at least 80, 81, 82, 83, 84, 85, 86, 87, 88, 89, 90, 91, 92, 93, 94, 95, 96, 97, 98, 99 or 100% identity with SEQ ID NO: 10 and a second enzymatic active domain according to the invention as at least 80, 81, 82, 83, 84, 85, 86, 87, 88, 89, 90, 91, 92, 93, 94, 95, 96, 97, 98, 99 or 100% identity with SEQ ID NO: 18.

Also preferred is a combination wherein, a first enzymatic active domain according to the invention has at least 80, 81, 82, 83, 84, 85, 86, 87, 88, 89, 90, 91, 92, 93, 94, 95, 96, 97, 98, 99 or 100% identity with SEQ ID NO: 16 and a second enzymatic active domain according to the invention as at least 80, 81, 82, 83, 84, 85, 86, 87, 88, 89, 90, 91, 92, 93, 94, 95, 96, 97, 98, 99 or 100% identity with SEQ ID NO: 18.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 46 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 70.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 52.

More preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 34.

More preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 70 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination, wherein a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 34.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52 and a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46.

Also preferred is a combination wherein, a first enzymatic active domain according to the invention has at least 80, 81, 82, 83, 84, 85, 86, 87, 88, 89, 90, 91, 92, 93, 94, 95, 96, 97, 98, 99 or 100% identity with SEQ ID NO: 10, a second enzymatic active domain according to the invention as at least 80, 81, 82, 83, 84, 85, 86, 87, 88, 89, 90, 91, 92, 93, 94, 95, 96, 97, 98, 99 or 100% identity with SEQ ID NO: 16 and a third enzymatic active domain according to the invention has at least 80, 81, 82, 83, 84, 85, 86, 87, 88, 89, 90, 91, 92, 93, 94, 95, 96, 97, 98, 99 or 100% identity with SEQ ID NO: 18.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 26.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 26.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 36, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 48 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 30.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 26.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 26.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 32, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 44 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 60, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 72 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 54.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 50.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 56, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 65, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 68 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 52.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 58, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 46 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 28.

Also preferred is a combination wherein, a first polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 34, a second polypeptide according to the invention as at least 80, 81, 82, 83, 84, 85, 86, 87, 88, 89, 90, 91, 92, 93, 94, 95, 96, 97, 98, 99 or 100% identity with SEQ ID NO: 70 and a third polypeptide according to the invention has at least 80, 81, 82, 83, 84, 85, 86, 87, 88, 89, 90, 91, 92, 93, 94, 95, 96, 97, 98, 99 or 100% identity with SEQ ID NO: 28.

It is to be understood that a combination as described herein encompassing the second compound according to the invention includes mixtures of a source of a first, a source of a second and optionally a source of a third and/or further enzymatic active domain according to in varying ratios. Preferably, such combination comprises a source a first and a source a second enzymatic active domain according to the invention, wherein said first and second enzymatic active domain are present in equimolar amounts. Also preferred is a combination comprising a source a first, a source a second and a source a third enzymatic active domain according to the invention, wherein said first, second and third enzymatic active domain are present in equimolar amounts. Also preferred is a combination comprising a source of a first, a source of a second, a source of a third and a source of a further enzymatic active domain according to the invention, wherein said first, second, third and further enzymatic active domain are present in equimolar amounts.

In a second aspect, the invention provides for a kit of parts comprising:
 a) a first vial containing a first composition comprising a first compound as defined in the first aspect of the invention; and,
 b) a second vial containing a second composition comprising a second compound as defined in the first aspect of the invention; and optionally,
 c) instructions for use, preferably comprising a dosage regime.

Preferably, said kit of parts, more specifically said first and second composition of said kit of parts, is for use as a medicament, preferably for use in treatment of rosacea, more preferably for use in the treatment of telangiectasia, erythema and/or flushing, preferably telangiectasia, erythema and/or flushing associated with inflammation induced vasodilatation, as further detailed herein. A dosage regime is to be understood herein as an instruction for administration to an individual in the need thereof, preferably an instruction indicating an administration route, administration frequency and administration dosage, and optionally an instruction for admixing said first and second compound just before administration, as required for treatment, preferably required for treatment of rosacea, more preferably for use in the treatment of telangiectasia, erythema and/or flushing, preferably telangiectasia, erythema and/or flushing associated with inflammation induced vasodilatation, as further detailed herein. Preferred administration routes, frequencies and dosages are further detailed herein. In an embodiment, said first composition according to a second aspect and/or said second composition according to a second aspect of the invention is administered separately, preferably as part of an overall treatment regimen. In an alternative embodiment, said first composition according to a second aspect and said second composition according to a second aspect of the invention are stored separately, and admixed just before administration. Preferably, "just before" is to be understood herein as less than 120, 60, 30, 15, 5, 4, 3, 2 or 1 minutes before administration, preferably less than 5 minutes before administration.

Said first and said second vial may be any vial, bottle, tube, ampoule, container, flask or the like, suitable for storing said first and second composition as defined herein, respectively. Preferably said first and/or second vial has a volume of between 0.1 and 500 mL, preferably between 1 and 100 mL, more preferably of about 5, 10, 50 or 100 mL.

In a third aspect, the invention provides for a method of treatment comprising the administration of a composition according to the first aspect of the invention and/or the sequential or simultaneous administration of a first and second compound of a kit of parts according to the second aspect of the invention.

Preferably, said method of treatment is a method for preventing, delaying and/or curing rosacea, more preferably treatment of telangiectasia, erythema and/or flushing, preferably telangiectasia, erythema and/or flushing associated with inflammation induced vasodilatation, as further detailed herein.

Encompassed in the invention is a composition according to the first aspect of the invention and/or a kit of parts according to second aspect of the invention, for use as a medicament. Preferably, said composition according to the first aspect of the invention and/or said kit of parts according to second aspect of the invention is for use in preventing, delaying and/or curing rosacea, more preferably for use in the treatment of telangiectasia, erythema and/or flushing, preferably telangiectasia, erythema and/or flushing associated with inflammation induced vasodilatation, as further detailed herein. Also encompassed in the invention is the use of a composition according to the first aspect of the invention and/or a kit of parts according to second aspect of the invention for the manufacture of a medicament. Preferably, said medicament is for preventing, delaying and/or curing rosacea, more preferably for preventing, delaying and/or curing telangiectasia, erythema and/or flushing, preferably telangiectasia, erythema and/or flushing associated with inflammation induced vasodilatation, as further detailed herein. Preferably, said composition according to the first aspect, a first composition of a kit of parts according to the second aspect and/or a second composition of a kit of parts according to the second aspect and/or medicament as defined herein is a topical formulation understood herein as a formulation, including a microencapsulated formulation, being suitable for topical administration and may be in the form of a cream, ointment, solution, powder, spray, aerosol, capsule, solid or gel, and/or may be bonded to a solid surface, e.g. by immobilization with affinity ligands or through ionic/hydrophobic interactions and covalent immobilization.

A composition according to the first aspect of the invention and/or a first and/or second composition of a kit of parts according to the second aspect of the invention may also form part of a body wash, soap, application stick or cosmetic.

A composition according to the first aspect and/or a second composition of a kit of parts according to the second aspect and/or a mixture resulting from admixing said first and second composition of a kit of parts according to the second aspect just before administration as earlier indicated herein, is preferably said to be active, functional or therapeutically active when it decreases the amount of bacterial cells, preferably gram positive bacterial cells, more preferably the amount of *Staphylococcus* bacterial cells, most preferably the amount of *Staphylococcus aureus* bacterial cells, present in a patient or in a cell of said patient or in a cell line or in a cell free in vitro system and preferably means that 99%, 90%, 80%, 70%, 60%, 50%, 40%, 30%, 20%, 10%, 5% or less of the initial amount of said bacterial cells is still detectable. More preferably, no bacterial cell, preferably no gram positive bacterial cell, more preferably no *Staphylococcus* bacterial cell, most preferably no *Staphylococcus aureus* bacterial cell, is detectable. In this paragraph, the expression "amount of bacterial cells" preferably means viable bacterial cells. Staphylococci of all genera may be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Viable Staphylococci may be detected using standard techniques known by the artisan such as microbiological bacterial culture techniques and/or real-time quantitative reverse transcription polymerase chain reaction to assay for bacterial mRNA. A decrease in amount of bacterial cells according to the invention is preferably assessed in a tissue or in a cell of an individual or a patient by comparison to the amount present in said individual or patient before treatment with said composition or polypeptide of the invention. Alternatively, the comparison can be made with a tissue or cell of said individual or patient which has not yet been treated with said composition or polypeptide in case the treatment is local.

Preferably a composition according to the first aspect of the invention and/or a second composition of a kit of parts of the second aspect of the invention, and/or a resulting mixture resulting from admixing the first and second composition of the kit of part of the second aspect of the invention just before administration as identified herein before comprises an amount of a second compound as defined herein which is therapeutically active as earlier identified herein. Preferably, said composition is for topic administration to an individual in the need thereof, preferably to a patient suffering from rosacea, telangiectasia, erythema and/or flushing, and comprises said second compound in an effective amount, preferably a concentration of 0.001-10% by weight of the total composition. Depending on the specific activity of the second compound, the effective amount may be as low about a few micrograms/ml such as about 1, 2, 3, 4, 5, 6, 7, 8, 9, 10 microgram/ml to about several milligrams/ml such as about 1, 2, 3, 4, 5, 6, 7, 8, 9, 10 milligram/ml Preferably a composition according to the first aspect of the invention and/or a first composition of a kit of parts of the second aspect of the invention, and/or a resulting mixture resulting from admixing the first and second composition of the kit of part of the second aspect of the invention just before administration as identified herein before is a composition for topical application for the treatment of rosacea, telangiectasia, erythema and/or flushing, comprising a vasoconstrictive compound according to the invention, selected from, but not limited to a sympathomimetic compound according to the invention; or a combination of two or more of these. Preferably, said composition is for topic administration to an individual in the need thereof, preferably to a patient suffering from rosacea, more preferably telangiectasia, erythema and/or flushing, preferably telangiectasia, erythema and/or flushing associated with inflammation induced vasodilatation, and comprises said vasoconstrictive compound according to the invention in an effective amount, preferably in the range of 0.01 to 10% by weight of the total composition, preferably in the range of 0.05 to 5%, more preferably in a range of 0.05 to 2.5%, even more preferably in a range of 0.1 to 1%.

Preferably a composition according to the first aspect of the invention and/or a first composition of a kit of parts of the second aspect of the invention, and/or a resulting mixture resulting from admixing the first and second composition of the kit of part of the second aspect of the invention just before administration as identified herein before is a composition for topic application for the treatment of rosacea, more preferably telangiectasia, erythema and/or flushing, preferably telangiectasia, erythema and/or flushing associated with inflammation induced vasodilatation, comprising a vasoconstrictive compound according to the invention in the range of 0.05 to 5%, by weight of the total composition preferably in a range of 0.05 to 2.5% more preferably in a range of 0.1 to 1%, even more preferably comprising about 0.25% of a vasoconstrictive compound according to the invention. About is defined herein as a value minus or plus 10% of the indicated value.

A composition according to the first aspect, a first composition of a kit of parts according to the second aspect and/or a second composition of a kit of parts according to the second aspect and/or medicament as defined herein may be in the liquid, solid or semi-liquid or semi-solid form, preferably further comprising a pharmaceutical acceptable carrier, excipient and/or stabilizer. Examples of pharmaceutically acceptable carriers, excipients and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinylpyrrolidone; amino acids such as glycine, glutamine, asparagine, arginine or lysine; monosaccharides, disaccharides, and other carbohydrates including glucose mannose, or dextrins; chelating agents such as EDTA; sugar alcohols such as mannitol or sorbitol; salt-forming counterions such as sodium; and/or nonionic surfactants such as polysorbate (TWEEN™), polyethylene glycol (PEG), and poloxamers (PLURONICS™); and polymer thickeners such as hydrophilic and hydroalcoholic gelling agents frequently used in the cosmetic and pharmaceutical industries, preferably a gelling agent comprises between about 0.2% and about 4% by weight composition. A composition according to the first aspect, a first composition of a kit of parts according to the second aspect and/or a second composition of a kit of parts according to the second aspect and/or medicament as defined herein can also include a lubricant, a wetting agent, a sweetener, a flavoring agent, an emulsifier, a suspending agent, a sun screen such as, but not limited to, titanium dioxide or methyl cinnamate, and/or a preservative, in addition to the above ingredients, preferably a preservative is present as about 0.05% to 0.5% by weight of the total composition. A composition according to the first aspect, a first composition of a kit of parts according to the second aspect and/or a second composition of a kit of parts according to the second aspect and/or medicament as defined herein can also include a carrier which are known in the art (such as a carbohydrate and a sugar-alcohol) to aid in the exposure of the skin to a medicament.

Preferably, a composition according to the first aspect, a first composition of a kit of parts according to the second aspect and/or a second composition of a kit of parts according to the second aspect and/or a medicament as defined herein further comprises and additional active ingredient. An additional active ingredient may be any of, but is not limited to, a standard or conventional antibiotic agent such as, but not limited to penicillin, synthetic penicillins, bacitracin, methicillin, cephalosporin, polymyxin, cefaclor, Cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate and/or chelating agents; an antifungal, such as, but not limited to, oxiconazole nitrate, ciclopirox olamine, ketoconazole, miconazole nitrate and butoconazole nitrate; an anti-androgen, such as, but not limited to, flutamide and/or finasterid; a local anesthetic agent, such as, but not limited to tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate and/or pramoxine hydrochloride; and dapsone which has both antimicrobial and anti-inflammatory properties. Other additional active ingredients may be selected from the groups listed in Culp and Scheinfeld [8]. Another additional active ingredients may be an anti-inflammatory agent selected from the group consisting of a corticosteroid a calcineurin inhibitor, an immunotherapeutic compound, a recombinant human IFN-gamma, a microbial probiotic, a cytokine modulator, an inflammatory cell recruitment blocker and a T cell activation inhibitor. Preferred weight percentages of antimicrobial agents or other additional active agents are 0.1% to 10% weight of the total composition. Preferred weight percentages for local anesthetics are 0.025% to 5% by weight of the total composition.

A composition according to the first aspect, a first composition according to a second aspect and/or a second composition according to a second aspect and/or medicament as defined herein can be used to treat animals, including humans, suffering from any of the conditions as identified herein above, preferably from rosacea, more preferably telangiectasia, erythema and/or flushing, preferably telangiectasia, erythema and/or flushing associated with inflammation induced vasodilatation.

A preferred route of administration of said composition and/or said medicament is any suitable route of administration that can be used to administer said composition according to the first aspect, said first composition according to a second aspect and/or said second composition according to a second aspect and/or medicament as defined herein including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. Preferably, said composition according to the first aspect, said first composition according to a second aspect and/or said second composition according to a second aspect and/or medicament as defined herein are administered topical, preferably at the site of rosacea, more preferably telangiectasia, erythema and/or flushing, preferably telangiectasia, erythema and/or flushing associated with inflammation induced vasodilatation.

A preferred administration frequency of said composition and/or said medicament is once or twice a day, preferably to the area of the skin affected. Preferably said treatment is continued as long as required for the rosacea to be cleared. Preferably said treatment is continued for 2 to 3 days, for 7 to 10 days and/or for 2 to 3 weeks. Preferably a total amount of composition for topic application is administered as identified herein resulting in a total application of about 1 gram of vasoconstrictive compound to the person in the need thereof.

A preferred dosage of administration of said composition and/or said medicament is a dosage containing an effective total amount of said first and second compound resulting in the prevention, delay and/or cure of rosacea, more preferably telangiectasia, erythema and/or flushing, preferably telangiectasia, erythema and/or flushing associated with inflammation induced vasodilatation.

Definitions

In the embodiments of the invention, telangiectasia, erythema and/or flushing, preferably telangiectasia, erythema and/or flushing associated with inflammation induced vasodilatation, are usually conditions associated with rosacea. These conditions (telangiectasia, erythema and/or flushing, preferably telangiectasia, erythema and/or flushing associated with inflammation induced vasodilatation) can however also be a phenomenon on its own, i.e. not necessarily associated with rosacea; treatment of these conditions not necessarily associated with rosacea is also within the scope of the invention. The term "associated" herein in the context of telangiectasia, erythema and/or flushing associated with inflammation induced vasodilatation" means that the telangiectasia, erythema and/or flushing could be caused by inflammation induced vasodilatation but the telangiectasia, erythema and/or flushing could also be already present and be aggravated by inflammation induced vasodilatation. In the embodiments of the invention, the inflammation induced vasodilatation is preferably induced directly by a microbial compound or antigen, or indirectly via innate and adaptive immunity mediated e.g. via a Toll-Like Receptors (TLR) or the complement system. A preferred TLR is TLR 2. Preferably the microbe is a Gram-positive bacterium, preferably a *Staphylococcus*, more preferably *Staphylococcus aureus*.

"Sequence identity" or "identity" in the context of amino acid- or nucleic acid-sequence is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. Within the invention, sequence identity with a particular sequence preferably means sequence identity over the entire length of said particular polypeptide or polynucleotide sequence. The sequence information as provided herein should not be so narrowly construed as to require inclusion of erroneously identified bases. The skilled person is capable of identifying such erroneously identified bases and knows how to correct for such errors. "Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps). Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

A polynucleotide is represented by a nucleotide sequence. A polypeptide is represented by an amino acid sequence. A nucleic acid construct is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct is operably linked to one or more control sequences, which direct the production or expression of said peptide or polypeptide in a cell or in a subject.

As used herein the term "heterologous sequence" or "heterologous nucleic acid" is one that is not naturally found operably linked as neighboring sequence of said first nucleotide sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature. "Operably linked" is defined herein as a configuration in which a control sequence is appropriately placed at a position relative to the nucleotide sequence coding for the polypeptide of the invention such that the control sequence directs the production/ expression of the peptide or polypeptide of the invention in a cell and/or in a subject.

"Operably linked" may also be used for defining a configuration in which a sequence is appropriately placed at a position relative to another sequence coding for a functional domain such that a chimeric polypeptide is encoded in a cell and/or in a subject.

Expression will be understood to include any step involved in the production of the peptide or polypeptide including, but not limited to, transcription, post-transcriptional modification, translation, post-translational modification and secretion.

Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the current invention, the term usually refers to an extrachromosomal, self-replicating vector which harbors a selectable antibiotic resistance.

An expression vector may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide-1 of the transcription start site (TSS).

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. The term "control sequences" is defined herein to include all components, which are necessary or advantageous for the expression of a polypeptide. Each control sequence may be native or foreign to the nucleic acid sequence encoding the polypeptide. Such control sequences include, but are not limited to, a leader, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. At a minimum, the control sequences include a promoter, and transcriptional and translational stop signals.

The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence, which is recognized by a host cell for expression of the nucleic acid sequence. The promoter sequence contains transcriptional control sequences, which mediate the expression of the polypeptide. The promoter may be any nucleic acid sequence, which shows transcriptional activity in the cell including mutant, truncated, and hybrid promoters, and may be obtained from genes encoding extracellular or intracellular polypeptides either homologous or heterologous to the cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator, which is functional in the cell, may be used in the invention.

The control sequence may also be a suitable leader sequence, a non-translated region of a mRNA which is important for translation by the host cell. The leader sequence is operably linked to the 5' terminus of the nucleic acid sequence encoding the polypeptide. Any leader sequence, which is functional in the cell, may be used in the invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence, which is functional in the cell, may be used in the invention.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the invention in any way.

EXAMPLES

Example 1: Treatment of Rosacea Patients

Rosacea patients are treated with a combination of an antibacterial agent and a vasoconstrictor according to the invention. The treatment results in effective treatment of rosacea, telangiectasia, erythema and/or flushing; the bacterial trigger for inflammation is suppressed by the antibacterial agent, resulting in less inflammation-related vasodilatation, in turn allowing a lower need for a vasoconstrictive compound.

Example 2: Combination Treatment with a Vasoconstrictor and an Antibacterial Specific for *Staphylococcus aureus*; a Comparative Study In several forms of dermatitis, like rosacea, courses of topical vasoconstrictor therapy are used to suppress symptoms of local redness. However, vasoconstrictors such as brimonidine do not treat the underlying cause of the vasodilatation causing the redness, and symptoms are known to return quickly after the alfa-adrenergic vasoconstrictive effect has waned.

The inventors considered that of the underlying vasodilatory triggers for local redness is inflammation, that can be caused by local irritation or infection of the skin by bacteria, like *Staphylococcus aureus*. *Staphylococcus aureus* is the most prevalent cause of bacterial skin infections and is considered to play a role in inflammatory skin conditions like eczema and acne as a local trigger of inflammatory symptoms and (secondary) infection.

The inventors hypothesized that a specific antibacterial compound would be effective in combination with vasoconstriction treatment in inflammatory skin conditions like rosacea. Accordingly, a compound specifically targeting *Staphylococcus aureus* was used. The compound Staphefekt™ SA. 100 (comprised in Gladskin™) was obtained from Micreos Human Health B.V., The Netherlands. Since Staphefekt™ eradicates *S. aureus* as an etiological factor of local inflammation, it was hypothesized that Staphefekt™ treatment combined with vasoconstrictor treatment would alleviate the total burden of symptoms in inflammatory skin conditions like rosacea, comprising amongst others inflammatory and vascular symptoms, in a synergistic manner, as both the inflammatory trigger, causing vasodilatation amongst other symptoms, and the vasodilatation itself was targeted.

To study the use of vasoconstrictor treatment during Staphefekt™ treatment, the relative reduction in total symptom score was compared between a study conducted with Staphefekt™ (Gladskin™) in a cohort of rosacea patients, and a case study of rosacea first using monotherapy with a vasoconstrictor (Mirvaso™ gel, comprising 0.3% w/w brimonidine) and thereafter using combination therapy of the vasoconstrictor with Staphefekt™ (Gladskin™).

Surprisingly, the reduction in total symptom scores with the combination of the vasoconstrictor in combination with Staphefekt™ was considerably larger than the sum of the reductions achieved with Staphefekt™ alone or the vasoconstrictor alone, evidencing the synergistic effect of combination treatment using both compounds on vascular symptoms in inflammatory skin diseases (FIG. 1).

The synergistic effect of the combination of a vasoconstrictor and Staphefekt™ also implies that a lower dose or shorter course of vasoconstrictor treatment would be effective in combination therapy with Staphefekt™ to achieve the same amount of total symptom reduction.

REFERENCES

1 Two A M, Wu W, Gallo R L et al. Rosacea: part I. Introduction, categorization, histology, pathogenesis, and risk factors. J Am Acad Dermatol 2015; 72: 749-58; quiz 59-60.
2 Steinhoff M, Schauber J, Leyden J J. New insights into rosacea pathophysiology: a review of recent findings. J Am Acad Dermatol 2013; 69: S15-26.
3 Yamasaki K, Kanada K, Macleod D T et al. TLR2 expression is increased in rosacea and stimulates enhanced serine protease production by keratinocytes. J Invest Dermatol 2011; 131: 688-97.
4 Koller B, Muller-Wiefel A S, Rupec R et al. Chitin modulates innate immune responses of keratinocytes. PLoS One 2011; 6: e16594.
5 Lacey N, Delaney S, Kavanagh K et al. Mite-related bacterial antigens stimulate inflammatory cells in rosacea. Br J Dermatol 2007; 157: 474-81.
6 Belkaid Y, Segre J A. Dialogue between skin microbiota and immunity. Science 2014; 346: 954-9.
7 Foumier B, Philpott D J. Recognition of *Staphylococcus aureus* by the innate immune system. Clin Microbiol Rev 2005; 18: 521-40.
8 Culp and Scheinfeld. Rosacea: A review. Pharmacy and Therapeutics 2009; 34: 38-45.
9 Shanler, S, Ondo, A L. Successful treatment of the erythema and flushing of rosacea using a topically applied selective alpha-adrenergic receptor agonist, oxymetazoline. Arch Dermatology 2007; 143: 1369-1371.

TABLE 1

SEQ ID NO overview table

| SEQ ID NO | Construct | Organism |
|---|---|---|
| 1 | Ply2638 endolysin CDS | Bacteriophage 2638A |
| 2 | Ply2638 endolysin PRT | Bacteriophage 2638A |
| 3 | CWT-LST CDS | *S. simulans* |
| 4 | CWT-LST PRT | *S. simulans* |
| 5 | CBD2638 CDS | Bacteriophage 2638A |
| 6 | CBD2638 PRT | Bacteriophage 2638A |
| 7 | CWT-NM3 CDS | *S. aureus* phage phiNM3 |
| 8 | CWT-NM3 PRT | *S. aureus* phage phiNM3 |
| 9 | CHAPK CDS | *S.* phage K |
| 10 | CHAPK PRT | *S.* phage K |
| 11 | CHAP-ΦTwort CDS | *S.* phage Twort |
| 12 | CHAP-ΦTwort PRT | *S.* phage Twort |
| 13 | M23-2638 CDS | Bacteriophage 2638A |
| 14 | M23-2638 PRT | Bacteriophage 2638A |
| 15 | M23-LST CDS | *S. simulans* |
| 16 | M23-LST PRT | *S. simulans* |
| 17 | Ami2638 CDS | Bacteriophage 2638A |
| 18 | Ami2638 PRT | Bacteriophage 2638A |
| 19 | CHAPK_CHAPK_CWT-LST CDS | artificial construct |
| 20 | CHAPK_CHAPK_CWT-LST PRT | artificial construct |
| 21 | M23-LST_M23-LST_CWT-LST CDS | artificial construct |
| 22 | M23-LST_M23-LST_CWT-LST PRT | artificial construct |
| 23 | Ami2638_ami2638_CWT-LST CDS | artificial construct |
| 24 | Ami2638_ami2638_CWT-LST PRT | artificial construct |
| 25 | HXaAmi2638_CBD2638 CDS | artificial construct |
| 26 | HXaAmi2638_CBD2638 PRT | artificial construct |
| 27 | HXaAmi2638_CWT-LST CDS | artificial construct |
| 28 | HXaAmi2638_CWT-LST PRT | artificial construct |
| 29 | HXaAmi2638_CWT-NM3 CDS | artificial construct |
| 30 | HXaAmi2638_CWT-NM3 PRT | artificial construct |
| 31 | HXaCHAPK_CBD2638 CDS | artificial construct |
| 32 | HXaCHAPK_CBD2638 PRT | artificial construct |
| 33 | HXaCHAPK_CWT-LST CDS | artificial construct |
| 34 | HXaCHAPK_CWT-LST PRT | artificial construct |
| 35 | HXaCHAPK_CWT-NM3 CDS | artificial construct |
| 36 | HXaCHAPK_CWT-NM3 PRT | artificial construct |
| 37 | HXaCHAPTw_CBD2638 CDS | artificial construct |
| 38 | HXaCHAPTw_CBD2638 PRT | artificial construct |
| 39 | HXaCHAPTw_CWT-LST CDS | artificial construct |
| 40 | HXaCHAPTw_CWT-LST PRT | artificial construct |
| 41 | HXaCHAPTw_CWT-NM3 CDS | artificial construct |
| 42 | HXaCHAPTw_CWT-NM3 PRT | artificial construct |
| 43 | HXaM23-LST_CBD2638 CDS | artificial construct |
| 44 | HXaM23-LST_CBD2638 PRT | artificial construct |
| 45 | HXaM23-LST_CWT-LST CDS | artificial construct |

TABLE 1-continued

SEQ ID NO overview table

| SEQ ID NO | Construct | Organism |
|---|---|---|
| 46 | HXaM23-LST__CWT-LST PRT | artificial construct |
| 47 | HXaM23-LST__CWT-NM3 CDS | artificial construct |
| 48 | HXaM23-LST__CWT-NM3 PRT | artificial construct |
| 49 | HXaAmi2638__Ami2638__CBD2638 CDS | artificial construct |
| 50 | HXaAmi2638__Ami2638__CBD2638 PRT | artificial construct |
| 51 | HXaAmi2638__Ami2638__CWT-LST CDS | artificial construct |
| 52 | HXaAmi2638__Ami2638__CWT-LST PRT | artificial construct |
| 53 | HXaAmi2638__Ami2638__CWT-NM3 CDS | artificial construct |
| 54 | HXaAmi2638__Ami2638__CWT-NM3 PRT | artificial construct |
| 55 | HXaCHAPK__CHAPK__CBD2638 CDS | artificial construct |
| 56 | HXaCHAPK__CHAPK__CBD2638 PRT | artificial construct |
| 57 | HXaCHAPK__CHAPK__CWT-LST CDS | artificial construct |
| 58 | HXaCHAPK__CHAPK__CWT-LST PRT | artificial construct |
| 59 | HXaCHAPK__CHAPK__CWT-NM3 CDS | artificial construct |
| 60 | HXaCHAPK__CHAPK__CWT-NM3 PRT | artificial construct |
| 61 | HXaCHAPTw__CHAPTw__CBD2638 CDS | artificial construct |
| 62 | HXaCHAPTw__CHAPTw__CBD2638 PRT | artificial construct |
| 63 | HXaCHAPTw__CHAPTw__CWT-LST CDS | artificial construct |
| 64 | HXaCHAPTw__CHAPTw__CWT-LST PRT | artificial construct |
| 65 | HXaCHAPTw__CHAPTw__CWT-NM3 CDS | artificial construct |
| 66 | HXaCHAPTw__CHAPTw__CWT-NM3 PRT | artificial construct |
| 67 | HXaM23-LST__M23-LST__CBD2638 CDS | artificial construct |
| 68 | HXaM23-LST__M23-LST__CBD2638 PRT | artificial construct |
| 69 | HXaM23-LST__M23-LST__CWT-LST CDS | artificial construct |
| 70 | HXaM23-LST__M23-LST__CWT-LST PRT | artificial construct |
| 71 | HXaM23-LST__M23-LST__CWT-NM3 CDS | artificial construct |
| 72 | HXaM23-LST__M23-LST__CWT-NM3 PRT | artificial construct |
| 73 | His-tag with linker CDS | artificial construct |
| 74 | His-tag with linker PRT | artificial construct |
| 75 | LST CDS | S. simulans |
| 76 | LST PRT | S. simulans |
| 77 | HXaCHAP11__M23-2638__Ami2638__CBD2638 CDS | artificial construct |
| 78 | HXaCHAP11__M23-2638__Ami2638__CBD2638 PRT | artificial construct |
| 79 | HXaAmi11__M23-2638__Ami2638__CBD2638 CDS | artificial construct |
| 80 | HXaAmi11__M23-2638__Ami2638__CBD2638 PRT | artificial construct |
| 81 | HXaCHAPTw__Ami2638__M23-LST__CBD2638 CDS | artificial construct |
| 82 | HXaCHAPTw__Ami2638__M23-LST__CBD2638 PRT | artificial construct |
| 83 | HXaM23-LST__Ami2638__CBD2638 CDS | artificial construct |
| 84 | HXaM23-LST__Ami2638__CBD2638 PRT | artificial construct |
| 85 | HXaM23-2638__Ami2638__CBD2638__CBD2638 CDS | artificial construct |
| 86 | HXaM23-2638__Ami2638__CBD2638__CBD2638 PRT | artificial construct |
| 87 | HXaM23-2638__CBD2638 CDS | artificial construct |
| 88 | HXaM23-2638__CBD2638 PRT | artificial construct |
| 89 | HXaPly2638-Ply2638 CDS | artificial construct |
| 90 | HXaPly2638-Ply2638 PRT | artificial construct |
| 91 | HXaCHAPTw__Ami2638__M23-LST__CWT-LST CDS | artificial construct |
| 92 | HXaCHAPTw__Ami2638__M23-LST__CWT-LST PRT | artificial construct |
| 93 | HXaLST__LST CDS | artificial construct |
| 94 | HXaLST__LST PRT | artificial construct |
| 95 | HXaGFP__CBD2638 CDS | artificial construct |
| 96 | HXaGFP__CBD2638 PRT | artificial construct |
| 97 | CHAPΦ11 CDS | S. aureus phage phi 11 |
| 98 | CHAPΦ11 PRT | S. aureus phage phi 11 |
| 99 | AmiΦ11 CDS | S. aureus phage phi 11 |
| 100 | AmiΦ11 PRT | S. aureus phage phi 11 |
| 101 | EP15158880.3 endolysin PRT | artificial construct |

The invention claimed is:

1. A method for treating rosacea in a patient in need thereof comprising the sequential or simultaneous administration of a first compound and a second compound to the patient,
wherein said first compound is a vasoconstrictive compound selected from the group consisting of alpha(1)- and alpha(2)-adrenergic agonists and said second compound is a compound specifically targeting a *Staphylococcus* cell, and comprises one or more enzymatic active domains exhibiting peptidoglycan hydrolase activity.

2. The method according to claim 1, wherein said second compound further comprises at least one cell wall binding domain which specifically binds to the peptidoglycan cell wall of said *Staphylococcus* cell.

3. The method according to claim 2, wherein said cell wall binding domain originates from or is a homologue of a *Staphylococcus* phage endolysin, an *S. simulans* lysostaphin and/or an *S. capitis* ALE-1 bacteriocin.

4. The method according to claim 2, wherein said second compound comprises a cell wall binding domain that has at least 80% identity to SEQ ID NO: 6.

5. The method according to claim 1, wherein said one or more enzymatic active domains is selected from the group consisting of a cysteine, histidine dependent amidohydrolase/peptidase domain, an endopeptidase domain, an amidase domain and a glycosylhydrolase domain, and combinations thereof.

6. The method according to claim 1, wherein said second compound is a naturally occurring endolysin.

7. The method according to claim 1, wherein said second compound is a recombinant polypeptide comprising the one or more enzymatic active domains exhibiting peptidoglycan hydrolase activity.

8. The method according to claim 1, wherein the alpha(1)- and alpha(2)-adrenergic agonist is selected from the group consisting of Brimonidine, Tetrahydrozoline and Oxymetazoline.

* * * * *

SEQUENCE LISTING

<160> NUMBER OF SEQ ID NOS: 101

<210> SEQ ID NO 1
<211> LENGTH: 1461
<212> TYPE: DNA
<213> ORGANISM: Staphylococcus bacteriophage 2638A

<400> SEQUENCE: 1

```
atgctaactg ctattgacta tcttacgaaa aaaggttgga aaatatcatc tgaccctcgc      60
```

```
acttacgatg gttaccctaa aaactacggc tacagaaatt accatgaaaa cggcattaat    120
tatgatgagt tttgtggtgg ttatcataga gcttttgatg tttacagtaa cgaaactaac    180
gacgtgcctg ctgttactag cggaacagtt attgaagcaa acgattacgg taattttggt    240
ggtacattcg ttattagaga cgctaacgat aacgattgga tatatgggca tctacaacgt    300
ggctcaatgc gatttgttgt aggcgacaaa gtcaatcaag gtgacattat tggtttacaa    360
ggtaatagca actattacga caatcctatg agtgtacatt acatttaca attacgccct     420 aaagacgcaa agaaagatga aaatcacaa gtatgtagtg gtttggctat ggaaaaatat     480
gacattacaa atttaaatgc taaacaagat aaatcaaaga atgggagcgt gaaagagttg    540
aaacatatct attcaaacca tattaaaggt aacaagatta cagcaccaaa acctagtatt    600
caaggtgtgg tcatccacaa tgattatggt agtatgacac ctagtcaata cttaccatgg    660
ttatatgcac gtgagaataa cggtacacac gttaacggtt gggctagtgt ttatgcaaat    720
agaaacgaag tgctttggta tcatccgaca gactacgtag agtggcattg tggtaatcaa    780
tgggcaaatg ctaacttaat cggatttgaa gtgtgtgagt cgtatcctgg tagaatctcg    840
gacaaattat tcttagaaaa tgaagaagcg acattgaaag tagctgcgga tgtgatgaag    900
tcgtacggat taccagttaa tcgcaacact gtacgtctgc ataacgaatt cttcggaact    960
tcttgtccac atcgttcgtg ggacttgcat gttggcaaag gtgagcctta cacaactact   1020
aatattaata aaatgaaaga ctacttcatc aaacgcatca acattatta tgacggtgga    1080 aagctagaag taagcaaagc agcaactatc aaacaatctg acgttaagca agaagttaaa   1140
aagcaagaag caaacaaat tgtgaaagca acagattgga aacagaataa agatggcatt    1200
tggtataaag ctgaacatgc ttcgttcaca gtgacagcac cagagggaat tatcacaaga   1260
tacaaaggtc cttggactgg tcacccacaa gctggtgtat acaaaaagg tcaaacgatt    1320 aaatatgatg aggttcaaaa atttgacggt catgtttggg tatcgtggga aacgtttgag   1380
ggcgaaactg tatacatgcc ggtacgcaca tgggacgcta aaactggtaa agttggtaag   1440
ttgtggggcg aaattaaata a                                              1461
```

<210> SEQ ID NO 2
<211> LENGTH: 486
<212> TYPE: PRT
<213> ORGANISM: Staphylococcus bacteriophage 2638A

<400> SEQUENCE: 2

Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
        35                  40                  45

His Arg Ala Phe Asp Val Tyr Ser Asn Glu Thr Asn Asp Val Pro Ala
    50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Asn Asp Trp Ile Tyr Gly
                85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125

```
Pro Met Ser Val His Leu His Leu Gln Leu Arg Pro Lys Asp Ala Lys
    130                 135                 140

Lys Asp Glu Lys Ser Gln Val Cys Ser Gly Leu Ala Met Glu Lys Tyr
145                 150                 155                 160

Asp Ile Thr Asn Leu Asn Ala Lys Gln Asp Lys Ser Lys Asn Gly Ser
                165                 170                 175

Val Lys Glu Leu Lys His Ile Tyr Ser Asn His Ile Lys Gly Asn Lys
                180                 185                 190

Ile Thr Ala Pro Lys Pro Ser Ile Gln Gly Val Val Ile His Asn Asp
            195                 200                 205

Tyr Gly Ser Met Thr Pro Ser Gln Tyr Leu Pro Trp Leu Tyr Ala Arg
    210                 215                 220

Glu Asn Asn Gly Thr His Val Asn Gly Trp Ala Ser Val Tyr Ala Asn
225                 230                 235                 240

Arg Asn Glu Val Leu Trp Tyr His Pro Thr Asp Tyr Val Glu Trp His
                245                 250                 255

Cys Gly Asn Gln Trp Ala Asn Ala Asn Leu Ile Gly Phe Glu Val Cys
                260                 265                 270

Glu Ser Tyr Pro Gly Arg Ile Ser Asp Lys Leu Phe Leu Glu Asn Glu
            275                 280                 285

Glu Ala Thr Leu Lys Val Ala Ala Asp Val Met Lys Ser Tyr Gly Leu
    290                 295                 300

Pro Val Asn Arg Asn Thr Val Arg Leu His Asn Glu Phe Phe Gly Thr
305                 310                 315                 320

Ser Cys Pro His Arg Ser Trp Asp Leu His Val Gly Lys Gly Glu Pro
                325                 330                 335

Tyr Thr Thr Thr Asn Ile Asn Lys Met Lys Asp Tyr Phe Ile Lys Arg
                340                 345                 350

Ile Lys His Tyr Tyr Asp Gly Gly Lys Leu Glu Val Ser Lys Ala Ala
            355                 360                 365

Thr Ile Lys Gln Ser Asp Val Lys Gln Glu Val Lys Lys Gln Glu Ala
    370                 375                 380

Lys Gln Ile Val Lys Ala Thr Asp Trp Lys Gln Asn Lys Asp Gly Ile
385                 390                 395                 400

Trp Tyr Lys Ala Glu His Ala Ser Phe Thr Val Thr Ala Pro Glu Gly
                405                 410                 415

Ile Ile Thr Arg Tyr Lys Gly Pro Trp Thr Gly His Pro Gln Ala Gly
                420                 425                 430

Val Leu Gln Lys Gly Gln Thr Ile Lys Tyr Asp Glu Val Gln Lys Phe
    435                 440                 445

Asp Gly His Val Trp Val Ser Trp Glu Thr Phe Glu Gly Glu Thr Val
450                 455                 460

Tyr Met Pro Val Arg Thr Trp Asp Ala Lys Thr Gly Lys Val Gly Lys
465                 470                 475                 480

Leu Trp Gly Glu Ile Lys
                485

<210> SEQ ID NO 3
<211> LENGTH: 279
<212> TYPE: DNA
<213> ORGANISM: Staphylococcus simulans

<400> SEQUENCE: 3
tggaaaacaa acaaatatgg cacactatat aaatcagagt cagctagctt cacacctaat      60
```
acagatataa taacaagaac gactggtcca tttagaagca tgccgcagtc aggagtctta    120
aaagcaggtc aaacaattca ttatgatgaa gtgatgaaac aagacggtca tgtttgggta    180
ggttatacag gtaacagtgg ccaacgtatt tacttgcctg taagaacatg gaataaatct    240
actaatactt taggtgttct ttggggaact ataaagtga                           279

<210> SEQ ID NO 4
<211> LENGTH: 92
<212> TYPE: PRT
<213> ORGANISM: Staphylococcus simulans

<400> SEQUENCE: 4

Trp Lys Thr Asn Lys Tyr Gly Thr Leu Tyr Lys Ser Glu Ser Ala Ser
1               5                   10                  15

Phe Thr Pro Asn Thr Asp Ile Ile Thr Arg Thr Gly Pro Phe Arg
                20                  25                  30

Ser Met Pro Gln Ser Gly Val Leu Lys Ala Gly Gln Thr Ile His Tyr
            35                  40                  45

Asp Glu Val Met Lys Gln Asp Gly His Val Trp Val Gly Tyr Thr Gly
        50                  55                  60

Asn Ser Gly Gln Arg Ile Tyr Leu Pro Val Arg Thr Trp Asn Lys Ser
65                  70                  75                  80

Thr Asn Thr Leu Gly Val Leu Trp Gly Thr Ile Lys
                85                  90

<210> SEQ ID NO 5
<211> LENGTH: 285
<212> TYPE: DNA
<213> ORGANISM: Staphylococcus bacteriophage 2638A

<400> SEQUENCE: 5
tggaaacaga ataaagatgg catttggtat aaagctgaac atgcttcgtt cacagtgaca    60
gcaccagagg gaattatcac aagatacaaa ggtccttgga ctggtcaccc acaagctggt    120
gtattacaaa aaggtcaaac gattaaatat gatgaggttc aaaaatttga cggtcatgtt    180
tgggtatcgt gggaaacgtt tgagggcgaa actgtataca tgccggtacg cacatgggac    240
gctaaaactg gtaaagttgg taagttgtgg ggcgaaatta ataa                     285

<210> SEQ ID NO 6
<211> LENGTH: 94
<212> TYPE: PRT
<213> ORGANISM: Staphylococcus bacteriophage 2638A

<400> SEQUENCE: 6

Trp Lys Gln Asn Lys Asp Gly Ile Trp Tyr Lys Ala Glu His Ala Ser
1               5                   10                  15

Phe Thr Val Thr Ala Pro Glu Gly Ile Ile Thr Arg Tyr Lys Gly Pro
                20                  25                  30

Trp Thr Gly His Pro Gln Ala Gly Val Leu Gln Lys Gly Gln Thr Ile
            35                  40                  45

Lys Tyr Asp Glu Val Gln Lys Phe Asp Gly His Val Trp Val Ser Trp
        50                  55                  60

Glu Thr Phe Glu Gly Glu Thr Val Tyr Met Pro Val Arg Thr Trp Asp
65                  70                  75                  80

Ala Lys Thr Gly Lys Val Gly Lys Leu Trp Gly Glu Ile Lys
                85                  90

<210> SEQ ID NO 7
<211> LENGTH: 282
<212> TYPE: DNA
<213> ORGANISM: Staphylococcus bacteriophage phiNM3

<400> SEQUENCE: 7

```
ggtaaatctg caagtaaaat aacagttgga agtaaagcgc cttataacct taaatggtca      60
aaaggtgctt attttaatgc gaaaatcgac ggcttaggtg ctacttcagc cactagatac     120
ggtgataatc gtactaacta tagattcgat gttggacagg ctgtatacgc gcctggaaca     180
ttaatatatg tgtttgaaat tatagatggt tggtgtcgca tttattggaa caatcataat     240
gagtggatat ggcatgagag attgattgtg aagaagtgt tt                         282
```

<210> SEQ ID NO 8
<211> LENGTH: 94
<212> TYPE: PRT
<213> ORGANISM: Staphylococcus bacteriophage phiNM3

<400> SEQUENCE: 8

```
Gly Lys Ser Ala Ser Lys Ile Thr Val Gly Ser Lys Ala Pro Tyr Asn
1               5                   10                  15

Leu Lys Trp Ser Lys Gly Ala Tyr Phe Asn Ala Lys Ile Asp Gly Leu
            20                  25                  30

Gly Ala Thr Ser Ala Thr Arg Tyr Gly Asp Asn Arg Thr Asn Tyr Arg
        35                  40                  45

Phe Asp Val Gly Gln Ala Val Tyr Ala Pro Gly Thr Leu Ile Tyr Val
    50                  55                  60

Phe Glu Ile Ile Asp Gly Trp Cys Arg Ile Tyr Trp Asn Asn His Asn
65                  70                  75                  80

Glu Trp Ile Trp His Glu Arg Leu Ile Val Lys Glu Val Phe
                85                  90
```

<210> SEQ ID NO 9
<211> LENGTH: 585
<212> TYPE: DNA
<213> ORGANISM: Staphylococcus bacteriophage K

<400> SEQUENCE: 9

```
atggctaaga ctcaagcaga aataaataaa cgtttagatg cttatgcaaa aggaacagta      60
gatagccctt acagagttaa aaaagctaca agttatgacc catcatttgg tgtaatggaa     120
gcaggagcca ttgatgcaga tggttactat cacgctcagt gtcaagacct tattacagac     180
tatgttttat ggttaacaga taataaagtt agaacttggg gtaatgctaa agaccaaatt     240
aaacagagtt atggtactgg atttaaaata catgaaaata aaccttctac tgtacctaaa     300
aaaggttgga ttgcggtatt tacatccggt agttatgaac agtggggtca cataggtatt     360
gtatatgatg gagtaatac ttctacattt actattttag cagcaaactg gaatggttat      420
gctaataaaa aacctacaaa acgtgtagat aattattacg gattaactca cttcattgaa     480
atacctgtaa aagcaggaac tactgttaaa aagaaacag ctaagaaaag cgcaagtaaa     540
acgcctgcac taaaaagaa agcaacacta aagtttcta agaat                      585
```

<210> SEQ ID NO 10
<211> LENGTH: 195
<212> TYPE: PRT
<213> ORGANISM: Staphylococcus bacteriophage K

<400> SEQUENCE: 10

Met Ala Lys Thr Gln Ala Glu Ile Asn Lys Arg Leu Asp Tyr Ala
1               5                   10                  15

Lys Gly Thr Val Asp Ser Pro Tyr Arg Val Lys Lys Ala Thr Ser Tyr
                20                  25                  30

Asp Pro Ser Phe Gly Val Met Glu Ala Gly Ala Ile Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
                100                 105                 110

Glu Gln Trp Gly His Ile Gly Ile Val Tyr Asp Gly Gly Asn Thr Ser
            115                 120                 125

Thr Phe Thr Ile Leu Glu Gln Asn Trp Asn Gly Tyr Ala Asn Lys Lys
        130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Lys Ala Thr Leu Lys Val
                180                 185                 190

Ser Lys Asn
        195

<210> SEQ ID NO 11
<211> LENGTH: 420
<212> TYPE: DNA
<213> ORGANISM: Staphylococcus bacteriophage Twort

<400> SEQUENCE: 11
atgaaaaccc tgaaacaagc agagtcctac attaagagta agtaaatac aggaactgat    60 tttgatggtt tatatgggta tcagtgtatg gacttagcag tagattatat ttaccatgta    120
acagatggta aaataagaat gtggggtaat gctaaggatg cgataaataa ctcttttggt    180
ggtactgcta cggtatataa aaactaccct gcttttagac ctaagtacgg tgatgtagtc    240
gtatggacta ctggtaattt tgcaacttat ggtcatatcg caatagttac taaccctgac    300
ccttatggag accttcaata tgttacagtt cttgaacaaa actggaacgg taacgggatt    360
tataaaaccg agttagctac aatcagaaca cacgattaca caggaattac acattttatt    420

<210> SEQ ID NO 12
<211> LENGTH: 140
<212> TYPE: PRT
<213> ORGANISM: Staphylococcus bacteriophage Twort

<400> SEQUENCE: 12

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
                20                  25                  30

Ala Val Asp Tyr Ile Tyr His Val Thr Asp Gly Lys Ile Arg Met Trp
            35                  40                  45

```
Gly Asn Ala Lys Asp Ala Ile Asn Asn Ser Phe Gly Gly Thr Ala Thr
        50                  55                  60

Val Tyr Lys Asn Tyr Pro Ala Phe Arg Pro Lys Tyr Gly Asp Val Val
 65                  70                  75                  80

Val Trp Thr Thr Gly Asn Phe Ala Thr Tyr Gly His Ile Ala Ile Val
                 85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile
        130                 135                 140

<210> SEQ ID NO 13
<211> LENGTH: 438
<212> TYPE: DNA
<213> ORGANISM: Staphylococcus bacteriophage 2638A

<400> SEQUENCE: 13
atgctaactg ctattgacta tcttacgaaa aaaggttgga aaatatcatc tgaccctcgc      60
acttacgatg gttaccctaa aaactacggc tacagaaatt accatgaaaa cggcattaat     120
tatgatgagt tttgtggtgg ttatcataga gcttttgatg tttacagtaa cgaaactaac     180
gacgtgcctg ctgttactag cggaacagtt attgaagcaa acgattacgg taattttggt     240
ggtacattcg ttattagaga cgctaacgat aacgattgga tatatgggca tctacaacgt     300
ggctcaatgc gatttgttgt aggcgacaaa gtcaatcaag gtgacattat tggtttacaa     360
ggtaatagca actattacga caatcctatg agtgtacatt tacatttaca attacgccct     420
aaagacgcaa agaaagat                                                   438

<210> SEQ ID NO 14
<211> LENGTH: 146
<212> TYPE: PRT
<213> ORGANISM: Staphylococcus bacteriophage 2638A

<400> SEQUENCE: 14

Met Leu Thr Ala Ile Asp Tyr Leu Thr Lys Lys Gly Trp Lys Ile Ser
 1                5                  10                  15

Ser Asp Pro Arg Thr Tyr Asp Gly Tyr Pro Lys Asn Tyr Gly Tyr Arg
                 20                  25                  30

Asn Tyr His Glu Asn Gly Ile Asn Tyr Asp Glu Phe Cys Gly Gly Tyr
            35                  40                  45

His Arg Ala Phe Asp Val Tyr Ser Asn Glu Thr Asn Asp Val Pro Ala
 50                  55                  60

Val Thr Ser Gly Thr Val Ile Glu Ala Asn Asp Tyr Gly Asn Phe Gly
 65                  70                  75                  80

Gly Thr Phe Val Ile Arg Asp Ala Asn Asp Asn Asp Trp Ile Tyr Gly
                 85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125

Pro Met Ser Val His Leu His Leu Gln Leu Arg Pro Lys Asp Ala Lys
        130                 135                 140

Lys Asp
145
```

<210> SEQ ID NO 15
<211> LENGTH: 420
<212> TYPE: DNA
<213> ORGANISM: Staphylococcus simulans

<400> SEQUENCE: 15

```
gctgcaacac atgaacattc agcacaatgg ttgaataatt acaaaaaagg atatggttac      60
ggtccttatc cattaggtat aaatggcggt atgcactacg gagttgattt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca agaatggttt     360
aattcatttt caaattcaac tgcccaagat ccaatgcctt tcttaaagag cgcaggatat     420
```

<210> SEQ ID NO 16
<211> LENGTH: 140
<212> TYPE: PRT
<213> ORGANISM: Staphylococcus simulans

<400> SEQUENCE: 16

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr
    130                 135                 140
```

<210> SEQ ID NO 17
<211> LENGTH: 510
<212> TYPE: DNA
<213> ORGANISM: Staphylococcus bacteriophage 2638A

<400> SEQUENCE: 17

```
ggtaacaaga ttacagcacc aaaacctagt attcaaggtg tggtcatcca caatgattat      60
ggtagtatga cacctagtca atacttacca tggttatatg cacgtgagaa taacggtaca     120
cacgttaacg gttgggctag tgtttatgca aatagaaacg aagtgctttg gtatcatccg     180
acagactacg tagagtggca ttgtggtaat caatgggcaa atgctaactt aatcggattt     240
gaagtgtgtg agtcgtatcc tggtagaatc tcggacaaat tattcttaga aaatgaagaa     300
gcgacattga agtagctgc ggatgtgatg aagtcgtacg gattaccagt taatcgcaac     360
actgtacgtc tgcataacga attcttcgga acttcttgtc cacatcgttc gtgggacttg     420
```

```
catgttggca aaggtgagcc ttacacaact actaatatta ataaaatgaa agactacttc     480
atcaaacgca tcaaacatta ttatgacggt                                     510
```

<210> SEQ ID NO 18
<211> LENGTH: 169
<212> TYPE: PRT
<213> ORGANISM: Staphylococcus bacteriophage 2638A

<400> SEQUENCE: 18

```
Asn Lys Ile Thr Ala Pro Lys Pro Ser Ile Gln Gly Val Val Ile His
1               5                   10                  15

Asn Asp Tyr Gly Ser Met Thr Pro Ser Gln Tyr Leu Pro Trp Leu Tyr
            20                  25                  30

Ala Arg Glu Asn Asn Gly Thr His Val Asn Gly Trp Ala Ser Val Tyr
        35                  40                  45

Ala Asn Arg Asn Glu Val Leu Trp Tyr His Pro Thr Asp Tyr Val Glu
    50                  55                  60

Trp His Cys Gly Asn Gln Trp Ala Asn Ala Asn Leu Ile Gly Phe Glu
65                  70                  75                  80

Val Cys Glu Ser Tyr Pro Gly Arg Ile Ser Asp Lys Leu Phe Leu Glu
                85                  90                  95

Asn Glu Glu Ala Thr Leu Lys Val Ala Ala Asp Val Met Lys Ser Tyr
            100                 105                 110

Gly Leu Pro Val Asn Arg Asn Thr Val Arg Leu His Asn Glu Phe Phe
        115                 120                 125

Gly Thr Ser Cys Pro His Arg Ser Trp Asp Leu His Val Gly Lys Gly
    130                 135                 140

Glu Pro Tyr Thr Thr Thr Asn Ile Asn Lys Met Lys Asp Tyr Phe Ile
145                 150                 155                 160

Lys Arg Ile Lys His Tyr Tyr Asp Gly
                165
```

<210> SEQ ID NO 19
<211> LENGTH: 1407
<212> TYPE: DNA
<213> ORGANISM: artificial
<220> FEATURE:
<223> OTHER INFORMATION: artificial construct

<400> SEQUENCE: 19

```
atggctaaga ctcaagcaga aataaataaa cgtttagatg cttatgcaaa aggaacagta      60
gatagccctt acagagttaa aaaagctaca agttatgacc catcatttgg tgtaatggaa     120
gcaggagcca ttgatgcaga tggttactat cacgctcagt gtcaagacct tattacagac     180
tatgttttat ggttaacaga taataaagtt agaacttggg gtaatgctaa agaccaaatt     240
aaacagagtt atggtactgg atttaaaata catgaaaata aaccttctac tgtacctaaa     300
aaaggttgga ttgcggtatt tacatccggt agttatgaac agtggggtca cataggtatt     360
gtatatgatg gaggtaatac ttctacattt actatttag  agcaaaactg aatggttat     420 gctaataaaa aacctacaaa acgtgtagat aattattacg gattaactca cttcattgaa     480
atacctgtaa aagcaggaac tactgttaaa aagaaacag ctaagaaaag cgcaagtaaa     540
acgcctgcac ctaaaaagaa agcaacacta aagtttcta agaatgagct catggctaag     600
actcaagcag aaataaataa acgtttagat gcttatgcaa aggaacagt agatagccct     660 tacagagtta aaaaagctac aagttatgac ccatcatttg gtgtaatgga agcaggagcc     720
```

-continued

```
attgatgcag atggttacta tcacgctcag tgtcaagacc ttattacaga ctatgtttta    780
tggttaacag ataataaagt tagaacttgg ggtaatgcta agaccaaat taaacagagt     840 tatggtactg gatttaaaat acatgaaaat aaaccttcta ctgtacctaa aaaaggttgg    900
attgcggtat ttcatccgg tagttatgaa cagtggggtc acataggtat tgtatatgat    960
ggaggtaata cttctacatt tactatttta gagcaaaact ggaatggtta tgctaataaa   1020
aaacctacaa aacgtgtaga taattattac ggattaactc acttcattga atacctgta   1080 aaagcaggaa aagcaggtgg tacagtaact ccaacgccga atacaggttg aaaacaaac   1140 aaatatggca cactatataa atcagagtca gctagcttca cacctaatac agatataata   1200
acaagaacga ctggtccatt tagaagcatg ccgcagtcag gagtcttaaa agcaggtcaa   1260
acaattcatt atgatgaagt gatgaaacaa gacggtcatg tttgggtagg ttatacaggt   1320
aacagtggcc aacgtattta cttgcctgta agaacatgga ataaatctac taatactttta  1380 ggtgttcttt ggggaactat aaagtaa                                       1407
```

<210> SEQ ID NO 20
<211> LENGTH: 468
<212> TYPE: PRT
<213> ORGANISM: artificial
<220> FEATURE:
<223> OTHER INFORMATION: artificial construct

<400> SEQUENCE: 20

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
                100                 105                 110

Glu Gln Trp Gly His Ile Gly Ile Val Tyr Asp Gly Gly Asn Thr Ser
            115                 120                 125

Thr Phe Thr Ile Leu Glu Gln Asn Trp Asn Gly Tyr Ala Asn Lys Lys
        130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn Glu Leu Met Ala Lys Thr Gln Ala Glu Ile Asn Lys Arg
        195                 200                 205

Leu Asp Ala Tyr Ala Lys Gly Thr Val Asp Ser Pro Tyr Arg Val Lys
    210                 215                 220

Lys Ala Thr Ser Tyr Asp Pro Ser Phe Gly Val Met Glu Ala Gly Ala
225                 230                 235                 240
```

Ile Asp Ala Asp Gly Tyr Tyr His Ala Gln Cys Gln Asp Leu Ile Thr
            245                 250                 255

Asp Tyr Val Leu Trp Leu Thr Asp Asn Lys Val Arg Thr Trp Gly Asn
        260                 265                 270

Ala Lys Asp Gln Ile Lys Gln Ser Tyr Gly Thr Gly Phe Lys Ile His
    275                 280                 285

Glu Asn Lys Pro Ser Thr Val Pro Lys Lys Gly Trp Ile Ala Val Phe
290                 295                 300

Thr Ser Gly Ser Tyr Glu Gln Trp Gly His Ile Gly Ile Val Tyr Asp
305                 310                 315                 320

Gly Gly Asn Thr Ser Thr Phe Thr Ile Leu Glu Gln Asn Trp Asn Gly
                325                 330                 335

Tyr Ala Asn Lys Lys Pro Thr Lys Arg Val Asp Asn Tyr Tyr Gly Leu
            340                 345                 350

Thr His Phe Ile Glu Ile Pro Val Lys Ala Gly Lys Ala Gly Gly Thr
        355                 360                 365

Val Thr Pro Thr Pro Asn Thr Gly Trp Lys Thr Asn Lys Tyr Gly Thr
    370                 375                 380

Leu Tyr Lys Ser Glu Ser Ala Ser Phe Thr Pro Asn Thr Asp Ile Ile
385                 390                 395                 400

Thr Arg Thr Thr Gly Pro Phe Arg Ser Met Pro Gln Ser Gly Val Leu
                405                 410                 415

Lys Ala Gly Gln Thr Ile His Tyr Asp Glu Val Met Lys Gln Asp Gly
            420                 425                 430

His Val Trp Val Gly Tyr Thr Gly Asn Ser Gly Gln Arg Ile Tyr Leu
        435                 440                 445

Pro Val Arg Thr Trp Asn Lys Ser Thr Asn Thr Leu Gly Val Leu Trp
    450                 455                 460

Gly Thr Ile Lys
465

<210> SEQ ID NO 21
<211> LENGTH: 1209
<212> TYPE: DNA
<213> ORGANISM: artificial
<220> FEATURE:
<223> OTHER INFORMATION: artificial construct

<400> SEQUENCE: 21
gctgcaacac atgaacattc agcacaatgg ttgaataatt acaaaaaagg atatggttac      60
ggtccttatc cattaggtat aaatggcggt atgcactacg gagttgattt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca agaatggtt     360 aattcatttt caaattcaac tgcccaagat ccaatgcctt tcttaaagag cgcaggatat     420
ggaaaagcag gtggtacagt aactccaacg ccgaatacag tgagctcgc tgcaacacat     480 gaacattcag cacaatggtt gaataattac aaaaaggat atggttacgg tccttatcca     540
ttaggtataa atggcggtat gcactacgga gttgattttt tatgaatat tggaacacca     600 gtaaaagcta tttcaagcgg aaaaatagtt gaagctggtt ggagtaatta cggaggaggt     660
aatcaaatag gtcttattga aaatgatgga gtgcatagac aatggtatat gcatctaagt     720

-continued

```
aaatataatg ttaaagtagg agattatgtc aaagctggtc aaataatcgg ttggtctgga      780
agcactggtt attctacagc accacattta cacttccaaa gaatggttaa ttcatttca       840 aattcaactg cccaagatcc aatgccttc ttaaagagcg caggatatgg aaaagcaggt       900
ggtacagtaa ctccaacgcc aatacaggt tggaaaacaa acaaatatgg cacactatat      960
aaatcagagt cagctagctt cacacctaat acagatataa taacaagaac gactggtcca    1020
tttagaagca tgccgcagtc aggagtctta aaagcaggtc aaacaattca ttatgatgaa    1080
gtgatgaaac aagacggtca tgtttgggta ggttatacag taacagtgg ccaacgtatt     1140 tacttgcctg taagaacatg gaataaatct actaatactt taggtgttct ttggggaact    1200
ataaagtaa                                                              1209
```

<210> SEQ ID NO 22
<211> LENGTH: 402
<212> TYPE: PRT
<213> ORGANISM: artificial
<220> FEATURE:
<223> OTHER INFORMATION: artificial construct

<400> SEQUENCE: 22

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Glu Leu Ala Ala Thr His
145                 150                 155                 160

Glu His Ser Ala Gln Trp Leu Asn Asn Tyr Lys Lys Gly Tyr Gly Tyr
                165                 170                 175

Gly Pro Tyr Pro Leu Gly Ile Asn Gly Gly Met His Tyr Gly Val Asp
            180                 185                 190

Phe Phe Met Asn Ile Gly Thr Pro Val Lys Ala Ile Ser Ser Gly Lys
        195                 200                 205

Ile Val Glu Ala Gly Trp Ser Asn Tyr Gly Gly Asn Gln Ile Gly
    210                 215                 220

Leu Ile Glu Asn Asp Gly Val His Arg Gln Trp Tyr Met His Leu Ser
225                 230                 235                 240

Lys Tyr Asn Val Lys Val Gly Asp Tyr Val Lys Ala Gly Gln Ile Ile
                245                 250                 255

Gly Trp Ser Gly Ser Thr Gly Tyr Ser Thr Ala Pro His Leu His Phe
            260                 265                 270
```

```
Gln Arg Met Val Asn Ser Phe Ser Asn Ser Thr Ala Gln Asp Pro Met
        275                 280                 285
Pro Phe Leu Lys Ser Ala Gly Tyr Gly Lys Ala Gly Gly Thr Val Thr
    290                 295                 300
Pro Thr Pro Asn Thr Gly Trp Lys Thr Asn Lys Tyr Gly Thr Leu Tyr
305                 310                 315                 320
Lys Ser Glu Ser Ala Ser Phe Thr Pro Asn Thr Asp Ile Ile Thr Arg
                325                 330                 335
Thr Thr Gly Pro Phe Arg Ser Met Pro Gln Ser Gly Val Leu Lys Ala
            340                 345                 350
Gly Gln Thr Ile His Tyr Asp Glu Val Met Lys Gln Asp Gly His Val
        355                 360                 365
Trp Val Gly Tyr Thr Gly Asn Ser Gly Gln Arg Ile Tyr Leu Pro Val
    370                 375                 380
Arg Thr Trp Asn Lys Ser Thr Asn Thr Leu Gly Val Leu Trp Gly Thr
385                 390                 395                 400
Ile Lys

<210> SEQ ID NO 23
<211> LENGTH: 1686
<212> TYPE: DNA
<213> ORGANISM: artificial
<220> FEATURE:
<223> OTHER INFORMATION: artificial construct

<400> SEQUENCE: 23
gcaaagaaag atgaaaaatc acaagtatgt agtggtttgg ctatggaaaa atatgacatt      60
acaaatttaa atgctaaaca agataaatca agaatgggga gcgtgaaaga gttgaaacat     120
atctattcaa accatattaa aggtaacaag attacagcac aaaacctag tattcaaggt      180
gtggtcatcc acaatgatta tggtagtatg acacctagtc aatacttacc atggttatat     240
gcacgtgaga ataacggtac acacgttaac ggttgggcta gtgtttatgc aaatagaaac     300
gaagtgcttt ggtatcatcc gacagactac gtagagtggc attgtggtaa tcaatgggca     360
aatgctaact taatcggatt tgaagtgtgt gagtcgtatc ctggtagaat ctcggacaaa     420
ttattcttag aaaatgaaga agcgacattg aaagtagctg cggatgtgat gaagtcgtac     480
ggattaccag ttaatcgcaa cactgtacgt ctgcataacg aattcttcgg aacttcttgt     540
ccacatcgtt cgtgggactt gcatgttggc aaaggtgagc cttacacaac tactaatatt     600
aataaaatga agactactt catcaaacgc atcaaacatt attatgacgg tgagctcgca     660
aagaaagatg aaaaatcaca agtatgtagt ggtttggcta tggaaaaata tgacattaca     720
aatttaaatg ctaaacaaga taatcaaag aatgggagcg tgaaagagtt gaaacatatc     780
tattcaaacc atattaaagg taacaagatt acagcaccaa aacctagtat tcaaggtgtg     840
gtcatccaca atgattatgg tagtatgaca cctagtcaat acttaccatg gttatatgca     900
cgtgagaata acggtacaca cgttaacggt tgggctagtg tttatgcaaa tagaaacgaa     960
gtgctttggt atcatccgac agactacgta gagtggcatt gtggtaatca atgggcaaat    1020
gctaacttaa tcggatttga agtgtgtgag tcgtatcctg gtagaatctc ggacaaatta    1080
ttcttagaaa atgaagaagc gacattgaaa gtagctgcgg atgtgatgaa gtcgtacgga    1140
ttaccagtta atcgcaacac tgtacgtctg cataacgaat tcttcggaac ttcttgtcca    1200
catcgttcgt gggacttgca tgttggcaaa ggtgagcctt acacaactac taatattaat    1260
```

-continued

```
aaaatgaaag actacttcat caaacgcatc aaacattatt atgacggtgg aaagctagaa    1320
gtaagcaaag cagcaactat caaacaatct gacgttaagc aagaagttaa aaagcaagaa    1380
gcaaaacaaa ttgtgaaagc aacagattgg aaaacaaaca aatatggcac actatataaa    1440
tcagagtcag ctagcttcac acctaataca gatataataa caagaacgac tggtccattt    1500
agaagcatgc cgcagtcagg agtcttaaaa gcaggtcaaa caattcatta tgatgaagtg    1560
atgaaacaag acggtcatgt ttgggtaggt tatacaggta acagtggcca acgtatttac    1620
ttgcctgtaa aacatggaa taaatctact aatactttag gtgttctttg gggaactata    1680
aagtaa                                                              1686
```

<210> SEQ ID NO 24
<211> LENGTH: 561
<212> TYPE: PRT
<213> ORGANISM: artificial
<220> FEATURE:
<223> OTHER INFORMATION: artificial construct

<400> SEQUENCE: 24

```
Ala Lys Lys Asp Glu Lys Ser Gln Val Cys Ser Gly Leu Ala Met Glu
1               5                  10                  15

Lys Tyr Asp Ile Thr Asn Leu Asn Ala Lys Gln Asp Lys Ser Lys Asn
            20                  25                  30

Gly Ser Val Lys Glu Leu Lys His Ile Tyr Ser Asn His Ile Lys Gly
        35                  40                  45

Asn Lys Ile Thr Ala Pro Lys Pro Ser Ile Gln Gly Val Val Ile His
    50                  55                  60

Asn Asp Tyr Gly Ser Met Thr Pro Ser Gln Tyr Leu Pro Trp Leu Tyr
65                  70                  75                  80

Ala Arg Glu Asn Asn Gly Thr His Val Asn Gly Trp Ala Ser Val Tyr
                85                  90                  95

Ala Asn Arg Asn Glu Val Leu Trp Tyr His Pro Thr Asp Tyr Val Glu
            100                 105                 110

Trp His Cys Gly Asn Gln Trp Ala Asn Ala Asn Leu Ile Gly Phe Glu
        115                 120                 125

Val Cys Glu Ser Tyr Pro Gly Arg Ile Ser Asp Lys Leu Phe Leu Glu
    130                 135                 140

Asn Glu Glu Ala Thr Leu Lys Val Ala Ala Asp Val Met Lys Ser Tyr
145                 150                 155                 160

Gly Leu Pro Val Asn Arg Asn Thr Val Arg Leu His Asn Glu Phe Phe
                165                 170                 175

Gly Thr Ser Cys Pro His Arg Ser Trp Asp Leu His Val Gly Lys Gly
            180                 185                 190

Glu Pro Tyr Thr Thr Thr Asn Ile Asn Lys Met Lys Asp Tyr Phe Ile
        195                 200                 205

Lys Arg Ile Lys His Tyr Tyr Asp Gly Glu Leu Ala Lys Lys Asp Glu
    210                 215                 220

Lys Ser Gln Val Cys Ser Gly Leu Ala Met Glu Lys Tyr Asp Ile Thr
225                 230                 235                 240

Asn Leu Asn Ala Lys Gln Asp Lys Ser Lys Asn Gly Ser Val Lys Glu
                245                 250                 255

Leu Lys His Ile Tyr Ser Asn His Ile Lys Gly Asn Lys Ile Thr Ala
            260                 265                 270

Pro Lys Pro Ser Ile Gln Gly Val Val Ile His Asn Asp Tyr Gly Ser
        275                 280                 285
```

Met Thr Pro Ser Gln Tyr Leu Pro Trp Leu Tyr Ala Arg Glu Asn Asn
290                 295                 300

Gly Thr His Val Asn Gly Trp Ala Ser Val Tyr Ala Asn Arg Asn Glu
305                 310                 315                 320

Val Leu Trp Tyr His Pro Thr Asp Tyr Val Glu Trp His Cys Gly Asn
                325                 330                 335

Gln Trp Ala Asn Ala Asn Leu Ile Gly Phe Glu Val Cys Glu Ser Tyr
                340                 345                 350

Pro Gly Arg Ile Ser Asp Lys Leu Phe Leu Glu Asn Glu Glu Ala Thr
                355                 360                 365

Leu Lys Val Ala Ala Asp Val Met Lys Ser Tyr Gly Leu Pro Val Asn
370                 375                 380

Arg Asn Thr Val Arg Leu His Asn Glu Phe Phe Gly Thr Ser Cys Pro
385                 390                 395                 400

His Arg Ser Trp Asp Leu His Val Gly Lys Gly Glu Pro Tyr Thr Thr
                405                 410                 415

Thr Asn Ile Asn Lys Met Lys Asp Tyr Phe Ile Lys Arg Ile Lys His
                420                 425                 430

Tyr Tyr Asp Gly Gly Lys Leu Glu Val Ser Lys Ala Ala Thr Ile Lys
                435                 440                 445

Gln Ser Asp Val Lys Gln Glu Val Lys Gln Glu Ala Lys Gln Ile
450                 455                 460

Val Lys Ala Thr Asp Trp Lys Thr Asn Lys Tyr Gly Thr Leu Tyr Lys
465                 470                 475                 480

Ser Glu Ser Ala Ser Phe Thr Pro Asn Thr Asp Ile Ile Thr Arg Thr
                485                 490                 495

Thr Gly Pro Phe Arg Ser Met Pro Gln Ser Gly Val Leu Lys Ala Gly
                500                 505                 510

Gln Thr Ile His Tyr Asp Glu Val Met Lys Gln Asp Gly His Val Trp
                515                 520                 525

Val Gly Tyr Thr Gly Asn Ser Gly Gln Arg Ile Tyr Leu Pro Val Arg
530                 535                 540

Thr Trp Asn Lys Ser Thr Asn Thr Leu Gly Val Leu Trp Gly Thr Ile
545                 550                 555                 560

Lys

<210> SEQ ID NO 25
<211> LENGTH: 1131
<212> TYPE: DNA
<213> ORGANISM: artificial
<220> FEATURE:
<223> OTHER INFORMATION: artificial construct

<400> SEQUENCE: 25
atgagaggat cgcatcacca tcaccatcac ggatctggct ctggatctgg tatcgaggga     60
aggccttata tggaactgga tccgcatgc gagctcgcaa agaaagatga aaatcacaa     120 gtatgtagtg gtttggctat ggaaaaatat gacattacaa atttaaatgc taaacaagat    180
aaatcaaaga atgggagcgt gaaagagttg aaacatatct attcaaacca tattaaaggt    240
aacaagatta cagcaccaaa acctagtatt caaggtgtgg tcatccacaa tgattatggt    300
agtatgacac tagtcaata cttaccatgg ttatatgcac gtgagaataa cggtacacac    360
gttaacggtt gggctagtgt ttatgcaaat agaaacgaag tgctttggta tcatccgaca    420
gactacgtag agtggcattg tggtaatcaa tgggcaaatg ctaacttaat cggatttgaa    480

-continued

```
gtgtgtgagt cgtatcctgg tagaatctcg gacaaattat tcttagaaaa tgaagaagcg      540
acattgaaag tagctgcgga tgtgatgaag tcgtacggat taccagttaa tcgcaacact      600
gtacgtctgc ataacgaatt cttcggaact tcttgtccac atcgttcgtg ggacttgcat      660
gttggcaaag gtgagcctta cacaactact aatattaata aaatgaaaga ctacttcatc      720
aaacgcatca acattatta tgacggtgga aagctagaag taagcaaagc agcaactatc       780
aaacaatctg acgttaagca agaagttaaa aagcaagaag caaaacaaat tgtgaaagca      840
acagattgga aacagaataa agatggcatt tggtataaag ctgaacatgc ttcgttcaca      900
gtgacagcac cagagggaat tatcacaaga tacaaaggtc cttggactgg tcacccacaa      960
gctggtgtat tacaaaaagg tcaaacgatt aaatatgatg aggttcaaaa atttgacggt     1020
catgtttggg tatcgtggga aacgtttgag ggcgaaactg tatacatgcc ggtacgcaca     1080
tgggacgcta aaactggtaa agttggtaag ttgtggggcg aaattaaata a              1131
```

<210> SEQ ID NO 26
<211> LENGTH: 376
<212> TYPE: PRT
<213> ORGANISM: artificial
<220> FEATURE:
<223> OTHER INFORMATION: artificial construct

<400> SEQUENCE: 26

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95

Asn Asp Tyr Gly Ser Met Thr Pro Ser Gln Tyr Leu Pro Trp Leu Tyr
            100                 105                 110

Ala Arg Glu Asn Asn Gly Thr His Val Asn Gly Trp Ala Ser Val Tyr
        115                 120                 125

Ala Asn Arg Asn Glu Val Leu Trp Tyr His Pro Thr Asp Tyr Val Glu
    130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
                165                 170                 175

Asn Glu Glu Ala Thr Leu Lys Val Ala Ala Asp Val Met Lys Ser Tyr
            180                 185                 190

Gly Leu Pro Val Asn Arg Asn Thr Val Arg Leu His Asn Glu Phe Phe
        195                 200                 205

Gly Thr Ser Cys Pro His Arg Ser Trp Asp Leu His Val Gly Lys Gly
    210                 215                 220

Glu Pro Tyr Thr Thr Thr Asn Ile Asn Lys Met Lys Asp Tyr Phe Ile
225                 230                 235                 240

Lys Arg Ile Lys His Tyr Tyr Asp Gly Gly Lys Leu Glu Val Ser Lys
```

```
                245                 250                 255
Ala Ala Thr Ile Lys Gln Ser Asp Val Lys Gln Glu Val Lys Lys Gln
        260                 265                 270

Glu Ala Lys Gln Ile Val Lys Ala Thr Asp Trp Lys Gln Asn Lys Asp
    275                 280                 285

Gly Ile Trp Tyr Lys Ala Glu His Ala Ser Phe Thr Val Thr Ala Pro
    290                 295                 300

Glu Gly Ile Ile Thr Arg Tyr Lys Gly Pro Trp Thr Gly His Pro Gln
305                 310                 315                 320

Ala Gly Val Leu Gln Lys Gly Gln Thr Ile Lys Tyr Asp Glu Val Gln
            325                 330                 335

Lys Phe Asp Gly His Val Trp Val Ser Trp Glu Thr Phe Glu Gly Glu
                340                 345                 350

Thr Val Tyr Met Pro Val Arg Thr Trp Asp Ala Lys Thr Gly Lys Val
            355                 360                 365

Gly Lys Leu Trp Gly Glu Ile Lys
    370                 375

<210> SEQ ID NO 27
<211> LENGTH: 1125
<212> TYPE: DNA
<213> ORGANISM: artificial
<220> FEATURE:
<223> OTHER INFORMATION: artificial construct

<400> SEQUENCE: 27
atgagaggat cgcatcacca tcaccatcac ggatctggct ctggatctgg tatcgaggga      60 aggcccttata atggaactgg atccgcatgc gagctcgcaa agaaagatga aaaatcacaa    120
gtatgtagtg gtttggctat ggaaaaatat gacattacaa atttaaatgc taaacaagat    180
aaatcaaaga atgggagcgt gaaagagttg aaacatatct attcaaacca tattaaaggt    240
aacaagatta cagcaccaaa acctagtatt caaggtgtgg tcatccacaa tgattatggt    300
agtatgacac ctagtcaata cttaccatgg ttatatgcac gtgagaataa cggtacacac    360
gttaacggtt gggctagtgt ttatgcaaat agaaacgaag tgcttttggta tcatccgaca    420 gactacgtag agtggcattg tggtaatcaa tgggcaaatg ctaacttaat cggatttgaa    480
gtgtgtgagt cgtatcctgg tagaatctcg gacaaattat tcttagaaaa tgaagaagcg    540
acattgaaag tagctgcgga tgtgatgaag tcgtacggat taccagttaa tcgcaacact    600
gtacgtctgc ataacgaatt cttcggaact tcttgtccac atcgttcgtg ggacttgcat    660
gttggcaaag gtgagcctta cacaactact aatattaata aaatgaaaga ctacttcatc    720
aaacgcatca acattatta tgacggtgga agtctagaag taagcaaagc agcaactatc    780
aaacaatctg acgttaagca agaagttaaa agcaagaag caaaacaaat tgtgaaagca    840
acagattgga aaacaaacaa atatggcaca ctatataaat cagagtcagc tagcttcaca    900
cctaatacag atataataac aagaacgact ggtccattta gaagcatgcc gcagtcagga    960
gtcttaaaag caggtcaaac aattcattat gatgaagtga tgaaacaaga cggtcatgtt   1020
tgggtaggtt atacaggtaa cagtggccaa cgtatttact tgcctgtaag aacatggaat   1080
aaatctacta atactttagg tgttctttgg ggaactataa agtaa                    1125

<210> SEQ ID NO 28
<211> LENGTH: 374
<212> TYPE: PRT
<213> ORGANISM: artificial
```

<220> FEATURE:
<223> OTHER INFORMATION: artificial construct

<400> SEQUENCE: 28

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95

Asn Asp Tyr Gly Ser Met Thr Pro Ser Gln Tyr Leu Pro Trp Leu Tyr
            100                 105                 110

Ala Arg Glu Asn Asn Gly Thr His Val Asn Gly Trp Ala Ser Val Tyr
        115                 120                 125

Ala Asn Arg Asn Glu Val Leu Trp Tyr His Pro Thr Asp Tyr Val Glu
    130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
                165                 170                 175

Asn Glu Glu Ala Thr Leu Lys Val Ala Ala Asp Val Met Lys Ser Tyr
            180                 185                 190

Gly Leu Pro Val Asn Arg Asn Thr Val Arg Leu His Asn Glu Phe Phe
        195                 200                 205

Gly Thr Ser Cys Pro His Arg Ser Trp Asp Leu His Val Gly Lys Gly
    210                 215                 220

Glu Pro Tyr Thr Thr Thr Asn Ile Asn Lys Met Lys Asp Tyr Phe Ile
225                 230                 235                 240

Lys Arg Ile Lys His Tyr Tyr Asp Gly Gly Lys Leu Glu Val Ser Lys
                245                 250                 255

Ala Ala Thr Ile Lys Gln Ser Asp Val Lys Gln Glu Val Lys Lys Gln
            260                 265                 270

Glu Ala Lys Gln Ile Val Lys Ala Thr Asp Trp Lys Thr Asn Lys Tyr
        275                 280                 285

Gly Thr Leu Tyr Lys Ser Glu Ser Ala Ser Phe Thr Pro Asn Thr Asp
    290                 295                 300

Ile Ile Thr Arg Thr Thr Gly Pro Phe Arg Ser Met Pro Gln Ser Gly
305                 310                 315                 320

Val Leu Lys Ala Gly Gln Thr Ile His Tyr Asp Glu Val Met Lys Gln
                325                 330                 335

Asp Gly His Val Trp Val Gly Tyr Thr Gly Asn Ser Gly Gln Arg Ile
            340                 345                 350

Tyr Leu Pro Val Arg Thr Trp Asn Lys Ser Thr Asn Thr Leu Gly Val
        355                 360                 365

Leu Trp Gly Thr Ile Lys
    370

<210> SEQ ID NO 29

<211> LENGTH: 1131
<212> TYPE: DNA
<213> ORGANISM: artificial
<220> FEATURE:
<223> OTHER INFORMATION: artificial construct

<400> SEQUENCE: 29

```
atgagaggat cgcatcacca tcaccatcac ggatctggct ctggatctgg tatcgaggga      60
aggcettata tggaactgg atccgcatgc gagctcgcaa agaaagatga aaatcacaa       120
gtatgtagtg gtttggctat ggaaaaatat gacattacaa atttaaatgc taaacaagat    180
aaatcaaaga atgggagcgt gaaagagttg aaacatatct attcaaacca tattaaaggt   240
aacaagatta cagcaccaaa acctagtatt caaggtgtgg tcatccacaa tgattatggt   300
agtatgacac ctagtcaata cttaccatgg ttatatgcac gtgagaataa cggtacacac   360
gttaacggtt gggctagtgt ttatgcaaat agaaacgaag tgctttggta tcatccgaca   420
gactacgtag agtggcattg tggtaatcaa tgggcaaatg ctaacttaat cggatttgaa   480
gtgtgtgagt cgtatcctgg tagaatctcg gacaaattat tcttagaaaa tgaagaagcg   540
acattgaaag tagctgcgga tgtgatgaag tcgtacggat taccagttaa tcgcaacact   600
gtacgtctgc ataacgaatt cttcggaact tcttgtccac atcgttcgtg ggacttgcat   660
gttggcaaag gtgagcctta cacaactact aatattaata aaatgaaaga ctacttcatc   720
aaacgcatca acattatta tgacggtgga agctagaaa taagcaaagc agcaactatc    780
aaacaatctg acgttaagca agaagttaaa aagcaagaag caaaacaaat tgtgaaagca   840
acagatggta aatctgcaag taaaataaca gttggaagta agcgcctta taaccttaaa    900
tggtcaaaag gtgcttattt taatgcgaaa atcgacggct taggtgctac ttcagccact   960
agatacggtg ataatcgtac taactataga ttcgatgttg gacaggctgt atacgcgcct  1020
ggaacattaa tatatgtgtt tgaaattata gatggttggt gtcgcattta ttggaacaat  1080
cataatgagt ggatatggca tgagagattg attgtgaaag aagtgtttta a           1131
```

<210> SEQ ID NO 30
<211> LENGTH: 376
<212> TYPE: PRT
<213> ORGANISM: artificial
<220> FEATURE:
<223> OTHER INFORMATION: artificial construct

<400> SEQUENCE: 30

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Lys Lys Asp Glu Lys Ser Gln Val Cys Ser Gly Leu Ala Met Glu
        35                  40                  45

Lys Tyr Asp Ile Thr Asn Leu Asn Ala Lys Gln Asp Lys Ser Lys Asn
    50                  55                  60

Gly Ser Val Lys Glu Leu Lys His Ile Tyr Ser Asn His Ile Lys Gly
65                  70                  75                  80

Asn Lys Ile Thr Ala Pro Lys Pro Ser Ile Gln Gly Val Val Ile His
                85                  90                  95

Asn Asp Tyr Gly Ser Met Thr Pro Ser Gln Tyr Leu Pro Trp Leu Tyr
            100                 105                 110

Ala Arg Glu Asn Asn Gly Thr His Val Asn Gly Trp Ala Ser Val Tyr
        115                 120                 125
```

Ala Asn Arg Asn Glu Val Leu Trp Tyr His Pro Thr Asp Tyr Val Glu
    130                 135                 140

Trp His Cys Gly Asn Gln Trp Ala Asn Ala Asn Leu Ile Gly Phe Glu
145                 150                 155                 160

Val Cys Glu Ser Tyr Pro Gly Arg Ile Ser Asp Lys Leu Phe Leu Glu
            165                 170                 175

Asn Glu Glu Ala Thr Leu Lys Val Ala Ala Asp Val Met Lys Ser Tyr
        180                 185                 190

Gly Leu Pro Val Asn Arg Asn Thr Val Arg Leu His Asn Glu Phe Phe
    195                 200                 205

Gly Thr Ser Cys Pro His Arg Ser Trp Asp Leu His Val Gly Lys Gly
    210                 215                 220

Glu Pro Tyr Thr Thr Thr Asn Ile Asn Lys Met Lys Asp Tyr Phe Ile
225                 230                 235                 240

Lys Arg Ile Lys His Tyr Tyr Asp Gly Gly Lys Leu Glu Val Ser Lys
            245                 250                 255

Ala Ala Thr Ile Lys Gln Ser Asp Val Lys Gln Glu Val Lys Lys Gln
        260                 265                 270

Glu Ala Lys Gln Ile Val Lys Ala Thr Asp Gly Lys Ser Ala Ser Lys
    275                 280                 285

Ile Thr Val Gly Ser Lys Ala Pro Tyr Asn Leu Lys Trp Ser Lys Gly
    290                 295                 300

Ala Tyr Phe Asn Ala Lys Ile Asp Gly Leu Gly Ala Thr Ser Ala Thr
305                 310                 315                 320

Arg Tyr Gly Asp Asn Arg Thr Asn Tyr Arg Phe Asp Val Gly Gln Ala
            325                 330                 335

Val Tyr Ala Pro Gly Thr Leu Ile Tyr Val Phe Glu Ile Ile Asp Gly
        340                 345                 350

Trp Cys Arg Ile Tyr Trp Asn Asn His Asn Glu Trp Ile Trp His Glu
    355                 360                 365

Arg Leu Ile Val Lys Glu Val Phe
    370                 375

<210> SEQ ID NO 31
<211> LENGTH: 975
<212> TYPE: DNA
<213> ORGANISM: artificial
<220> FEATURE:
<223> OTHER INFORMATION: artificial construct

<400> SEQUENCE: 31
atgagaggat cgcatcacca tcaccatcac ggatctggct ctggatctgg tatcgaggga     60
aggccttata tggaactgga tccgcatgc gagctcatgg ctaagactca agcagaaata    120
aataaacgtt tagatgctta tgcaaaagga acagtagata gcccttacag agttaaaaaa    180
gctacaagtt atgacccatc atttggtgta atggaagcag gagccattga tgcagatggt    240
tactatcacg ctcagtgtca agaccttatt acagactatg ttttatggtt aacagataat    300
aaagttagaa cttggggtaa tgctaaagac caaattaaac agagttatgg tactggattt    360
aaaatacatg aaaataaacc ttctactgta cctaaaaaag gttggattgc ggtatttaca    420
tccggtagtt atgaacagtg gggtcacata ggtattgtat atgatggagg taatacttct    480
acatttacta ttttagagca aaactggaat ggttatgcta ataaaaaacc tacaaaacgt    540
gtagataatt attacggatt aactcacttc attgaaatac ctgtaaaagc aggaaagcta    600

```
gaagtaagca aagcagcaac tatcaaacaa tctgacgtta agcaagaagt taaaaagcaa      660
gaagcaaaac aaattgtgaa agcaacagat tggaaacaga ataaagatgg catttggtat      720
aaagctgaac atgcttcgtt cacagtgaca gcaccagagg gaattatcac aagatacaaa      780
ggtccttgga ctggtcaccc acaagctggt gtattacaaa aaggtcaaac gattaaatat      840
gatgaggttc aaaaatttga cggtcatgtt tgggtatcgt gggaaacgtt tgagggcgaa      900
actgtataca tgccggtacg cacatgggac gctaaaactg gtaaagttgg taagttgtgg      960
ggcgaaatta aataa                                                      975
```

<210> SEQ ID NO 32
<211> LENGTH: 324
<212> TYPE: PRT
<213> ORGANISM: artificial
<220> FEATURE:
<223> OTHER INFORMATION: artificial construct

<400> SEQUENCE: 32

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Ala Lys Thr Gln Ala Glu Ile Asn Lys Arg Leu Asp Ala Tyr Ala
        35                  40                  45

Lys Gly Thr Val Asp Ser Pro Tyr Arg Val Lys Ala Thr Ser Tyr
    50                  55                  60

Asp Pro Ser Phe Gly Val Met Glu Ala Gly Ala Ile Asp Ala Asp Gly
65                  70                  75                  80

Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
            100                 105                 110

Lys Gln Ser Tyr Gly Thr Gly Phe Lys Ile His Glu Asn Lys Pro Ser
        115                 120                 125

Thr Val Pro Lys Lys Gly Trp Ile Ala Val Phe Thr Ser Gly Ser Tyr
    130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Lys Leu Glu Val Ser Lys Ala Ala Thr Ile
        195                 200                 205

Lys Gln Ser Asp Val Lys Gln Glu Val Lys Gln Glu Ala Lys Gln
    210                 215                 220

Ile Val Lys Ala Thr Asp Trp Lys Gln Asn Lys Asp Gly Ile Trp Tyr
225                 230                 235                 240

Lys Ala Glu His Ala Ser Phe Thr Val Thr Ala Pro Glu Gly Ile Ile
                245                 250                 255

Thr Arg Tyr Lys Gly Pro Trp Thr Gly His Pro Gln Ala Gly Val Leu
            260                 265                 270

Gln Lys Gly Gln Thr Ile Lys Tyr Asp Glu Val Gln Lys Phe Asp Gly
        275                 280                 285

His Val Trp Val Ser Trp Glu Thr Phe Glu Gly Glu Thr Val Tyr Met
```

```
                290                 295                 300
Pro Val Arg Thr Trp Asp Ala Lys Thr Gly Lys Val Gly Lys Leu Trp
305                 310                 315                 320

Gly Glu Ile Lys

<210> SEQ ID NO 33
<211> LENGTH: 912
<212> TYPE: DNA
<213> ORGANISM: artificial
<220> FEATURE:
<223> OTHER INFORMATION: artificial construct

<400> SEQUENCE: 33
atgagaggat cgcatcacca tcaccatcac ggatctggct ctggatctgg tatcgaggga      60
aggccttata tggaactgg atccgcatgc gagctcatgg ctaagactca agcagaaata     120
aataaacgtt tagatgctta tgcaaaagga acagtagata gcccttacag agttaaaaaa     180
gctacaagtt atgacccatc atttggtgta atggaagcag gagccattga tgcagatggt     240
tactatcacg ctcagtgtca agaccttatt acagactatg ttttatggtt aacagataat     300
aaagttagaa cttggggtaa tgctaaagac caaattaaac agagttatgg tactggatt     360
aaaatacatg aaaataaacc ttctactgta cctaaaaaag gttggattgc ggtatttaca     420
tccggtagtt atgaacagtg gggtcacata ggtattgtat atgatggagg taatacttct     480
acatttacta ttttagagca aaactggaat ggttatgcta ataaaaaacc tacaaaacgt     540
gtagataatt attacggatt aactcacttc attgaaatac ctgtaaaagc aggaaaagca     600
ggtggtacag taactccaac gccgaataca ggttggaaaa caaacaaata tggcacacta     660
tataaatcag agtcagctag cttcacacct aatacagata ataataacaag aacgactggt     720
ccatttagaa gcatgccgca gtcaggagtc ttaaaagcag gtcaaacaat tcattatgat     780
gaagtgatga acaagacgg tcatgtttgg gtaggttata caggtaacag tggccaacgt     840
atttacttgc ctgtaagaac atggaataaa tctactaata ctttaggtgt tctttgggga     900
actataaagt aa                                                        912

<210> SEQ ID NO 34
<211> LENGTH: 303
<212> TYPE: PRT
<213> ORGANISM: artificial
<220> FEATURE:
<223> OTHER INFORMATION: artificial construct

<400> SEQUENCE: 34

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Ala Lys Thr Gln Ala Glu Ile Asn Lys Arg Leu Asp Ala Tyr Ala
        35                  40                  45

Lys Gly Thr Val Asp Ser Pro Tyr Arg Val Lys Lys Ala Thr Ser Tyr
    50                  55                  60

Asp Pro Ser Phe Gly Val Met Glu Ala Gly Ala Ile Asp Ala Asp Gly
65                  70                  75                  80

Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
            100                 105                 110
```

```
Lys Gln Ser Tyr Gly Thr Gly Phe Lys Ile His Glu Asn Lys Pro Ser
            115                 120                 125

Thr Val Pro Lys Lys Gly Trp Ile Ala Val Phe Thr Ser Gly Ser Tyr
        130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Lys Ala Gly Gly Thr Val Thr Pro Thr Pro
        195                 200                 205

Asn Thr Gly Trp Lys Thr Asn Lys Tyr Gly Thr Leu Tyr Lys Ser Glu
    210                 215                 220

Ser Ala Ser Phe Thr Pro Asn Thr Asp Ile Ile Thr Arg Thr Thr Gly
225                 230                 235                 240

Pro Phe Arg Ser Met Pro Gln Ser Gly Val Leu Lys Ala Gly Gln Thr
                245                 250                 255

Ile His Tyr Asp Glu Val Met Lys Gln Asp Gly His Val Trp Val Gly
            260                 265                 270

Tyr Thr Gly Asn Ser Gly Gln Arg Ile Tyr Leu Pro Val Arg Thr Trp
        275                 280                 285

Asn Lys Ser Thr Asn Thr Leu Gly Val Leu Trp Gly Thr Ile Lys
    290                 295                 300

<210> SEQ ID NO 35
<211> LENGTH: 966
<212> TYPE: DNA
<213> ORGANISM: artificial
<220> FEATURE:
<223> OTHER INFORMATION: artificial construct

<400> SEQUENCE: 35
atgagaggat cgcatcacca tcaccatcac ggatctggct ctggatctgg tatcgaggga    60
aggccttata tggaactgga tccgcatgcg agctcatggc taagactcaa gcagaaata   120 aataaacgtt tagatgctta tgcaaaagga acagtagata gcccttacag agttaaaaaa   180
gctacaagtt atgacccatc atttggtgta atggaagcag gagccattga tgcagatggt   240
tactatcacg ctcagtgtca agaccttatt acagactatg ttttatggtt aacagataat   300
aaagttagaa cttggggtaa tgctaaagac caaattaaac agagttatgg tactggattt   360
aaaatacatg aaaataaacc ttctactgta cctaaaaaag gttggattgc ggtatttaca   420
tccggtagtt atgaacagtg gggtcacata ggtattgtat atgatggagg taatacttct   480
acatttacta ttttagagca aaactggaat ggttatgcta ataaaaaacc tacaaaacgt   540
gtagataatt attacggatt aactcacttc attgaaatac ctgtaaaagc aggaactact   600
gttaaaaaag aaacagctaa gaaaagcgca gtaaaacgc ctgcacctaa aagaaagca   660 acactaaaag tttctaagaa tggtaaatct gcaagtaaaa taacagttgg aagtaaagcg   720
ccttataacc ttaaatggtc aaaaggtgct tattttaatg cgaaaatcga cggcttaggt   780
gctacttcag ccactagata cggtgataat cgtactaact atagattcga tgttggacag   840
gctgtatacg cgcctggaac attaatatat gtgtttgaaa ttatagatgg ttggtgtcgc   900
atttattgga caatcataa tgagtggata tggcatgaga gattgattgt gaaagaagtg   960
```

-continued ttttaa 966

<210> SEQ ID NO 36
<211> LENGTH: 321
<212> TYPE: PRT
<213> ORGANISM: artificial
<220> FEATURE:
<223> OTHER INFORMATION: artificial construct

<400> SEQUENCE: 36

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Ala Lys Thr Gln Ala Glu Ile Asn Lys Arg Leu Asp Ala Tyr Ala
        35                  40                  45

Lys Gly Thr Val Asp Ser Pro Tyr Arg Val Lys Ala Thr Ser Tyr
    50                  55                  60

Asp Pro Ser Phe Gly Val Met Glu Ala Gly Ala Ile Asp Ala Asp Gly
65                  70                  75                  80

Tyr Tyr His Ala Gln Cys Gln Asp Leu Ile Thr Asp Tyr Val Leu Trp
                85                  90                  95

Leu Thr Asp Asn Lys Val Arg Thr Trp Gly Asn Ala Lys Asp Gln Ile
            100                 105                 110

Lys Gln Ser Tyr Gly Thr Gly Phe Lys Ile His Glu Asn Lys Pro Ser
        115                 120                 125

Thr Val Pro Lys Lys Gly Trp Ile Ala Val Phe Thr Ser Gly Ser Tyr
130                 135                 140

Glu Gln Trp Gly His Ile Gly Ile Val Tyr Asp Gly Gly Asn Thr Ser
145                 150                 155                 160

Thr Phe Thr Ile Leu Glu Gln Asn Trp Asn Gly Tyr Ala Asn Lys Lys
                165                 170                 175

Pro Thr Lys Arg Val Asp Asn Tyr Tyr Gly Leu Thr His Phe Ile Glu
            180                 185                 190

Ile Pro Val Lys Ala Gly Thr Thr Val Lys Lys Glu Thr Ala Lys Lys
        195                 200                 205

Ser Ala Ser Lys Thr Pro Ala Pro Lys Lys Ala Thr Leu Lys Val
    210                 215                 220

Ser Lys Asn Gly Lys Ser Ala Ser Lys Ile Thr Val Gly Ser Lys Ala
225                 230                 235                 240

Pro Tyr Asn Leu Lys Trp Ser Lys Gly Ala Tyr Phe Asn Ala Lys Ile
                245                 250                 255

Asp Gly Leu Gly Ala Thr Ser Ala Thr Arg Tyr Gly Asp Asn Arg Thr
            260                 265                 270

Asn Tyr Arg Phe Asp Val Gly Gln Ala Val Tyr Ala Pro Gly Thr Leu
        275                 280                 285

Ile Tyr Val Phe Glu Ile Ile Asp Gly Trp Cys Arg Ile Tyr Trp Asn
    290                 295                 300

Asn His Asn Glu Trp Ile Trp His Glu Arg Leu Ile Val Lys Glu Val
305                 310                 315                 320

Phe

<210> SEQ ID NO 37
<211> LENGTH: 927
<212> TYPE: DNA
<213> ORGANISM: artificial

<220> FEATURE:
<223> OTHER INFORMATION: artificial construct

<400> SEQUENCE: 37

```
atgagaggat cgcatcacca tcaccatcac ggatctggct ctggatctgg tatcgaggga      60
aggcccttata tggaactgg atccgcatgc gagctcatga aaaccctgaa acaagcagag     120
tcctacatta agagtaaagt aaatacagga actgattttg atggtttata tgggtatcag    180
tgtatggact tagcagtaga ttatatttac catgtaacag atggtaaaat aagaatgtgg    240
ggtaatgcta aggatgcgat aaataactct tttggtggta ctgctacggt atataaaaac   300
taccctgctt ttagacctaa gtacggtgat gtagtcgtat ggactactgg taattttgca   360
acttatggtc atatcgcaat agttactaac cctgacccct atggagacct tcaatatgtt   420
acagttcttg aacaaaactg gaacggtaac gggatttata aaaccgagtt agctacaatc   480
agaacacacg attacacagg aattacacat tttattagac ctaactttgc tactgaatca   540
agtgtaaaaa agaaagatac aaagaaaaaa ccaaaaccat caaatagaga tggaataaat   600
aaagataaaa ttgtatatga tagaactaat attaattaca attggaaaca gaataaagat   660
ggcatttggt ataaagctga acatgcttcg ttcacagtga cagcaccaga gggaattatc   720
acaagataca aggtcccttg gactggtcac ccacaagctg gtgtattaca aaaaggtcaa   780
acgattaaat atgatgaggt tcaaaaattt gacggtcatg tttgggtatc gtgggaaacg   840
tttgagggcg aaactgtata catgccggta cgcacatggg acgctaaaac tggtaaagtt   900
ggtaagttgt ggggcgaaat taaataa                                       927
```

<210> SEQ ID NO 38
<211> LENGTH: 308
<212> TYPE: PRT
<213> ORGANISM: artificial
<220> FEATURE:
<223> OTHER INFORMATION: artificial construct

<400> SEQUENCE: 38

```
Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Lys Thr Leu Lys Gln Ala Glu Ser Tyr Ile Lys Ser Lys Val Asn
        35                  40                  45

Thr Gly Thr Asp Phe Asp Gly Leu Tyr Gly Tyr Gln Cys Met Asp Leu
    50                  55                  60

Ala Val Asp Tyr Ile Tyr His Val Thr Asp Gly Lys Ile Arg Met Trp
65                  70                  75                  80

Gly Asn Ala Lys Asp Ala Ile Asn Asn Ser Phe Gly Gly Thr Ala Thr
                85                  90                  95

Val Tyr Lys Asn Tyr Pro Ala Phe Arg Pro Lys Tyr Gly Asp Val Val
            100                 105                 110

Val Trp Thr Thr Gly Asn Phe Ala Thr Tyr Gly His Ile Ala Ile Val
        115                 120                 125

Thr Asn Pro Asp Pro Tyr Gly Asp Leu Gln Tyr Val Thr Val Leu Glu
    130                 135                 140

Gln Asn Trp Asn Gly Asn Gly Ile Tyr Lys Thr Glu Leu Ala Thr Ile
145                 150                 155                 160

Arg Thr His Asp Tyr Thr Gly Ile Thr His Phe Ile Arg Pro Asn Phe
                165                 170                 175
```

Ala Thr Glu Ser Ser Val Lys Lys Asp Thr Lys Lys Pro Lys
            180                 185                 190

Pro Ser Asn Arg Asp Gly Ile Asn Lys Asp Lys Ile Val Tyr Asp Arg
            195                 200                 205

Thr Asn Ile Asn Tyr Asn Trp Lys Gln Asn Lys Asp Gly Ile Trp Tyr
    210                 215                 220

Lys Ala Glu His Ala Ser Phe Thr Val Thr Ala Pro Glu Gly Ile Ile
225                 230                 235                 240

Thr Arg Tyr Lys Gly Pro Trp Thr Gly His Pro Gln Ala Gly Val Leu
                245                 250                 255

Gln Lys Gly Gln Thr Ile Lys Tyr Asp Glu Val Gln Lys Phe Asp Gly
            260                 265                 270

His Val Trp Val Ser Trp Glu Thr Phe Glu Gly Glu Thr Val Tyr Met
            275                 280                 285

Pro Val Arg Thr Trp Asp Ala Lys Thr Gly Val Gly Lys Leu Trp
            290                 295                 300

Gly Glu Ile Lys
305

<210> SEQ ID NO 39
<211> LENGTH: 921
<212> TYPE: DNA
<213> ORGANISM: artificial
<220> FEATURE:
<223> OTHER INFORMATION: artificial construct

<400> SEQUENCE: 39
atgagaggat cgcatcacca tcaccatcac ggatctggct ctggatctgg tatcgaggga      60
aggccttata tggaactgga tccgcatgc gagctcatga aaaccctgaa acaagcagag     120
tcctacatta gagtaaagt aaatacagga actgattttg atggtttata tgggtatcag     180
tgtatggact tagcagtaga ttatatttac catgtaacag atggtaaaat aagaatgtgg    240
ggtaatgcta aggatgcgat aaataactct tttggtggta ctgctacggt atataaaaac    300
taccctgctt ttagacctaa gtacggtgat gtagtcgtat ggactactgg taattttgca   360
acttatggtc atatcgcaat agttactaac cctgacccct atggagacct tcaatatgtt   420
acagttcttg aacaaaactg gaacggtaac gggatttata aaaccgagtt agctacaatc   480
agaacacacg attacacagg aattacacat tttattagac taactttgc tactgaatca   540
agtgtaaaaa agaaagatac aaagaaaaaa ccaaaaccat caaatagaga tggaataaat    600
aaagataaaa ttgtatatga tagaactaat attaattaca attggaaaac aaacaaatat    660
ggcacactat ataatcaga gtcagctagc ttcacaccta atacagatat aataacaaga    720
acgactggtc catttagaag catgccgcag tcaggagtct aaaaagcagg tcaaacaatt   780
cattatgatg aagtgatgaa acaagacggt catgtttggg taggttatac aggtaacagt    840
ggccaacgta tttacttgcc tgtaagaaca tggaataaat ctactaatac tttaggtgtt   900
ctttggggaa ctataaagta a                                              921

<210> SEQ ID NO 40
<211> LENGTH: 306
<212> TYPE: PRT
<213> ORGANISM: artificial
<220> FEATURE:
<223> OTHER INFORMATION: artificial construct

<400> SEQUENCE: 40

```
Met Arg Gly Ser His His His His His His Gly Ser Gly Ser Gly Ser
1               5                   10                  15
Gly Ile Glu Gly Arg Pro Tyr Asn Gly Thr Gly Ser Ala Cys Glu Leu
                20                  25                  30
Met Lys Thr Leu Lys Gln Ala Glu Ser Tyr Ile Lys Ser Lys Val Asn
            35                  40                  45
Thr Gly Thr Asp Phe Asp Gly Leu Tyr Gly Tyr Gln Cys Met Asp Leu
        50                  55                  60
Ala Val Asp Tyr Ile Tyr His Val Thr Asp Gly Lys Ile Arg Met Trp
65                  70                  75                  80
Gly Asn Ala Lys Asp Ala Ile Asn Asn Ser Phe Gly Thr Ala Thr
                85                  90                  95
Val Tyr Lys Asn Tyr Pro Ala Phe Arg Pro Lys Tyr Gly Asp Val Val
                100                 105                 110
Val Trp Thr Thr Gly Asn Phe Ala Thr Tyr Gly His Ile Ala Ile Val
            115                 120                 125
Thr Asn Pro Asp Pro Tyr Gly Asp Leu Gln Tyr Val Thr Val Leu Glu
        130                 135                 140
Gln Asn Trp Asn Gly Asn Gly Ile Tyr Lys Thr Glu Leu Ala Thr Ile
145                 150                 155                 160
Arg Thr His Asp Tyr Thr Gly Ile Thr His Phe Ile Arg Pro Asn Phe
                165                 170                 175
Ala Thr Glu Ser Ser Val Lys Lys Lys Asp Thr Lys Lys Pro Lys
                180                 185                 190
Pro Ser Asn Arg Asp Gly Ile Asn Lys Asp Lys Ile Val Tyr Asp Arg
        195                 200                 205
Thr Asn Ile Asn Tyr Asn Trp Lys Thr Asn Lys Tyr Gly Thr Leu Tyr
210                 215                 220
Lys Ser Glu Ser Ala Ser Phe Thr Pro Asn Thr Asp Ile Ile Thr Arg
225                 230                 235                 240
Thr Thr Gly Pro Phe Arg Ser Met Pro Gln Ser Gly Val Leu Lys Ala
                245                 250                 255
Gly Gln Thr Ile His Tyr Asp Glu Val Met Lys Gln Asp Gly His Val
            260                 265                 270
Trp Val Gly Tyr Thr Gly Asn Ser Gly Gln Arg Ile Tyr Leu Pro Val
        275                 280                 285
Arg Thr Trp Asn Lys Ser Thr Asn Thr Leu Gly Val Leu Trp Gly Thr
    290                 295                 300
Ile Lys
305
```

<210> SEQ ID NO 41
<211> LENGTH: 927
<212> TYPE: DNA
<213> ORGANISM: artificial
<220> FEATURE:
<223> OTHER INFORMATION: artificial construct

<400> SEQUENCE: 41

```
atgagaggat cgcatcacca tcaccatcac ggatctggct ctggatctgg tatcgaggga    60 aggcctttata tggaactgg atccgcatgc gagctcatga aaaccctgaa acaagcagag   120
tcctacatta gagtaaagt aaatacagga actgattttg atggtttata tgggtatcag   180
tgtatggact tagcagtaga ttatatttac catgtaacag atggtaaaat aagaatgtgg   240
```

```
ggtaatgcta aggatgcgat aaataactct tttggtggta ctgctacggt atataaaaac    300
taccctgctt ttagacctaa gtacggtgat gtagtcgtat ggactactgg taattttgca    360
acttatggtc atatcgcaat agttactaac cctgacccct atggagacct tcaatatgtt    420
acagttcttg aacaaaactg gaacggtaac gggatttata aaaccgagtt agctacaatc    480
agaacacacg attacacagg aattacacat tttattagac ctaactttgc tactgaatca    540
agtgtaaaaa agaaagatac aaagaaaaaa ccaaaaccat caaatagaga tggaataaat    600
aaagataaaa ttgtatatga tagaactaat attaattaca atggtaaatc tgcaagtaaa    660
ataacagttg gaagtaaagc gccttataac cttaaatggt caaaaggtgc ttattttaat    720
gcgaaaatcg acggcttagg tgctacttca gccactagat acggtgataa tcgtactaac    780
tatagattcg atgttggaca ggctgtatac gcgcctggaa cattaatata tgtgtttgaa    840
attatagatg gttggtgtcg catttattgg aacaatcata atgagtggat atggcatgag    900
agattgattg tgaaagaagt gttttaa                                       927
```

<210> SEQ ID NO 42  
<211> LENGTH: 308  
<212> TYPE: PRT  
<213> ORGANISM: artificial  
<220> FEATURE:  
<223> OTHER INFORMATION: artificial construct

<400> SEQUENCE: 42

```
Met Arg Gly Ser His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Met Lys Thr Leu Lys Gln Ala Glu Ser Tyr Ile Lys Ser Lys Val Asn
        35                  40                  45

Thr Gly Thr Asp Phe Asp Gly Leu Tyr Gly Tyr Gln Cys Met Asp Leu
    50                  55                  60

Ala Val Asp Tyr Ile Tyr His Val Thr Asp Gly Lys Ile Arg Met Trp
65                  70                  75                  80

Gly Asn Ala Lys Asp Ala Ile Asn Asn Ser Phe Gly Thr Ala Thr
                85                  90                  95

Val Tyr Lys Asn Tyr Pro Ala Phe Arg Pro Lys Tyr Gly Asp Val Val
            100                 105                 110

Val Trp Thr Thr Gly Asn Phe Ala Thr Tyr Gly His Ile Ala Ile Val
        115                 120                 125

Thr Asn Pro Asp Pro Tyr Gly Asp Leu Gln Tyr Val Thr Val Leu Glu
    130                 135                 140

Gln Asn Trp Asn Gly Asn Gly Ile Tyr Lys Thr Glu Leu Ala Thr Ile
145                 150                 155                 160

Arg Thr His Asp Tyr Thr Gly Ile Thr His Phe Ile Arg Pro Asn Phe
                165                 170                 175

Ala Thr Glu Ser Ser Val Lys Lys Asp Thr Lys Lys Pro Lys
            180                 185                 190

Pro Ser Asn Arg Asp Gly Ile Asn Lys Asp Lys Ile Val Tyr Asp Arg
        195                 200                 205

Thr Asn Ile Asn Tyr Asn Gly Lys Ser Ala Ser Lys Ile Thr Val Gly
    210                 215                 220

Ser Lys Ala Pro Tyr Asn Leu Lys Trp Ser Lys Gly Ala Tyr Phe Asn
225                 230                 235                 240
```

-continued

```
Ala Lys Ile Asp Gly Leu Gly Ala Thr Ser Ala Thr Arg Tyr Gly Asp
            245                 250                 255

Asn Arg Thr Asn Tyr Arg Phe Asp Val Gly Gln Ala Val Tyr Ala Pro
        260                 265                 270

Gly Thr Leu Ile Tyr Val Phe Glu Ile Ile Asp Gly Trp Cys Arg Ile
    275                 280                 285

Tyr Trp Asn Asn His Asn Glu Trp Ile Trp His Glu Arg Leu Ile Val
290                 295                 300

Lys Glu Val Phe
305
```

<210> SEQ ID NO 43
<211> LENGTH: 843
<212> TYPE: DNA
<213> ORGANISM: artificial
<220> FEATURE:
<223> OTHER INFORMATION: artificial construct

<400> SEQUENCE: 43

```
atgagaggat cgcatcacca tcaccatcac ggatctggct ctggatctgg tatcgaggga    60
aggcccttata tggaactgg atccgcatgc gagctcgctg caacacatga acattcagca   120
caatggttga ataattacaa aaaggatat ggttacggtc cttatccatt aggtataaat    180
ggcggtatgc actacggagt tgatttttt atgaatattg aacaccagt aaaagctatt    240
tcaagcggaa aaatagttga agctggttgg agtaattacg gaggaggtaa tcaaataggt   300
cttattgaaa atgatggagt gcatagacaa tggtatatgc atctaagtaa atataatgtt   360
aaagtaggag attatgtcaa agctggtcaa ataatcggtt ggtctggaag cactggttat   420
tctacagcac cacatttaca cttccaaaga atggttaatt cattttcaaa ttcaactgcc   480
caagatccaa tgcctttctt aaagagcgca ggatatggaa aagcaggtgg tacagtaact   540
ccaacgccga atacaggttg aaacagaat aaagatggca tttggtataa agctgaacat   600
gcttcgttca cagtgacagc accagaggga attatcacaa gatacaaagg tccttggact   660
ggtcacccac aagctggtgt attacaaaaa ggtcaaacga ttaaatatga tgaggttcaa   720
aaatttgacg gtcatgtttg ggtatcgtgg gaaacgtttg agggcgaaac tgtatacatg   780
ccggtacgca catgggacgc taaaactggt aaagttggta agttgtgggg cgaaattaaa   840
taa                                                                 843
```

<210> SEQ ID NO 44
<211> LENGTH: 280
<212> TYPE: PRT
<213> ORGANISM: artificial
<220> FEATURE:
<223> OTHER INFORMATION: artificial construct

<400> SEQUENCE: 44

```
Met Arg Gly Ser His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45

Gly Tyr Gly Tyr Gly Pro Tyr Pro Leu Gly Ile Asn Gly Gly Met His
    50                  55                  60

Tyr Gly Val Asp Phe Phe Met Asn Ile Gly Thr Pro Val Lys Ala Ile
65                  70                  75                  80
```

Ser Ser Gly Lys Ile Val Glu Ala Gly Trp Ser Asn Tyr Gly Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Trp Lys Gln Asn Lys Asp
            180                 185                 190

Gly Ile Trp Tyr Lys Ala Glu His Ala Ser Phe Thr Val Thr Ala Pro
        195                 200                 205

Glu Gly Ile Ile Thr Arg Tyr Lys Gly Pro Trp Thr Gly His Pro Gln
    210                 215                 220

Ala Gly Val Leu Gln Lys Gly Gln Thr Ile Lys Tyr Asp Glu Val Gln
225                 230                 235                 240

Lys Phe Asp Gly His Val Trp Val Ser Trp Glu Thr Phe Glu Gly Glu
                245                 250                 255

Thr Val Tyr Met Pro Val Arg Thr Trp Asp Ala Lys Thr Gly Lys Val
            260                 265                 270

Gly Lys Leu Trp Gly Glu Ile Lys
        275                 280

<210> SEQ ID NO 45
<211> LENGTH: 837
<212> TYPE: DNA
<213> ORGANISM: artificial
<220> FEATURE:
<223> OTHER INFORMATION: artificial construct

<400> SEQUENCE: 45
atgagaggat cgcatcacca tcaccatcac ggatctggct ctggatctgg tatcgaggga      60
aggccttata tggaactgg atccgcatgc gagctcgctg caacacatga acattcagca     120
caatggttga ataattacaa aaaggatat ggttacggtc cttatccatt aggtataaat     180
ggcggtatgc actacggagt tgattttttt atgaatattg aacaccagt aaaagctatt     240 tcaagcggaa aaatagttga agctggttgg agtaattacg gaggaggtaa tcaaataggt     300
cttattgaaa atgatggagt gcatagacaa tggtatatgc atctaagtaa atataatgtt     360
aaagtaggag attatgtcaa agctggtcaa ataatcggtt ggtctggaag cactggttat     420
tctacagcac acatttaca cttccaaaga atggttaatt cattttcaaa ttcaactgcc     480
caagatccaa tgcctttctt aaagagcgca ggatatggaa aagcaggtgg tacagtaact     540
ccaacgccga atacaggttg gaaacaaac aaatatggca cactatataa atcagagtca     600
gctagcttca cacctaatac agatataata acaagaacga ctggtccatt tagaagcatg     660
ccgcagtcag gagtcttaaa agcaggtcaa acaattcatt atgatgaagt gatgaaacaa     720
gacggtcatg tttgggtagg ttatacaggt aacagtggcc aacgtattta cttgcctgta     780
agaacatgga taaatctac taatacttta ggtgttcttt ggggaactat aaagtaa      837

<210> SEQ ID NO 46
<211> LENGTH: 278
<212> TYPE: PRT
<213> ORGANISM: artificial
<220> FEATURE:
<223> OTHER INFORMATION: artificial construct

<400> SEQUENCE: 46

Met Arg Gly Ser His His His His His His Gly Ser Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45

Gly Tyr Gly Tyr Gly Pro Tyr Pro Leu Gly Ile Asn Gly Met His
    50                  55                  60

Tyr Gly Val Asp Phe Phe Met Asn Ile Gly Thr Pro Val Lys Ala Ile
65                  70                  75                  80

Ser Ser Gly Lys Ile Val Glu Ala Gly Trp Ser Asn Tyr Gly Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Trp Lys Thr Asn Lys Tyr
            180                 185                 190

Gly Thr Leu Tyr Lys Ser Glu Ser Ala Ser Phe Thr Pro Asn Thr Asp
        195                 200                 205

Ile Ile Thr Arg Thr Thr Gly Pro Phe Arg Ser Met Pro Gln Ser Gly
    210                 215                 220

Val Leu Lys Ala Gly Gln Thr Ile His Tyr Asp Glu Val Met Lys Gln
225                 230                 235                 240

Asp Gly His Val Trp Val Gly Tyr Thr Gly Asn Ser Gly Gln Arg Ile
                245                 250                 255

Tyr Leu Pro Val Arg Thr Trp Asn Lys Ser Thr Asn Thr Leu Gly Val
            260                 265                 270

Leu Trp Gly Thr Ile Lys
        275

<210> SEQ ID NO 47
<211> LENGTH: 843
<212> TYPE: DNA
<213> ORGANISM: artificial
<220> FEATURE:
<223> OTHER INFORMATION: artificial construct

<400> SEQUENCE: 47
atgagaggat cgcatcacca tcaccatcac ggatctggct ctggatctgg tatcgaggga      60 aggcctta ta atggaactgg atccgcatgc gagctcgctg caacacatga acattcagca    120
caatggttga ataattacaa aaaaggatat ggttacggtc cttatccatt aggtataaat    180

```
ggcggtatgc actacggagt tgatttttt  atgaatattg gaacaccagt aaaagctatt    240
tcaagcggaa aaatagttga agctggttgg agtaattacg gaggaggtaa tcaaataggt    300
cttattgaaa atgatggagt gcatagacaa tggtatatgc atctaagtaa atataatgtt    360
aaagtaggag attatgtcaa agctggtcaa ataatcggtt ggtctggaag cactggttat    420
tctacagcac cacatttaca cttccaaaga atggttaatt catttcaaa  ttcaactgcc    480 caagatccaa tgccttttctt aaagagcgca ggatatggaa aagcaggtgg tacagtaact    540
ccaacgccga atacaggtgg taaatctgca agtaaaataa cagttggaag taaagcgcct    600
tataacctta aatggtcaaa aggtgcttat tttaatgcga aaatcgacgg cttaggtgct    660
acttcagcca ctagatacgg tgataatcgt actaactata gattcgatgt tggacaggct    720
gtatacgcgc tggaacatt  aatatatgtg tttgaaatta tagatggttg gtgtcgcatt    780
tattggaaca atcataatga gtggatatgg catgagagat tgattgtgaa agaagtgttt    840
taa                                                                 843
```

<210> SEQ ID NO 48
<211> LENGTH: 280
<212> TYPE: PRT
<213> ORGANISM: artificial
<220> FEATURE:
<223> OTHER INFORMATION: artificial construct
<400> SEQUENCE: 48

```
Met Arg Gly Ser His His His His His Gly Ser Gly Ser
1               5                   10                  15

Gly Ile Glu Gly Arg Pro Tyr Asn Gly Thr Gly Ser Ala Cys Glu Leu
            20                  25                  30

Ala Ala Thr His Glu His Ser Ala Gln Trp Leu Asn Asn Tyr Lys Lys
        35                  40                  45

Gly Tyr Gly Tyr Gly Pro Tyr Pro Leu Gly Ile Asn Gly Gly Met His
    50                  55                  60

Tyr Gly Val Asp Phe Phe Met Asn Ile Gly Thr Pro Val Lys Ala Ile
65                  70                  75                  80

Ser Ser Gly Lys Ile Val Glu Ala Gly Trp Ser Asn Tyr Gly Gly
                85                  90                  95

Asn Gln Ile Gly Leu Ile Glu Asn Asp Gly Val His Arg Gln Trp Tyr
            100                 105                 110

Met His Leu Ser Lys Tyr Asn Val Lys Val Gly Asp Tyr Val Lys Ala
        115                 120                 125

Gly Gln Ile Ile Gly Trp Ser Gly Ser Thr Gly Tyr Ser Thr Ala Pro
    130                 135                 140

His Leu His Phe Gln Arg Met Val Asn Ser Phe Ser Asn Ser Thr Ala
145                 150                 155                 160

Gln Asp Pro Met Pro Phe Leu Lys Ser Ala Gly Tyr Gly Lys Ala Gly
                165                 170                 175

Gly Thr Val Thr Pro Thr Pro Asn Thr Gly Gly Lys Ser Ala Ser Lys
            180                 185                 190

Ile Thr Val Gly Ser Lys Ala Pro Tyr Asn Leu Lys Trp Ser Lys Gly
        195                 200                 205

Ala Tyr Phe Asn Ala Lys Ile Asp Gly Leu Gly Ala Thr Ser Ala Thr
    210                 215                 220

Arg Tyr Gly Asp Asn Arg Thr Asn Tyr Arg Phe Asp Val Gly Gln Ala
225                 230                 235                 240
```

```
Val Tyr Ala Pro Gly Thr Leu Ile Tyr Val Phe Glu Ile Ile Asp Gly
            245                 250                 255

Trp Cys Arg Ile Tyr Trp Asn Asn His Asn Glu Trp Ile Trp His Glu
        260                 265                 270

Arg Leu Ile Val Lys Glu Val Phe
        275                 280

<210> SEQ ID NO 49
<211> LENGTH: 1755
<212> TYPE: DNA
<213> ORGANISM: artificial
<220> FEATURE:
<223> OTHER INFORMATION: artificial construct

<400> SEQUENCE: 49
atgagaggat cgcatcacca tcaccatcac ggatctggct ctggatctgg tatcgaggga      60
agggcaaaga aagatgaaaa atcacaagta tgtagtggtt tggctatgga aaaatatgac    120
attacaaatt taaatgctaa acaagataaa tcaaagaatg ggagcgtgaa agagttgaaa    180
catatctatt caaaccatat taaaggtaac aagattacag caccaaaacc tagtattcaa    240
ggtgtggtca tccacaatga ttatggtagt atgacaccta gtcaatactt accatggtta    300
tatgcacgtg agaataacgg tacacacgtt aacggttggg ctagtgttta tgcaaataga    360
aacgaagtgc tttggtatca tccgacagac tacgtagagt ggcattgtgg taatcaatgg    420
gcaaatgcta acttaatcgg atttgaagtg tgtgagtcgt atcctggtag aatctcggac    480
aaattattct tagaaaatga agaagcgaca ttgaaagtag ctgcggatgt gatgaagtcg    540
tacggattac cagttaatcg caacactgta cgtctgcata cgaattcttc ggaacttct    600 tgtccacatc gttcgtggga cttgcatgtt ggcaaaggtg agccttacac aactactaat    660
attaataaaa tgaaagacta cttcatcaaa cgcatcaaac attattatga cggtgagctc    720
gcaaagaaag atgaaaaatc acaagtatgt agtggtttgg ctatggaaaa atatgacatt    780
acaaatttaa atgctaaaca agataaatca agaatggga gcgtgaaaga gttgaaacat    840
atctattcaa accatattaa aggtaacaag attacagcac caaaacctag tattcaaggt    900
gtggtcatcc acaatgatta tggtagtatg acacctagtc aatacttacc atggttatat    960
gcacgtgaga ataacggtac acacgttaac ggttgggcta gtgtttatgc aaatagaaac  1020
gaagtgcttt ggtatcatcc gacagactac gtagagtggc attgtggtaa tcaatgggca  1080
aatgctaact taatcggatt tgaagtgtgt gagtcgtatc ctggtagaat ctcggacaaa  1140
ttattcttag aaaatgaaga agcgacattg aaagtagctg cggatgtgat gaagtcgtac  1200
ggattaccag ttaatcgcaa cactgtacgt ctgcataacg aattcttcgg aacttcttgt  1260
ccacatcgtt cgtgggactt gcatgttggc aaaggtgagc cttacacaac tactaatatt  1320
aataaaatga agactactt catcaaacgc atcaaacatt attatgacgg tggaaagcta  1380
gaagtaagca agcagcaac tatcaaacaa tctgacgtta gcaagaagt taaaaagcaa  1440 gaagcaaaac aaattgtgaa agcaacagat tggaaacaga ataagatgg catttggtat  1500 aaagctgaac atgcttcgtt cacagtgaca gcaccagagg gaattatcac aagatacaaa  1560
ggtccttgga ctggtcaccc acaagctggt gtattacaaa aaggtcaaac gattaaatat  1620
gatgaggttc aaaaatttga cggtcatgtt tgggtatcgt gggaaacgtt tgagggcgaa  1680
actgtataca tgccggtacg cacatgggac gctaaaactg gtaaagttgg taagttgtgg  1740
ggcgaaatta aataa                                                  1755
```

```
<210> SEQ ID NO 50
<211> LENGTH: 584
<212> TYPE: PRT
<213> ORGANISM: artificial
<220> FEATURE:
<223> OTHER INFORMATION: artificial construct

<400> SEQUENCE: 50

Met Arg Gly Ser His His His His His His Gly Ser Gly Ser Gly Ser
1               5                   10                  15

Gly Ile Glu Gly Arg Ala Lys Lys Asp Glu Lys Ser Gln Val Cys Ser
            20                  25                  30

Gly Leu Ala Met Glu Lys Tyr Asp Ile Thr Asn Leu Asn Ala Lys Gln
        35                  40                  45

Asp Lys Ser Lys Asn Gly Ser Val Lys Glu Leu Lys His Ile Tyr Ser
    50                  55                  60

Asn His Ile Lys Gly Asn Lys Ile Thr Ala Pro Lys Pro Ser Ile Gln
65                  70                  75                  80

Gly Val Val Ile His Asn Asp Tyr Gly Ser Met Thr Pro Ser Gln Tyr
                85                  90                  95

Leu Pro Trp Leu Tyr Ala Arg Glu Asn Asn Gly Thr His Val Asn Gly
            100                 105                 110

Trp Ala Ser Val Tyr Ala Asn Arg Asn Glu Val Leu Trp Tyr His Pro
        115                 120                 125

Thr Asp Tyr Val Glu Trp His Cys Gly Asn Gln Trp Ala Asn Ala Asn
    130                 135                 140

Leu Ile Gly Phe Glu Val Cys Glu Ser Tyr Pro Gly Arg Ile Ser Asp
145                 150                 155                 160

Lys Leu Phe Leu Glu Asn Glu Glu Ala Thr Leu Lys Val Ala Ala Asp
                165                 170                 175

Val Met Lys Ser Tyr Gly Leu Pro Val Asn Arg Asn Thr Val Arg Leu
            180                 185                 190

His Asn Glu Phe Phe Gly Thr Ser Cys Pro His Arg Ser Trp Asp Leu
        195                 200                 205

His Val Gly Lys Gly Glu Pro Tyr Thr Thr Asn Ile Asn Lys Met
    210                 215                 220

Lys Asp Tyr Phe Ile Lys Arg Ile Lys His Tyr Tyr Asp Gly Glu Leu
225                 230                 235                 240

Ala Lys Lys Asp Glu Lys Ser Gln Val Cys Ser Gly Leu Ala Met Glu
                245                 250                 255

Lys Tyr Asp Ile Thr Asn Leu Asn Ala Lys Gln Asp Lys Ser Lys Asn
            260                 265                 270

Gly Ser Val Lys Glu Leu Lys His Ile Tyr Ser Asn His Ile Lys Gly
        275                 280                 285

Asn Lys Ile Thr Ala Pro Lys Pro Ser Ile Gln Gly Val Val Ile His
    290                 295                 300

Asn Asp Tyr Gly Ser Met Thr Pro Ser Gln Tyr Leu Pro Trp Leu Tyr
305                 310                 315                 320

Ala Arg Glu Asn Asn Gly Thr His Val Asn Gly Trp Ala Ser Val Tyr
                325                 330                 335

Ala Asn Arg Asn Glu Val Leu Trp Tyr His Pro Thr Asp Tyr Val Glu
            340                 345                 350

Trp His Cys Gly Asn Gln Trp Ala Asn Ala Asn Leu Ile Gly Phe Glu
        355                 360                 365
```

| | | | | | | | | | | | |
|---|---|---|---|---|---|---|---|---|---|---|---|
|Val|Cys|Glu|Ser|Tyr|Pro|Gly|Arg|Ile|Ser|Asp|Lys|Leu|Phe|Leu|Glu|
| |370| | | |375| | | |380| | | | | | |

Val Cys Glu Ser Tyr Pro Gly Arg Ile Ser Asp Lys Leu Phe Leu Glu
    370             375             380

Asn Glu Glu Ala Thr Leu Lys Val Ala Ala Asp Val Met Lys Ser Tyr
385             390             395             400

Gly Leu Pro Val Asn Arg Asn Thr Val Arg Leu His Asn Glu Phe Phe
            405             410             415

Gly Thr Ser Cys Pro His Arg Ser Trp Asp Leu His Val Gly Lys Gly
            420             425             430

Glu Pro Tyr Thr Thr Asn Ile Asn Lys Met Lys Asp Tyr Phe Ile
        435             440             445

Lys Arg Ile Lys His Tyr Tyr Asp Gly Gly Lys Leu Glu Val Ser Lys
450             455             460

Ala Ala Thr Ile Lys Gln Ser Asp Val Lys Gln Glu Val Lys Lys Gln
465             470             475             480

Glu Ala Lys Gln Ile Val Lys Ala Thr Asp Trp Lys Gln Asn Lys Asp
            485             490             495

Gly Ile Trp Tyr Lys Ala Glu His Ala Ser Phe Thr Val Thr Ala Pro
        500             505             510

Glu Gly Ile Ile Thr Arg Tyr Lys Gly Pro Trp Thr Gly His Pro Gln
        515             520             525

Ala Gly Val Leu Gln Lys Gly Gln Thr Ile Lys Tyr Asp Glu Val Gln
530             535             540

Lys Phe Asp Gly His Val Trp Val Ser Trp Glu Thr Phe Glu Gly Glu
545             550             555             560

Thr Val Tyr Met Pro Val Arg Thr Trp Asp Ala Lys Thr Gly Lys Val
            565             570             575

Gly Lys Leu Trp Gly Glu Ile Lys
        580

<210> SEQ ID NO 51
<211> LENGTH: 1749
<212> TYPE: DNA
<213> ORGANISM: artificial
<220> FEATURE:
<223> OTHER INFORMATION: artificial construct

<400> SEQUENCE: 51

```
atgagaggat cgcatcacca tcaccatcac ggatctggct ctggatctgg tatcgaggga    60
agggcaaaga aagatgaaaa atcacaagta tgtagtggtt tggctatgga aaaatatgac   120
attacaaatt taaatgctaa acaagataaa tcaaagaatg ggagcgtgaa agagttgaaa   180
catatctatt caaaccatat taaaggtaac aagattacag caccaaaacc tagtattcaa   240
ggtgtggtca tccacaatga ttatggtagt atgacaccta gtcaatactt ccatggtta    300
tatgcacgtg agaataacgg tacacacgtt aacggttggg ctagtgttta tgcaaataga   360
aacgaagtgc tttggtatca tccgacagac tacgtagagt ggcattgtgg taatcaatgg   420
gcaaatgcta acttaatcgg atttgaagtg tgtgagtcgt atcctggtag aatctcggac   480
aaattattct tagaaaatga agaagcgaca ttgaaagtag ctgcggatgt gatgaagtcg   540
tacggattac cagttaatcg caacactgta cgtctgcata cgaattctt cggaacttct   600
tgtccacatc gttcgtggga cttgcatgtt ggcaaaggtg agccttacac aactactaat   660
attaataaaa tgaaagacta cttcatcaaa cgcatcaaac attattatga cggtgagctc   720
gcaaagaaag atgaaaaatc acaagtatgt agtggtttgg ctatggaaaa atatgacatt   780
acaaatttaa atgctaaaca agataaatca agaatggga gcgtgaaaga gttgaaacat   840
```

-continued

```
atctattcaa accatattaa aggtaacaag attacagcac caaaacctag tattcaaggt    900
gtggtcatcc acaatgatta tggtagtatg acacctagtc aatacttacc atggttatat    960
gcacgtgaga ataacggtac acacgttaac ggttgggcta gtgtttatgc aaatagaaac   1020
gaagtgcttt ggtatcatcc gacagactac gtagagtggc attgtggtaa tcaatgggca   1080
aatgctaact taatcggatt tgaagtgtgt gagtcgtatc ctggtagaat ctcggacaaa   1140
ttattcttag aaaatgaaga agcgacattg aaagtagctg cggatgtgat gaagtcgtac   1200
ggattaccag ttaatcgcaa cactgtacgt ctgcataacg aattcttcgg aacttcttgt   1260
ccacatcgtt cgtgggactt gcatgttggc aaaggtgagc cttacacaac tactaatatt   1320
aataaaatga aagactactt catcaaacgc atcaaacatt attatgacgg tggaaagcta   1380
gaagtaagca aagcagcaac tatcaaacaa tctgacgtta agcaagaagt taaaaagcaa   1440
gaagcaaaac aaattgtgaa agcaacagat tggaaaacaa acaaatatgg cacactatat   1500
aaatcagagt cagctagctt cacacctaat acagatataa taacaagaac gactggtcca   1560
tttagaagca tgccgcagtc aggagtctta aaagcaggtc aaacaattca ttatgatgaa   1620
gtgatgaaac aagacggtca tgtttgggta ggttatacag gtaacagtgg ccaacgtatt   1680
tacttgcctg taagaacatg gaataaatct actaatactt taggtgttct ttggggaact   1740
ataaagtaa                                                           1749
```

<210> SEQ ID NO 52
<211> LENGTH: 582
<212> TYPE: PRT
<213> ORGANISM: artificial
<220> FEATURE:
<223> OTHER INFORMATION: artificial construct

<400> SEQUENCE: 52

```
Met Arg Gly Ser His His His His His His Gly Ser Gly Ser Gly Ser
1               5                   10                  15

Gly Ile Glu Gly Arg Ala Lys Lys Asp Glu Lys Ser Gln Val Cys Ser
            20                  25                  30

Gly Leu Ala Met Glu Lys Tyr Asp Ile Thr Asn Leu Asn Ala Lys Gln
        35                  40                  45

Asp Lys Ser Lys Asn Gly Ser Val Lys Glu Leu Lys His Ile Tyr Ser
    50                  55                  60

Asn His Ile Lys Gly Asn Lys Ile Thr Ala Pro Lys Pro Ser Ile Gln
65                  70                  75                  80

Gly Val Val Ile His Asn Asp Tyr Gly Ser Met Thr Pro Ser Gln Tyr
                85                  90                  95

Leu Pro Trp Leu Tyr Ala Arg Glu Asn Asn Gly Thr His Val Asn Gly
            100                 105                 110

Trp Ala Ser Val Tyr Ala Asn Arg Asn Glu Val Leu Trp Tyr His Pro
        115                 120                 125

Thr Asp Tyr Val Glu Trp His Cys Gly Asn Gln Trp Ala Asn Ala Asn
    130                 135                 140

Leu Ile Gly Phe Glu Val Cys Glu Ser Tyr Pro Gly Arg Ile Ser Asp
145                 150                 155                 160

Lys Leu Phe Leu Glu Asn Glu Glu Ala Thr Leu Lys Val Ala Ala Asp
                165                 170                 175

Val Met Lys Ser Tyr Gly Leu Pro Val Asn Arg Asn Thr Val Arg Leu
            180                 185                 190
```

His Asn Glu Phe Phe Gly Thr Ser Cys Pro His Arg Ser Trp Asp Leu
            195                 200                 205

His Val Gly Lys Gly Glu Pro Tyr Thr Thr Thr Asn Ile Asn Lys Met
    210                 215                 220

Lys Asp Tyr Phe Ile Lys Arg Ile Lys His Tyr Tyr Asp Gly Glu Leu
225                 230                 235                 240

Ala Lys Lys Asp Glu Lys Ser Gln Val Cys Ser Gly Leu Ala Met Glu
                245                 250                 255

Lys Tyr Asp Ile Thr Asn Leu Asn Ala Lys Gln Asp Lys Ser Lys Asn
            260                 265                 270

Gly Ser Val Lys Glu Leu Lys His Ile Tyr Ser Asn His Ile Lys Gly
        275                 280                 285

Asn Lys Ile Thr Ala Pro Lys Pro Ser Ile Gln Gly Val Val Ile His
    290                 295                 300

Asn Asp Tyr Gly Ser Met Thr Pro Ser Gln Tyr Leu Pro Trp Leu Tyr
305                 310                 315                 320

Ala Arg Glu Asn Asn Gly Thr His Val Asn Gly Trp Ala Ser Val Tyr
                325                 330                 335

Ala Asn Arg Asn Glu Val Leu Trp Tyr His Pro Thr Asp Tyr Val Glu
            340                 345                 350

Trp His Cys Gly Asn Gln Trp Ala Asn Ala Asn Leu Ile Gly Phe Glu
        355                 360                 365

Val Cys Glu Ser Tyr Pro Gly Arg Ile Ser Asp Lys Leu Phe Leu Glu
    370                 375                 380

Asn Glu Glu Ala Thr Leu Lys Val Ala Ala Asp Val Met Lys Ser Tyr
385                 390                 395                 400

Gly Leu Pro Val Asn Arg Asn Thr Val Arg Leu His Asn Glu Phe Phe
                405                 410                 415

Gly Thr Ser Cys Pro His Arg Ser Trp Asp Leu His Val Gly Lys Gly
            420                 425                 430

Glu Pro Tyr Thr Thr Thr Asn Ile Asn Lys Met Lys Asp Tyr Phe Ile
        435                 440                 445

Lys Arg Ile Lys His Tyr Tyr Asp Gly Gly Lys Leu Glu Val Ser Lys
    450                 455                 460

Ala Ala Thr Ile Lys Gln Ser Asp Val Lys Gln Glu Val Lys Lys Gln
465                 470                 475                 480

Glu Ala Lys Gln Ile Val Lys Ala Thr Asp Trp Lys Thr Asn Lys Tyr
                485                 490                 495

Gly Thr Leu Tyr Lys Ser Glu Ser Ala Ser Phe Thr Pro Asn Thr Asp
            500                 505                 510

Ile Ile Thr Arg Thr Thr Gly Pro Phe Arg Ser Met Pro Gln Ser Gly
        515                 520                 525

Val Leu Lys Ala Gly Gln Thr Ile His Tyr Asp Glu Val Met Lys Gln
    530                 535                 540

Asp Gly His Val Trp Val Gly Tyr Thr Gly Asn Ser Gly Gln Arg Ile
545                 550                 555                 560

Tyr Leu Pro Val Arg Thr Trp Asn Lys Ser Thr Asn Thr Leu Gly Val
                565                 570                 575

Leu Trp Gly Thr Ile Lys
            580

<210> SEQ ID NO 53
<211> LENGTH: 1755
<212> TYPE: DNA

<213> ORGANISM: artificial
<220> FEATURE:
<223> OTHER INFORMATION: artificial construct

<400> SEQUENCE: 53

```
atgagaggat cgcatcacca tcaccatcac ggatctggct ctggatctgg tatcgaggga      60
agggcaaaga aagatgaaaa atcacaagta tgtagtggtt tggctatgga aaaatatgac    120
attacaaatt taaatgctaa acaagataaa tcaaagaatg ggagcgtgaa agagttgaaa    180
catatctatt caaaccatat taaaggtaac aagattacag caccaaaacc tagtattcaa    240
ggtgtggtca tccacaatga ttatggtagt atgacaccta gtcaatactt accatggtta    300
tatgcacgtg agaataacgg tacacacgtt aacggttggg ctagtgttta tgcaaataga    360
aacgaagtgc tttggtatca tccgacagac tacgtagagt ggcattgtgg taatcaatgg    420
gcaaatgcta acttaatcgg atttgaagtg tgtgagtcgt atcctggtag aatctcggac    480
aaattattct tagaaaatga agaagcgaca ttgaaagtag ctgcggatgt gatgaagtcg    540
tacggattac cagttaatcg caacactgta cgtctgcata acgaattctt cggaacttct    600
tgtccacatc gttcgtggga cttgcatgtt ggcaaaggtg agccttacac aactactaat    660
attaataaaa tgaaagacta cttcatcaaa cgcatcaaac attattatga cggtgagctc    720
gcaaagaaag atgaaaaatc acaagtatgt agtggtttgg ctatggaaaa atatgacatt    780
acaaatttaa atgctaaaca agataaatca agaatggga gcgtgaaaga gttgaaacat    840
atctattcaa accatattaa aggtaacaag attacagcac caaaacctag tattcaaggt    900
gtggtcatcc acaatgatta tggtagtatg acacctagtc aatacttacc atggttatat    960
gcacgtgaga ataacggtac acacgttaac ggttgggcta gtgtttatgc aaatagaaac   1020
gaagtgctt ggtatcatcc gacagactac gtagagtggc attgtggtaa tcaatgggca   1080
aatgctaact taatcggatt tgaagtgtgt gagtcgtatc ctggtagaat ctcggacaaa   1140
ttattcttag aaaatgaaga agcgacattg aaagtagctg cggatgtgat gaagtcgtac   1200
ggattaccag ttaatcgcaa cactgtacgt ctgcataacg aattcttcgg aacttcttgt   1260
ccacatcgtt cgtgggactt gcatgttggc aaaggtgagc cttacacaac tactaatatt   1320
aataaaatga agactactt catcaaacgc atcaaacatt attatgacgg tggaaagcta   1380
gaagtaagca aagcagcaac tatcaaacaa tctgacgtta agcaagaagt taaaaagcaa   1440
gaagcaaaac aaattgtgaa agcaacagat ggtaaatctg caagtaaaat aacagttgga   1500
agtaaagcgc cttataacct taatggtca aaaggtgctt attttaatgc gaaaatcgac   1560
ggcttaggtg ctacttcagc cactagatac ggtgataatc gtactaacta tagattcgat   1620
gttggacagg ctgtatacgc gcctggaaca ttaatatatg tgtttgaaat tatagatggt   1680
tggtgtcgca tttattggaa caatcataat gagtggatat ggcatgagag attgattgtg   1740
aaagaagtgt tttaa                                                    1755
```

<210> SEQ ID NO 54
<211> LENGTH: 584
<212> TYPE: PRT
<213> ORGANISM: artificial
<220> FEATURE:
<223> OTHER INFORMATION: artificial construct

<400> SEQUENCE: 54

```
Met Arg Gly Ser His His His His His His Gly Ser Gly Ser Gly Ser
1               5                   10                  15
```

-continued

```
Gly Ile Glu Gly Arg Ala Lys Lys Asp Glu Lys Ser Gln Val Cys Ser
            20                  25                  30
Gly Leu Ala Met Glu Lys Tyr Asp Ile Thr Asn Leu Asn Ala Lys Gln
        35                  40                  45
Asp Lys Ser Lys Asn Gly Ser Val Lys Glu Leu Lys His Ile Tyr Ser
 50                  55                  60
Asn His Ile Lys Gly Asn Lys Ile Thr Ala Pro Lys Pro Ser Ile Gln
 65                  70                  75                  80
Gly Val Val Ile His Asn Asp Tyr Gly Ser Met Thr Pro Ser Gln Tyr
                85                  90                  95
Leu Pro Trp Leu Tyr Ala Arg Glu Asn Asn Gly Thr His Val Asn Gly
            100                 105                 110
Trp Ala Ser Val Tyr Ala Asn Arg Asn Glu Val Leu Trp Tyr His Pro
        115                 120                 125
Thr Asp Tyr Val Glu Trp His Cys Gly Asn Gln Trp Ala Asn Ala Asn
    130                 135                 140
Leu Ile Gly Phe Glu Val Cys Glu Ser Tyr Pro Gly Arg Ile Ser Asp
145                 150                 155                 160
Lys Leu Phe Leu Glu Asn Glu Glu Ala Thr Leu Lys Val Ala Ala Asp
                165                 170                 175
Val Met Lys Ser Tyr Gly Leu Pro Val Asn Arg Asn Thr Val Arg Leu
            180                 185                 190
His Asn Glu Phe Phe Gly Thr Ser Cys Pro His Arg Ser Trp Asp Leu
        195                 200                 205
His Val Gly Lys Gly Glu Pro Tyr Thr Thr Thr Asn Ile Asn Lys Met
    210                 215                 220
Lys Asp Tyr Phe Ile Lys Arg Ile Lys His Tyr Tyr Asp Gly Glu Leu
225                 230                 235                 240
Ala Lys Lys Asp Glu Lys Ser Gln Val Cys Ser Gly Leu Ala Met Glu
                245                 250                 255
Lys Tyr Asp Ile Thr Asn Leu Asn Ala Lys Gln Asp Lys Ser Lys Asn
            260                 265                 270
Gly Ser Val Lys Glu Leu Lys His Ile Tyr Ser Asn His Ile Lys Gly
        275                 280                 285
Asn Lys Ile Thr Ala Pro Lys Pro Ser Ile Gln Gly Val Val Ile His
    290                 295                 300
Asn Asp Tyr Gly Ser Met Thr Pro Ser Gln Tyr Leu Pro Trp Leu Tyr
305                 310                 315                 320
Ala Arg Glu Asn Asn Gly Thr His Val Asn Gly Trp Ala Ser Val Tyr
                325                 330                 335
Ala Asn Arg Asn Glu Val Leu Trp Tyr His Pro Thr Asp Tyr Val Glu
            340                 345                 350
Trp His Cys Gly Asn Gln Trp Ala Asn Ala Asn Leu Ile Gly Phe Glu
        355                 360                 365
Val Cys Glu Ser Tyr Pro Gly Arg Ile Ser Asp Lys Leu Phe Leu Glu
    370                 375                 380
Asn Glu Glu Ala Thr Leu Lys Val Ala Ala Asp Val Met Lys Ser Tyr
385                 390                 395                 400
Gly Leu Pro Val Asn Arg Asn Thr Val Arg Leu His Asn Glu Phe Phe
                405                 410                 415
Gly Thr Ser Cys Pro His Arg Ser Trp Asp Leu His Val Gly Lys Gly
            420                 425                 430
Glu Pro Tyr Thr Thr Thr Asn Ile Asn Lys Met Lys Asp Tyr Phe Ile
```

```
                    435                 440                 445
Lys Arg Ile Lys His Tyr Tyr Asp Gly Gly Lys Leu Glu Val Ser Lys
450                 455                 460

Ala Ala Thr Ile Lys Gln Ser Asp Val Lys Gln Glu Val Lys Lys Gln
465                 470                 475                 480

Glu Ala Lys Gln Ile Val Lys Ala Thr Asp Gly Lys Ser Ala Ser Lys
            485                 490                 495

Ile Thr Val Gly Ser Lys Ala Pro Tyr Asn Leu Lys Trp Ser Lys Gly
        500                 505                 510

Ala Tyr Phe Asn Ala Lys Ile Asp Gly Leu Gly Ala Thr Ser Ala Thr
    515                 520                 525

Arg Tyr Gly Asp Asn Arg Thr Asn Tyr Arg Phe Asp Val Gly Gln Ala
530                 535                 540

Val Tyr Ala Pro Gly Thr Leu Ile Tyr Val Phe Glu Ile Ile Asp Gly
545                 550                 555                 560

Trp Cys Arg Ile Tyr Trp Asn Asn His Asn Glu Trp Ile Trp His Glu
            565                 570                 575

Arg Leu Ile Val Lys Glu Val Phe
            580

<210> SEQ ID NO 55
<211> LENGTH: 1533
<212> TYPE: DNA
<213> ORGANISM: artificial
<220> FEATURE:
<223> OTHER INFORMATION: artificial construct

<400> SEQUENCE: 55
atgagaggat cgcatcacca tcaccatcac ggatctggct ctggatctgg tatcgaggga      60
aggatggcta agactcaagc agaaataaat aaacgtttag atgcttatgc aaaaggaaca     120
gtagatagcc cttacagagt taaaaaagct acaagttatg acccatcatt tggtgtaatg     180
gaagcaggag ccattgatgc agatggttac tatcacgctc agtgtcaaga ccttattaca     240
gactatgttt tatggttaac agataataaa gttagaactt ggggtaatgc taaagaccaa     300
attaaacaga gttatggtac tggatttaaa atacatgaaa ataaaccttc tactgtacct     360
aaaaaaggtt ggattgcggt atttacatcc ggtagttatg aacagtgggg tcacataggt     420
attgtatatg atggaggtaa tacttctaca tttactattt tagagcaaaa ctggaatggt     480
tatgctaata aaaaacctac aaaacgtgta gataattatt acggattaac tcacttcatt     540
gaaatacctg taaaagcagg aactactgtt aaaaaagaaa cagctaagaa agcgcaagt     600
aaaacgcctg cacctaaaaa gaaagcaaca ctaaaagttt ctaagaatga gctcatggct     660
aagactcaag cagaaataaa taaacgttta gatgcttatg caaaaggaac agtagatagc     720
ccttacagag ttaaaaaagc tacaagttat gacccatcat ttggtgtaat ggaagcagga     780
gccattgatg cagatggtta ctatcacgct cagtgtcaag accttattac agactatgtt     840
ttatggttaa cagataataa agttagaact tggggtaatg ctaaagacca aattaaacag     900
agttatggta ctggatttaa aatacatgaa aataaacctt ctactgtacc taaaaaaggt     960
tggattgcgg tatttacatc cggtagttat gaacagtggg gtcacatagg tattgtatat    1020
gatggaggta atacttctac atttactatt ttagagcaaa actggaatgg ttatgctaat    1080
aaaaaaccta caaaacgtgt agataattat tacggattaa ctcacttcat tgaaatacct    1140
gtaaaagcag gaaagctaga agtaagcaaa gcagcaacta tcaaacaatc tgacgttaag    1200
```

-continued

```
caagaagtta aaaagcaaga agcaaaacaa attgtgaaag caacagattg gaaacagaat    1260
aaagatggca tttggtataa agctgaacat gcttcgttca cagtgacagc accagaggga    1320
attatcacaa gatacaaagg tccttggact ggtcacccac aagctggtgt attacaaaaa    1380
ggtcaaacga ttaaatatga tgaggttcaa aaatttgacg gtcatgtttg ggtatcgtgg    1440
gaaacgtttg agggcgaaac tgtatacatg ccggtacgca catgggacgc taaaactggt    1500
aaagttggta agttgtgggg cgaaattaaa taa                                  1533
```

<210> SEQ ID NO 56
<211> LENGTH: 510
<212> TYPE: PRT
<213> ORGANISM: artificial
<220> FEATURE:
<223> OTHER INFORMATION: artificial construct

<400> SEQUENCE: 56

```
Met Arg Gly Ser His His His His His Gly Ser Gly Ser Gly Ser
1               5                   10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
        195                 200                 205

Ala Thr Leu Lys Val Ser Lys Asn Glu Leu Met Ala Lys Thr Gln Ala
    210                 215                 220

Glu Ile Asn Lys Arg Leu Asp Ala Tyr Ala Lys Gly Thr Val Asp Ser
225                 230                 235                 240

Pro Tyr Arg Val Lys Lys Ala Thr Ser Tyr Asp Pro Ser Phe Gly Val
                245                 250                 255

Met Glu Ala Gly Ala Ile Asp Ala Asp Gly Tyr Tyr His Ala Gln Cys
            260                 265                 270

Gln Asp Leu Ile Thr Asp Tyr Val Leu Trp Leu Thr Asp Asn Lys Val
        275                 280                 285

Arg Thr Trp Gly Asn Ala Lys Asp Gln Ile Lys Gln Ser Tyr Gly Thr
    290                 295                 300
```

Gly Phe Lys Ile His Glu Asn Lys Pro Ser Thr Val Pro Lys Lys Gly
305                 310                 315                 320

Trp Ile Ala Val Phe Thr Ser Ser Tyr Glu Gln Trp Gly His Ile
            325                 330                 335

Gly Ile Val Tyr Asp Gly Gly Asn Thr Ser Thr Phe Thr Ile Leu Glu
            340                 345                 350

Gln Asn Trp Asn Gly Tyr Ala Asn Lys Lys Pro Thr Lys Arg Val Asp
            355                 360                 365

Asn Tyr Tyr Gly Leu Thr His Phe Ile Glu Ile Pro Val Lys Ala Gly
    370                 375                 380

Lys Leu Glu Val Ser Lys Ala Ala Thr Ile Lys Gln Ser Asp Val Lys
385                 390                 395                 400

Gln Glu Val Lys Lys Gln Glu Ala Lys Gln Ile Val Lys Ala Thr Asp
            405                 410                 415

Trp Lys Gln Asn Lys Asp Gly Ile Trp Tyr Lys Ala Glu His Ala Ser
            420                 425                 430

Phe Thr Val Thr Ala Pro Glu Gly Ile Ile Thr Arg Tyr Lys Gly Pro
    435                 440                 445

Trp Thr Gly His Pro Gln Ala Gly Val Leu Gln Lys Gly Gln Thr Ile
            450                 455                 460

Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
            485                 490                 495

Ala Lys Thr Gly Lys Val Gly Lys Leu Trp Gly Glu Ile Lys
            500                 505                 510

<210> SEQ ID NO 57
<211> LENGTH: 1470
<212> TYPE: DNA
<213> ORGANISM: artificial
<220> FEATURE:
<223> OTHER INFORMATION: artificial construct

<400> SEQUENCE: 57

| | |
|---|---|
| atgagaggat cgcatcacca tcaccatcac ggatctggct ctggatctgg tatcgaggga | 60 |
| aggatggcta agactcaagc agaaataaat aaacgtttag atgcttatgc aaaaggaaca | 120 |
| gtagatagcc cttacagagt taaaaaagct acaagttatg acccatcatt ggtgtaatg | 180 |
| gaagcaggag ccattgatgc agatggttac tatcacgctc agtgtcaaga ccttattaca | 240 |
| gactatgttt tatggttaac agataataaa gttagaactt ggggtaatgc taaagaccaa | 300 |
| attaaacaga gttatggtac tggatttaaa atacatgaaa ataaaccttc tactgtacct | 360 |
| aaaaaaggtt ggattgcggt atttacatcc ggtagttatg aacagtgggg tcacataggt | 420 |
| attgtatatg atggaggtaa tacttctaca tttactattt tagagcaaaa ctggaatggt | 480 |
| tatgctaata aaaaacctac aaaacgtgta gataattatt acggattaac tcacttcatt | 540 |
| gaaatacctg taaaagcagg aactactgtt aaaaaagaaa cagctaagaa agcgcaagt | 600 |
| aaaacgcctg cacctaaaaa gaaagcaaca ctaaaagttt ctaagaatga gctcatggct | 660 |
| aagactcaag cagaaataaa taacgtttta gatgcttatg caaaaggaac agtagatagc | 720 |
| ccttacagag ttaaaaaagc tacaagttat gacccatcat tggtgtaat ggaagcagga | 780 |
| gccattgatg cagatggtta ctatcacgct cagtgtcaag accttattac agactatgtt | 840 |
| ttatggttaa cagataataa agttagaact tggggtaatg ctaaagacca aattaaacag | 900 |

-continued

```
agttatggta ctggatttaa atacatgaa  ataaaccct  ctactgtacc taaaaaggt   960
tggattgcgg tatttacatc cggtagttat gaacagtggg gtcacatagg tattgtatat  1020
gatggaggta atacttctac atttactatt ttagagcaaa actggaatgg ttatgctaat  1080
aaaaaaccta caaacgtgt  agataattat tacggattaa ctcacttcat tgaaatacct  1140
gtaaaagcag gaaaagcagg tggtacagta actccaacgc cgaatacagg ttggaaaaca  1200
aacaaatatg gcacactata taatcagag  tcagctagct tcacacctaa tacagatata  1260
ataacaagaa cgactggtcc atttagaagc atgccgcagt caggagtctt aaaagcaggt  1320
caaacaattc attatgatga agtgatgaaa caagacggtc atgtttgggt aggttataca  1380
ggtaacagtg gccaacgtat ttacttgcct gtaagaacat ggaataaatc tactaatact  1440
ttaggtgttc tttggggaac tataaagtaa                                    1470
```

<210> SEQ ID NO 58
<211> LENGTH: 489
<212> TYPE: PRT
<213> ORGANISM: artificial
<220> FEATURE:
<223> OTHER INFORMATION: artificial construct

<400> SEQUENCE: 58

```
Met Arg Gly Ser His His His His His His Gly Ser Gly Ser Gly Ser
1               5                   10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
        195                 200                 205

Ala Thr Leu Lys Val Ser Lys Asn Glu Leu Met Ala Lys Thr Gln Ala
    210                 215                 220

Glu Ile Asn Lys Arg Leu Asp Ala Tyr Ala Lys Gly Thr Val Asp Ser
225                 230                 235                 240

Pro Tyr Arg Val Lys Lys Ala Thr Ser Tyr Asp Pro Ser Phe Gly Val
                245                 250                 255

Met Glu Ala Gly Ala Ile Asp Ala Asp Gly Tyr Tyr His Ala Gln Cys
```

```
                    260                 265                 270
Gln Asp Leu Ile Thr Asp Tyr Val Leu Trp Leu Thr Asp Asn Lys Val
            275                 280                 285

Arg Thr Trp Gly Asn Ala Lys Asp Gln Ile Lys Gln Ser Tyr Gly Thr
            290                 295                 300

Gly Phe Lys Ile His Glu Asn Lys Pro Ser Thr Val Pro Lys Lys Gly
305                 310                 315                 320

Trp Ile Ala Val Phe Thr Ser Ser Tyr Glu Gln Trp Gly His Ile
                325                 330                 335

Gly Ile Val Tyr Asp Gly Gly Asn Thr Ser Thr Phe Thr Ile Leu Glu
            340                 345                 350

Gln Asn Trp Asn Gly Tyr Ala Asn Lys Lys Pro Thr Lys Arg Val Asp
            355                 360                 365

Asn Tyr Tyr Gly Leu Thr His Phe Ile Glu Ile Pro Val Lys Ala Gly
            370                 375                 380

Lys Ala Gly Gly Thr Val Thr Pro Thr Pro Asn Thr Gly Trp Lys Thr
385                 390                 395                 400

Asn Lys Tyr Gly Thr Leu Tyr Lys Ser Glu Ser Ala Ser Phe Thr Pro
                405                 410                 415

Asn Thr Asp Ile Ile Thr Arg Thr Thr Gly Pro Phe Arg Ser Met Pro
                420                 425                 430

Gln Ser Gly Val Leu Lys Ala Gly Gln Thr Ile His Tyr Asp Glu Val
            435                 440                 445

Met Lys Gln Asp Gly His Val Trp Val Gly Tyr Thr Gly Asn Ser Gly
450                 455                 460

Gln Arg Ile Tyr Leu Pro Val Arg Thr Trp Asn Lys Ser Thr Asn Thr
465                 470                 475                 480

Leu Gly Val Leu Trp Gly Thr Ile Lys
                485
```

<210> SEQ ID NO 59
<211> LENGTH: 1524
<212> TYPE: DNA
<213> ORGANISM: artificial
<220> FEATURE:
<223> OTHER INFORMATION: artificial construct

<400> SEQUENCE: 59

| | | | | | |
|---|---|---|---|---|---|
| atgagaggat | cgcatcacca | tcaccatcac | ggatctggct | ctggatctgg | tatcgaggga | 60 |
| aggatggcta | agactcaagc | agaaataaat | aaacgtttag | atgcttatgc | aaaaggaaca | 120 |
| gtagatagcc | cttacagagt | taaaaaagct | acaagttatg | acccatcatt | tggtgtaatg | 180 |
| gaagcaggag | ccattgatgc | agatggttac | tatcacgctc | agtgtcaaga | ccttattaca | 240 |
| gactatgttt | tatggttaac | agataataaa | gttagaactt | ggggtaatgc | taaagaccaa | 300 |
| attaaacaga | gttatggtac | tggatttaaa | atacatgaaa | ataaaccttc | tactgtacct | 360 |
| aaaaaaggtt | ggattgcggt | atttacatcc | ggtagttatg | aacagtgggg | tcacataggt | 420 |
| attgtatatg | atggaggtaa | tacttctaca | tttactattt | tagagcaaaa | ctggaatggt | 480 |
| tatgctaata | aaaaacctac | aaaacgtgta | gataattatt | acggattaac | tcacttcatt | 540 |
| gaaatacctg | taaaagcagg | aactactgtt | aaaaagaaa | cagctaagaa | agcgcaagt | 600 |
| aaaacgcctg | cacctaaaaa | gaaagcaaca | ctaaagtttt | ctaagaatga | gctcatggct | 660 |
| aagactcaag | cagaaataaa | taacgtttta | gatgcttatg | caaaaggaac | agtagatagc | 720 |
| ccttacagag | ttaaaaaagc | tacaagttat | gacccatcat | ttggtgtaat | ggaagcagga | 780 |

```
gccattgatg cagatggtta ctatcacgct cagtgtcaag accttattac agactatgtt    840
ttatggttaa cagataataa agttagaact tgggtaatg ctaaagacca aattaaacag     900
agttatggta ctggatttaa aatacatgaa aataaacctt ctactgtacc taaaaaaggt    960
tggattgcgg tatttacatc cggtagttat gaacagtggg gtcacatagg tattgtatat   1020
gatggaggta atacttctac atttactatt ttagagcaaa actggaatgg ttatgctaat   1080
aaaaaaccta caaaacgtgt agataattat tacggattaa ctcacttcat tgaaatacct   1140
gtaaaagcag gaactactgt taaaaaagaa acagctaaga aaagcgcaag taaaacgcct   1200
gcacctaaaa agaaagcaac actaaaagtt tctaagaatg gtaaatctgc aagtaaaata   1260
acagttggaa gtaaagcgcc ttataacctt aaatggtcaa aaggtgctta ttttaatgcg   1320
aaaatcgacg gcttaggtgc tacttcagcc actagatacg gtgataatcg tactaactat   1380
agattcgatg ttggacaggc tgtatacgcg cctggaacat taatatatgt gtttgaaatt   1440
atagatggtt ggtgtcgcat ttattggaac aatcataatg agtggatatg gcatgagaga   1500
ttgattgtga agaagtgtt ttaa                                           1524
```

<210> SEQ ID NO 60
<211> LENGTH: 507
<212> TYPE: PRT
<213> ORGANISM: artificial
<220> FEATURE:
<223> OTHER INFORMATION: artificial construct

<400> SEQUENCE: 60

```
Met Arg Gly Ser His His His His His His Gly Ser Gly Ser
1               5                   10                  15

Gly Ile Glu Gly Arg Met Ala Lys Thr Gln Ala Glu Ile Asn Lys Arg
            20                  25                  30

Leu Asp Ala Tyr Ala Lys Gly Thr Val Asp Ser Pro Tyr Arg Val Lys
        35                  40                  45

Lys Ala Thr Ser Tyr Asp Pro Ser Phe Gly Val Met Glu Ala Gly Ala
    50                  55                  60

Ile Asp Ala Asp Gly Tyr Tyr His Ala Gln Cys Gln Asp Leu Ile Thr
65                  70                  75                  80

Asp Tyr Val Leu Trp Leu Thr Asp Asn Lys Val Arg Thr Trp Gly Asn
                85                  90                  95

Ala Lys Asp Gln Ile Lys Gln Ser Tyr Gly Thr Gly Phe Lys Ile His
            100                 105                 110

Glu Asn Lys Pro Ser Thr Val Pro Lys Lys Gly Trp Ile Ala Val Phe
        115                 120                 125

Thr Ser Gly Ser Tyr Glu Gln Trp Gly His Ile Gly Ile Val Tyr Asp
    130                 135                 140

Gly Gly Asn Thr Ser Thr Phe Thr Ile Leu Glu Gln Asn Trp Asn Gly
145                 150                 155                 160

Tyr Ala Asn Lys Lys Pro Thr Lys Arg Val Asp Asn Tyr Tyr Gly Leu
                165                 170                 175

Thr His Phe Ile Glu Ile Pro Val Lys Ala Gly Thr Thr Val Lys Lys
            180                 185                 190

Glu Thr Ala Lys Lys Ser Ala Ser Lys Thr Pro Ala Pro Lys Lys Lys
        195                 200                 205

Ala Thr Leu Lys Val Ser Lys Asn Glu Leu Met Ala Lys Thr Gln Ala
    210                 215                 220
```

Glu Ile Asn Lys Arg Leu Asp Ala Tyr Ala Lys Gly Thr Val Asp Ser
225                 230                 235                 240

Pro Tyr Arg Val Lys Lys Ala Thr Ser Tyr Asp Pro Ser Phe Gly Val
            245                 250                 255

Met Glu Ala Gly Ala Ile Asp Ala Asp Gly Tyr Tyr His Ala Gln Cys
        260                 265                 270

Gln Asp Leu Ile Thr Asp Tyr Val Leu Trp Leu Thr Asp Asn Lys Val
    275                 280                 285

Arg Thr Trp Gly Asn Ala Lys Asp Gln Ile Lys Gln Ser Tyr Gly Thr
290                 295                 300

Gly Phe Lys Ile His Glu Asn Lys Pro Ser Thr Val Pro Lys Lys Gly
305                 310                 315                 320

Trp Ile Ala Val Phe Thr Ser Gly Ser Tyr Glu Gln Trp Gly His Ile
                325                 330                 335

Gly Ile Val Tyr Asp Gly Gly Asn Thr Ser Thr Phe Thr Ile Leu Glu
            340                 345                 350

Gln Asn Trp Asn Gly Tyr Ala Asn Lys Lys Pro Thr Lys Arg Val Asp
        355                 360                 365

Asn Tyr Tyr Gly Leu Thr His Phe Ile Glu Ile Pro Val Lys Ala Gly
370                 375                 380

Thr Thr Val Lys Lys Glu Thr Ala Lys Lys Ser Ala Ser Lys Thr Pro
385                 390                 395                 400

Ala Pro Lys Lys Lys Ala Thr Leu Lys Val Ser Lys Asn Gly Lys Ser
                405                 410                 415

Ala Ser Lys Ile Thr Val Gly Ser Lys Ala Pro Tyr Asn Leu Lys Trp
            420                 425                 430

Ser Lys Gly Ala Tyr Phe Asn Ala Lys Ile Asp Gly Leu Gly Ala Thr
        435                 440                 445

Ser Ala Thr Arg Tyr Gly Asp Asn Arg Thr Asn Tyr Arg Phe Asp Val
450                 455                 460

Gly Gln Ala Val Tyr Ala Pro Gly Thr Leu Ile Tyr Val Phe Glu Ile
465                 470                 475                 480

Ile Asp Gly Trp Cys Arg Ile Tyr Trp Asn Asn His Asn Glu Trp Ile
                485                 490                 495

Trp His Glu Arg Leu Ile Val Lys Glu Val Phe
            500                 505

<210> SEQ ID NO 61
<211> LENGTH: 1446
<212> TYPE: DNA
<213> ORGANISM: artificial
<220> FEATURE:
<223> OTHER INFORMATION: artificial construct

<400> SEQUENCE: 61
atgagaggat cgcatcacca tcaccatcac ggatctggct ctggatctgg tatcgaggga      60
aggatgaaaa ccctgaaaca agcagagtcc tacattaaga gtaaagtaaa tacaggaact     120
gattttgatg gtttatatgg gtatcagtgt atggacttag cagtagatta tatttaccat     180
gtaacagatg gtaaaataag aatgtggggt aatgctaagg atgcgataaa taactctttt     240
ggtggtactg ctacggtata taaaaactac cctgctttta gacctaagta cggtgatgta     300
gtcgtatgga ctactggtaa ttttgcaact tatggtcata tcgcaatagt tactaaccct     360
gacccttatg agaccttca atatgttaca gttcttgaac aaaactggaa cggtaacggg     420
atttataaaa ccgagttagc tacaatcaga acacacgatt acacaggaat tacacatttt     480

```
attagaccta actttgctac tgaatcaagt gtaaaaaaga aagatacaaa gaaaaaacca    540
aaaccatcaa atagagatgg aataaataaa gataaaattg tatatgatag aactaatatt    600
aattacaatg agctcatgaa aaccctgaaa caagcagagt cctacattaa gagtaaagta    660
aatacaggaa ctgattttga tggtttatat gggtatcagt gtatggactt agcagtagat    720
tatatttacc atgtaacaga tggtaaaata agaatgtggg gtaatgctaa ggatgcgata    780
aataactctt ttggtggtac tgctacggta tataaaaact accctgcttt tagacctaag    840
tacggtgatg tagtcgtatg gactactggt aattttgcaa cttatggtca tatcgcaata    900
gttactaacc ctgaccctta tggagacctt caatatgtta cagttcttga acaaaactgg    960
aacggtaacg ggatttataa aaccgagtta gctacaatca aacacacga ttacacagga   1020 attacacatt ttattagacc taactttgct actgaatcaa gtgtaaaaaa gaaagataca   1080
aagaaaaaac caaaccatca aatagagat ggaataaata agataaaat tgtatatgat   1140 agaactaata ttaattacaa ttggaaacag aataaagatg gcatttggta taaagctgaa   1200
catgcttcgt tcacagtgac agcaccagag ggaattatca aagatacaa aggtccttgg   1260 actggtcacc cacaagctgg tgtattacaa aaaggtcaaa cgattaaata tgatgaggtt   1320
caaaaatttg acggtcatgt ttgggtatcg tgggaaacgt ttgagggcga aactgtatac   1380
atgccggtac gcacatggga cgctaaaaact ggtaaagttg gtaagttgtg gggcgaaatt   1440
aaataa                                                              1446
```

<210> SEQ ID NO 62
<211> LENGTH: 481
<212> TYPE: PRT
<213> ORGANISM: artificial
<220> FEATURE:
<223> OTHER INFORMATION: artificial construct

<400> SEQUENCE: 62

```
Met Arg Gly Ser His His His His His His Gly Ser Gly Ser Gly Ser
1               5                   10                  15

Gly Ile Glu Gly Arg Met Lys Thr Leu Lys Gln Ala Glu Ser Tyr Ile
            20                  25                  30

Lys Ser Lys Val Asn Thr Gly Thr Asp Phe Asp Gly Leu Tyr Gly Tyr
        35                  40                  45

Gln Cys Met Asp Leu Ala Val Asp Tyr Ile Tyr His Val Thr Asp Gly
    50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Val Trp Thr Thr Gly Asn Phe Ala Thr Tyr Gly
            100                 105                 110

His Ile Ala Ile Val Thr Asn Pro Asp Pro Tyr Gly Asp Leu Gln Tyr
        115                 120                 125

Val Thr Val Leu Glu Gln Asn Trp Asn Gly Asn Gly Ile Tyr Lys Thr
    130                 135                 140

Glu Leu Ala Thr Ile Arg Thr His Asp Tyr Thr Gly Ile Thr His Phe
145                 150                 155                 160

Ile Arg Pro Asn Phe Ala Thr Glu Ser Ser Val Lys Lys Lys Asp Thr
                165                 170                 175

Lys Lys Lys Pro Lys Pro Ser Asn Arg Asp Gly Ile Asn Lys Asp Lys
```

```
               180                 185                 190
Ile Val Tyr Asp Arg Thr Asn Ile Asn Tyr Asn Glu Leu Met Lys Thr
            195                 200                 205
Leu Lys Gln Ala Glu Ser Tyr Ile Lys Ser Lys Val Asn Thr Gly Thr
            210                 215                 220
Asp Phe Asp Gly Leu Tyr Gly Tyr Gln Cys Met Asp Leu Ala Val Asp
225                 230                 235                 240
Tyr Ile Tyr His Val Thr Asp Gly Lys Ile Arg Met Trp Gly Asn Ala
            245                 250                 255
Lys Asp Ala Ile Asn Asn Ser Phe Gly Gly Thr Ala Thr Val Tyr Lys
            260                 265                 270
Asn Tyr Pro Ala Phe Arg Pro Lys Tyr Gly Asp Val Val Trp Thr
            275                 280                 285
Thr Gly Asn Phe Ala Thr Tyr Gly His Ile Ala Ile Val Thr Asn Pro
            290                 295                 300
Asp Pro Tyr Gly Asp Leu Gln Tyr Val Thr Val Leu Glu Gln Asn Trp
305                 310                 315                 320
Asn Gly Asn Gly Ile Tyr Lys Thr Glu Leu Ala Thr Ile Arg Thr His
            325                 330                 335
Asp Tyr Thr Gly Ile Thr His Phe Ile Arg Pro Asn Phe Ala Thr Glu
            340                 345                 350
Ser Ser Val Lys Lys Lys Asp Thr Lys Lys Pro Lys Pro Ser Asn
            355                 360                 365
Arg Asp Gly Ile Asn Lys Asp Lys Ile Val Tyr Asp Arg Thr Asn Ile
            370                 375                 380
Asn Tyr Asn Trp Lys Gln Asn Lys Asp Gly Ile Trp Tyr Lys Ala Glu
385                 390                 395                 400
His Ala Ser Phe Thr Val Thr Ala Pro Glu Gly Ile Ile Thr Arg Tyr
            405                 410                 415
Lys Gly Pro Trp Thr Gly His Pro Gln Ala Gly Val Leu Gln Lys Gly
            420                 425                 430
Gln Thr Ile Lys Tyr Asp Glu Val Gln Lys Phe Asp Gly His Val Trp
            435                 440                 445
Val Ser Trp Glu Thr Phe Glu Gly Glu Thr Val Tyr Met Pro Val Arg
            450                 455                 460
Thr Trp Asp Ala Lys Thr Gly Lys Val Gly Lys Leu Trp Gly Glu Ile
465                 470                 475                 480
Lys

<210> SEQ ID NO 63
<211> LENGTH: 1440
<212> TYPE: DNA
<213> ORGANISM: artificial
<220> FEATURE:
<223> OTHER INFORMATION: artificial construct

<400> SEQUENCE: 63
atgagaggat cgcatcacca tcaccatcac ggatctggct ctggatctgg tatcgaggga      60
aggatgaaaa ccctgaaaca agcagagtcc tacattaaga gtaaagtaaa tacaggaact     120
gattttgatg gtttatatgg gtatcagtgt atggacttag cagtagatta tatttaccat     180
gtaacagatg gtaaaataag aatgtggggt aatgctaagg atgcgataaa taactctttt     240
ggtggtactg ctacggtata taaaaactac cctgctttta gacctaagta cggtgatgta     300
gtcgtatgga ctactggtaa ttttgcaact tatggtcata tcgcaatagt tactaaccct     360
```

```
gacccttatg gagaccttca atatgttaca gttcttgaac aaaactggaa cggtaacggg      420
atttataaaa ccgagttagc tacaatcaga acacacgatt acacaggaat tacacatttt      480
attagaccta actttgctac tgaatcaagt gtaaaaaaga agatacaaa gaaaaaacca       540
aaaccatcaa atagagatgg aataaataaa gataaaattg tatatgatag aactaatatt      600
aattacaatg agctcatgaa aaccctgaaa caagcagagt cctacattaa gagtaaagta      660
aatacaggaa ctgattttga tggtttatat gggtatcagt gtatggactt agcagtagat      720
tatatttacc atgtaacaga tggtaaaata agaatgtggg gtaatgctaa ggatgcgata      780
aataactctt ttggtggtac tgctacggta tataaaaact accctgcttt tagacctaag      840
tacggtgatg tagtcgtatg gactactggt aattttgcaa cttatggtca tatcgcaata      900
gttactaacc ctgacccctta tggagacctt caatatgtta cagttcttga acaaaactgg      960
aacggtaacg ggatttataa aaccgagtta gctacaatca gaacacacga ttacacagga     1020
attacacatt ttattagacc taactttgct actgaatcaa gtgtaaaaaa gaaagataca     1080
aagaaaaaac caaaaccatc aaatagagat ggaataaata agataaaat tgtatatgat     1140
agaactaata ttaattacaa ttggaaaaca aacaaatatg gcacactata taatcagag     1200
tcagctagct tcacacctaa tacagatata ataacaagaa cgactggtcc atttagaagc     1260
atgccgcagt caggagtctt aaaagcaggt caaacaattc attatgatga agtgatgaaa     1320
caagacggtc atgtttgggt aggttataca ggtaacagtg ccaacgtat ttacttgcct      1380
gtaagaacat ggaataaatc tactaatact ttaggtgttc tttggggaac tataaagtaa     1440
```

<210> SEQ ID NO 64
<211> LENGTH: 479
<212> TYPE: PRT
<213> ORGANISM: artificial
<220> FEATURE:
<223> OTHER INFORMATION: artificial construct

<400> SEQUENCE: 64

```
Met Arg Gly Ser His His His His His Gly Ser Gly Ser Gly Ser
1               5                   10                  15

Gly Ile Glu Gly Arg Met Lys Thr Leu Lys Gln Ala Glu Ser Tyr Ile
            20                  25                  30

Lys Ser Lys Val Asn Thr Gly Thr Asp Phe Asp Gly Leu Tyr Gly Tyr
        35                  40                  45

Gln Cys Met Asp Leu Ala Val Asp Tyr Ile Tyr His Val Thr Asp Gly
    50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Val Trp Thr Thr Gly Asn Phe Ala Thr Tyr Gly
            100                 105                 110

His Ile Ala Ile Val Thr Asn Pro Asp Pro Tyr Gly Asp Leu Gln Tyr
        115                 120                 125

Val Thr Val Leu Glu Gln Asn Trp Asn Gly Asn Gly Ile Tyr Lys Thr
    130                 135                 140

Glu Leu Ala Thr Ile Arg Thr His Asp Tyr Thr Gly Ile Thr His Phe
145                 150                 155                 160

Ile Arg Pro Asn Phe Ala Thr Glu Ser Ser Val Lys Lys Lys Asp Thr
                165                 170                 175
```

Lys Lys Lys Pro Lys Pro Ser Asn Arg Asp Gly Ile Asn Lys Asp Lys
            180                 185                 190

Ile Val Tyr Asp Arg Thr Asn Ile Asn Tyr Asn Glu Leu Met Lys Thr
        195                 200                 205

Leu Lys Gln Ala Glu Ser Tyr Ile Lys Ser Lys Val Asn Thr Gly Thr
    210                 215                 220

Asp Phe Asp Gly Leu Tyr Gly Tyr Gln Cys Met Asp Leu Ala Val Asp
225                 230                 235                 240

Tyr Ile Tyr His Val Thr Asp Gly Lys Ile Arg Met Trp Gly Asn Ala
                245                 250                 255

Lys Asp Ala Ile Asn Asn Ser Phe Gly Gly Thr Ala Thr Val Tyr Lys
            260                 265                 270

Asn Tyr Pro Ala Phe Arg Pro Lys Tyr Gly Asp Val Val Val Trp Thr
        275                 280                 285

Thr Gly Asn Phe Ala Thr Tyr Gly His Ile Ala Ile Val Thr Asn Pro
    290                 295                 300

Asp Pro Tyr Gly Asp Leu Gln Tyr Val Thr Val Leu Glu Gln Asn Trp
305                 310                 315                 320

Asn Gly Asn Gly Ile Tyr Lys Thr Glu Leu Ala Thr Ile Arg Thr His
                325                 330                 335

Asp Tyr Thr Gly Ile Thr His Phe Ile Arg Pro Asn Phe Ala Thr Glu
            340                 345                 350

Ser Ser Val Lys Lys Asp Thr Lys Lys Pro Lys Pro Ser Asn
        355                 360                 365

Arg Asp Gly Ile Asn Lys Asp Lys Ile Val Tyr Asp Arg Thr Asn Ile
370                 375                 380

Asn Tyr Asn Trp Lys Thr Asn Lys Tyr Gly Thr Leu Tyr Lys Ser Glu
385                 390                 395                 400

Ser Ala Ser Phe Thr Pro Asn Thr Asp Ile Ile Thr Arg Thr Gly
            405                 410                 415

Pro Phe Arg Ser Met Pro Gln Ser Gly Val Leu Lys Ala Gly Gln Thr
                420                 425                 430

Ile His Tyr Asp Glu Val Met Lys Gln Asp Gly His Val Trp Val Gly
            435                 440                 445

Tyr Thr Gly Asn Ser Gly Gln Arg Ile Tyr Leu Pro Val Arg Thr Trp
    450                 455                 460

Asn Lys Ser Thr Asn Thr Leu Gly Val Leu Trp Gly Thr Ile Lys
465                 470                 475

<210> SEQ ID NO 65
<211> LENGTH: 1446
<212> TYPE: DNA
<213> ORGANISM: artificial
<220> FEATURE:
<223> OTHER INFORMATION: artificial construct

<400> SEQUENCE: 65
atgagaggat cgcatcacca tcaccatcac ggatctggct ctggatctgg tatcgaggga    60
aggatgaaaa ccctgaaaca agcagagtcc tacattaaga gtaaagtaaa tacaggaact   120
gattttgatg gtttatatgg gtatcagtgt atggacttag cagtagatta tatttaccat   180
gtaacagatg gtaaaataag aatgtggggt aatgctaagg atgcgataaa taactctttt   240
ggtggtactg ctacggtata taaaaactac cctgctttta gacctaagta cggtgatgta   300
gtcgtatgga ctactggtaa ttttgcaact tatggtcata tcgcaatagt tactaaccct   360

```
gacccttatg gagaccttca atatgttaca gttcttgaac aaaactggaa cggtaacggg    420
atttataaaa ccgagttagc tacaatcaga acacacgatt acacaggaat acacatttt    480 attagaccta actttgctac tgaatcaagt gtaaaaaaga agatacaaa gaaaaaacca    540 aaaccatcaa atagagatgg aataaataaa gataaaattg tatatgatag aactaatatt    600
aattacaatg agctcatgaa aaccctgaaa caagcagagt cctacattaa gagtaaagta    660
aatacaggaa ctgattttga tggtttatat gggtatcagt gtatggactt agcagtagat    720
tatatttacc atgtaacaga tggtaaaata agaatgtggg gtaatgctaa ggatgcgata    780
aataactctt ttggtggtac tgctacggta tataaaaact accctgcttt tagacctaag    840
tacggtgatg tagtcgtatg gactactggt aattttgcaa cttatggtca tatcgcaata    900
gttactaacc ctgacccttta tggagacctt caatatgtta cagttcttga acaaaactgg    960
aacggtaacg ggatttataa aaccgagtta gctacaatca gaacacacga ttacacagga    1020
attacacatt ttattagacc taactttgct actgaatcaa gtgtaaaaaa gaaagataca    1080
aagaaaaaac caaaaccatc aaatagagat ggaataaata agataaaat tgtatatgat    1140 agaactaata ttaattacaa tggtaaatct gcaagtaaaa taacagttgg aagtaaagcg    1200
ccttataacc ttaaatggtc aaaaggtgct tattttaatg cgaaaatcga cggcttaggt    1260
gctacttcag ccactagata cggtgataat cgtactaact atagattcga tgttggacag    1320
gctgtatacg cgcctggaac attaatatat gtgtttgaaa ttatagatgg ttggtgtcgc    1380
atttattgga caatcataa tgagtggata tggcatgaga gattgattgt gaaagaagtg    1440
ttttaa                                                              1446

<210> SEQ ID NO 66
<211> LENGTH: 481
<212> TYPE: PRT
<213> ORGANISM: artificial
<220> FEATURE:
<223> OTHER INFORMATION: artificial construct

<400> SEQUENCE: 66

Met Arg Gly Ser His His His His His Gly Ser Gly Ser Gly Ser
1               5                   10                  15

Gly Ile Glu Gly Arg Met Lys Thr Leu Lys Gln Ala Glu Ser Tyr Ile
            20                  25                  30

Lys Ser Lys Val Asn Thr Gly Thr Asp Phe Asp Gly Leu Tyr Gly Tyr
        35                  40                  45

Gln Cys Met Asp Leu Ala Val Asp Tyr Ile Tyr His Val Thr Asp Gly
    50                  55                  60

Lys Ile Arg Met Trp Gly Asn Ala Lys Asp Ala Ile Asn Asn Ser Phe
65                  70                  75                  80

Gly Gly Thr Ala Thr Val Tyr Lys Asn Tyr Pro Ala Phe Arg Pro Lys
                85                  90                  95

Tyr Gly Asp Val Val Val Trp Thr Thr Gly Asn Phe Ala Thr Tyr Gly
            100                 105                 110

His Ile Ala Ile Val Thr Asn Pro Asp Pro Tyr Gly Asp Leu Gln Tyr
        115                 120                 125

Val Thr Val Leu Glu Gln Asn Trp Asn Gly Asn Gly Ile Tyr Lys Thr
    130                 135                 140

Glu Leu Ala Thr Ile Arg Thr His Asp Tyr Thr Gly Ile Thr His Phe
145                 150                 155                 160
```

-continued

| | | | | | | | | | | | |
|---|---|---|---|---|---|---|---|---|---|---|---|
|Ile|Arg|Pro|Asn|Phe|Ala|Thr|Glu|Ser|Ser|Val|Lys|Lys|Asp|Thr|
| | | |165| | | |170| | | |175| | | |
|Lys|Lys|Lys|Pro|Lys|Pro|Ser|Asn|Arg|Asp|Gly|Ile|Asn|Lys|Asp|Lys|
| | | |180| | |185| | | |190| | | |

Ile Arg Pro Asn Phe Ala Thr Glu Ser Ser Val Lys Lys Asp Thr
            165                 170                 175
Lys Lys Lys Pro Lys Pro Ser Asn Arg Asp Gly Ile Asn Lys Asp Lys
            180             185                 190
Ile Val Tyr Asp Arg Thr Asn Ile Asn Tyr Asn Glu Leu Met Lys Thr
            195                 200                 205
Leu Lys Gln Ala Glu Ser Tyr Ile Lys Ser Lys Val Asn Thr Gly Thr
            210                 215                 220
Asp Phe Asp Gly Leu Tyr Gly Tyr Gln Cys Met Asp Leu Ala Val Asp
225                 230                 235                 240
Tyr Ile Tyr His Val Thr Asp Gly Lys Ile Arg Met Trp Gly Asn Ala
                245                 250                 255
Lys Asp Ala Ile Asn Asn Ser Phe Gly Gly Thr Ala Thr Val Tyr Lys
                260                 265                 270
Asn Tyr Pro Ala Phe Arg Pro Lys Tyr Gly Asp Val Val Trp Thr
            275                 280                 285
Thr Gly Asn Phe Ala Thr Tyr Gly His Ile Ala Ile Val Thr Asn Pro
            290                 295                 300
Asp Pro Tyr Gly Asp Leu Gln Tyr Val Thr Val Leu Glu Gln Asn Trp
305                 310                 315                 320
Asn Gly Asn Gly Ile Tyr Lys Thr Glu Leu Ala Thr Ile Arg Thr His
                325                 330                 335
Asp Tyr Thr Gly Ile Thr His Phe Ile Arg Pro Asn Phe Ala Thr Glu
                340                 345                 350
Ser Ser Val Lys Lys Asp Thr Lys Lys Pro Lys Pro Ser Asn
            355                 360                 365
Arg Asp Gly Ile Asn Lys Asp Lys Ile Val Tyr Asp Arg Thr Asn Ile
370                 375                 380
Asn Tyr Asn Gly Lys Ser Ala Ser Lys Ile Thr Val Gly Ser Lys Ala
385                 390                 395                 400
Pro Tyr Asn Leu Lys Trp Ser Lys Gly Ala Tyr Phe Asn Ala Lys Ile
                405                 410                 415
Asp Gly Leu Gly Ala Thr Ser Ala Thr Arg Tyr Gly Asp Asn Arg Thr
                420                 425                 430
Asn Tyr Arg Phe Asp Val Gly Gln Ala Val Tyr Ala Pro Gly Thr Leu
                435                 440                 445
Ile Tyr Val Phe Glu Ile Ile Asp Gly Trp Cys Arg Ile Tyr Trp Asn
                450                 455                 460
Asn His Asn Glu Trp Ile Trp His Glu Arg Leu Ile Val Lys Glu Val
465                 470                 475                 480
Phe

<210> SEQ ID NO 67
<211> LENGTH: 1278
<212> TYPE: DNA
<213> ORGANISM: artificial
<220> FEATURE:
<223> OTHER INFORMATION: artificial construct

<400> SEQUENCE: 67
atgagaggat cgcatcacca tcaccatcac ggatctggct ctggatctgg tatcgaggga    60
agggctgcaa cacatgaaca ttcagcacaa tggttgaata attacaaaaa aggatatggt   120
tacggtcctt atccattagg tataaatggc ggtatgcact acggagttga tttttttatg   180
aatattggaa caccagtaaa agctatttca agcggaaaaa tagttgaagc tggttggagt   240

```
aattacggag gaggtaatca aataggtctt attgaaaatg atggagtgca tagacaatgg    300
tatatgcatc taagtaaata taatgttaaa gtaggagatt atgtcaaagc tggtcaaata    360
atcggttggt ctggaagcac tggttattct acagcaccac atttacactt ccaaagaatg    420
gttaattcat tttcaaattc aactgcccaa gatccaatgc ctttcttaaa gagcgcagga    480
tatggaaaag caggtggtac agtaactcca acgccgaata caggtgagct cgctgcaaca    540
catgaacatt cagcacaatg gttgaataat tacaaaaaag gatatggtta cggtccttat    600
ccattaggta taaatggcgg tatgcactac ggagttgatt tttttatgaa tattggaaca    660
ccagtaaaag ctatttcaag cggaaaaata gttgaagctg gttggagtaa ttacggagga    720
ggtaatcaaa taggtcttat tgaaaatgat ggagtgcata caatggta tatgcatcta     780 agtaaatata atgttaaagt aggagattat gtcaaagctg gtcaaataat cggttggtct    840
ggaagcactg gttattctac agcaccacat ttacacttcc aaagaatggt taattcattt    900
tcaaattcaa ctgcccaaga tccaatgcct tcttaaaga gcgcaggata tggaaaagca    960
ggtggtacag taactccaac gccgaataca ggttggaaac agaataaaga tggcatttgg   1020
tataaagctg aacatgcttc gttcacagtg acagcaccag agggaattat cacaagatac   1080
aaaggtcctt ggactggtca cccacaagct ggtgtattac aaaaaggtca aacgattaaa   1140
tatgatgagg ttcaaaaatt tgacggtcat gtttgggtat cgtggaaac gtttgagggc    1200 gaaactgtat acatgccggt acgcacatgg gacgctaaaa ctggtaaagt tggtaagttg   1260 tgggggcgaaa ttaaataa                                                 1278
```

<210> SEQ ID NO 68
<211> LENGTH: 425
<212> TYPE: PRT
<213> ORGANISM: artificial
<220> FEATURE:
<223> OTHER INFORMATION: artificial construct

<400> SEQUENCE: 68

```
Met Arg Gly Ser His His His His His His Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Glu
                165                 170                 175
```

Leu Ala Ala Thr His Glu His Ser Ala Gln Trp Leu Asn Asn Tyr Lys
            180                 185                 190
Lys Gly Tyr Gly Tyr Gly Pro Tyr Pro Leu Gly Ile Asn Gly Gly Met
        195                 200                 205
His Tyr Gly Val Asp Phe Phe Met Asn Ile Gly Thr Pro Val Lys Ala
    210                 215                 220
Ile Ser Ser Gly Lys Ile Val Glu Ala Gly Trp Ser Asn Tyr Gly Gly
225                 230                 235                 240
Gly Asn Gln Ile Gly Leu Ile Glu Asn Asp Gly Val His Arg Gln Trp
                245                 250                 255
Tyr Met His Leu Ser Lys Tyr Asn Val Lys Val Gly Asp Tyr Val Lys
            260                 265                 270
Ala Gly Gln Ile Ile Gly Trp Ser Gly Ser Thr Gly Tyr Ser Thr Ala
        275                 280                 285
Pro His Leu His Phe Gln Arg Met Val Asn Ser Phe Ser Asn Ser Thr
    290                 295                 300
Ala Gln Asp Pro Met Pro Phe Leu Lys Ser Ala Gly Tyr Gly Lys Ala
305                 310                 315                 320
Gly Gly Thr Val Thr Pro Thr Pro Asn Thr Gly Trp Lys Gln Asn Lys
                325                 330                 335
Asp Gly Ile Trp Tyr Lys Ala Glu His Ala Ser Phe Thr Val Thr Ala
            340                 345                 350
Pro Glu Gly Ile Ile Thr Arg Tyr Lys Gly Pro Trp Thr Gly His Pro
        355                 360                 365
Gln Ala Gly Val Leu Gln Lys Gly Gln Thr Ile Lys Tyr Asp Glu Val
    370                 375                 380
Gln Lys Phe Asp Gly His Val Trp Val Ser Trp Glu Thr Phe Glu Gly
385                 390                 395                 400
Glu Thr Val Tyr Met Pro Val Arg Thr Trp Asp Ala Lys Thr Gly Lys
                405                 410                 415
Val Gly Lys Leu Trp Gly Glu Ile Lys
            420                 425

<210> SEQ ID NO 69
<211> LENGTH: 1272
<212> TYPE: DNA
<213> ORGANISM: artificial
<220> FEATURE:
<223> OTHER INFORMATION: artificial construct

<400> SEQUENCE: 69
atgagaggat cgcatcacca tcaccatcac ggatctggct ctggatctgg tatcgaggga    60
agggctgcaa cacatgaaca ttcagcacaa tggttgaata attacaaaaa aggatatggt   120
tacggtcctt atccattagg tataaatggc ggtatgcact acggagttga ttttttatg   180 aatattggaa caccagtaaa agctatttca agcggaaaaa tagttgaagc tggttggagt   240
aattacggag gaggtaatca aataggtctt attgaaaatg atggagtgca tagacaatgg   300
tatatgcatc taagtaaata taatgttaaa gtaggagatt atgtcaaagc tggtcaaata   360
atcggttggt ctggaagcac tggttattct acagcaccac atttacactt ccaaagaatg   420
gttaattcat tttcaaattc aactgcccaa gatccaatgc ctttcttaaa gagcgcagga   480
tatggaaaag caggtggtac agtaactcca acgccgaata caggtgagct cgctgcaaca   540
catgaacatt cagcacaatg gttgaataat tacaaaaaag gatatggtta cggtccttat   600

```
ccattaggta taaatggcgg tatgcactac ggagttgatt tttttatgaa tattggaaca      660
ccagtaaaag ctatttcaag cggaaaaata gttgaagctg gttggagtaa ttacggagga      720
ggtaatcaaa taggtcttat tgaaaatgat ggagtgcata gacaatggta tatgcatcta      780
agtaaatata atgttaaagt aggagattat gtcaaagctg gtcaaataat cggttggtct      840
ggaagcactg gttattctac agcaccacat ttacacttcc aaagaatggt taattcattt      900
tcaaattcaa ctgcccaaga tccaatgcct ttcttaaaga gcgcaggata tggaaaagca      960
ggtggtacag taactccaac gccgaataca ggttggaaaa caaacaaata tggcacacta     1020
tataaatcag agtcagctag cttcacacct aatacagata taataacaag aacgactggt     1080
ccatttagaa gcatgccgca gtcaggagtc ttaaaagcag gtcaaacaat tcattatgat     1140
gaagtgatga acaagacgg tcatgtttgg gtaggttata caggtaacag tggccaacgt     1200
atttacttgc ctgtaagaac atggaataaa tctactaata ctttaggtgt tctttgggga     1260
actataaagt aa                                                         1272
```

<210> SEQ ID NO 70
<211> LENGTH: 423
<212> TYPE: PRT
<213> ORGANISM: artificial
<220> FEATURE:
<223> OTHER INFORMATION: artificial construct

<400> SEQUENCE: 70

```
Met Arg Gly Ser His His His His His Gly Ser Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Glu
                165                 170                 175

Leu Ala Ala Thr His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220

Ile Ser Ser Gly Lys Ile Val Glu Ala Gly Trp Ser Asn Tyr Gly Gly
225                 230                 235                 240
```

```
Gly Asn Gln Ile Gly Leu Ile Glu Asn Asp Gly Val His Arg Gln Trp
            245                 250                 255
Tyr Met His Leu Ser Lys Tyr Asn Val Lys Val Gly Asp Tyr Val Lys
        260                 265                 270
Ala Gly Gln Ile Ile Gly Trp Ser Gly Ser Thr Gly Tyr Ser Thr Ala
        275                 280                 285
Pro His Leu His Phe Gln Arg Met Val Asn Ser Phe Ser Asn Ser Thr
        290                 295                 300
Ala Gln Asp Pro Met Pro Phe Leu Lys Ser Ala Gly Tyr Gly Lys Ala
305                 310                 315                 320
Gly Gly Thr Val Thr Pro Thr Pro Asn Thr Gly Trp Lys Thr Asn Lys
            325                 330                 335
Tyr Gly Thr Leu Tyr Lys Ser Glu Ser Ala Ser Phe Thr Pro Asn Thr
            340                 345                 350
Asp Ile Ile Thr Arg Thr Thr Gly Pro Phe Arg Ser Met Pro Gln Ser
            355                 360                 365
Gly Val Leu Lys Ala Gly Gln Thr Ile His Tyr Asp Glu Val Met Lys
        370                 375                 380
Gln Asp Gly His Val Trp Val Gly Tyr Thr Gly Asn Ser Gly Gln Arg
385                 390                 395                 400
Ile Tyr Leu Pro Val Arg Thr Trp Asn Lys Ser Thr Asn Thr Leu Gly
            405                 410                 415
Val Leu Trp Gly Thr Ile Lys
            420

<210> SEQ ID NO 71
<211> LENGTH: 1278
<212> TYPE: DNA
<213> ORGANISM: artificial
<220> FEATURE:
<223> OTHER INFORMATION: artificial construct

<400> SEQUENCE: 71
atgagaggat cgcatcacca tcaccatcac ggatctggct ctggatctgg tatcgaggga      60
agggctgcaa cacatgaaca ttcagcacaa tggttgaata attacaaaaa aggatatggt     120
tacggtcctt atccattagg tataaatggc ggtatgcact acggagttga ttttttttatg    180
aatattggaa caccagtaaa agctatttca agcggaaaaa tagttgaagc tggttggagt     240
aattacggag gaggtaatca aataggtctt attgaaaatg atggagtgca tagacaatgg     300
tatatgcatc taagtaaata taatgttaaa gtaggagatt atgtcaaagc tggtcaaata     360
atcggttggt ctggaagcac tggttattct acagcaccac atttacactt ccaaagaatg     420
gttaattcat ttcaaattc aactgcccaa gatccaatgc ctttcttaaa gagcgcagga     480
tatggaaaag caggtggtac agtaactcca acgccgaata caggtgagct cgctgcaaca     540
catgaacatt cagcacaatg gttgaataat tacaaaaaag gatatggtta cggtccttat     600
ccattaggta taaatggcgg tatgcactac ggagttgatt ttttatgaa tattggaaca     660
ccagtaaaag ctatttcaag cggaaaaata gttgaagctg gttggagtaa ttacggagga     720
ggtaatcaaa taggtcttat tgaaaatgat ggagtgcata gacaatggta tatgcatcta     780
agtaaatata atgttaaagt aggagattat gtcaaagctg gtcaaataat cggttggtct     840
ggaagcactg gttattctac agcaccacat ttacacttcc aaagaatggt taattcattt     900
caaattcaa ctgcccaaga tccaatgcct ttcttaaaga gcgcaggata tggaaaagca     960
ggtggtacag taactccaac gccgaataca ggtggtaaat ctgcaagtaa aataacagtt    1020
```

```
ggaagtaaag cgccttataa ccttaaatgg tcaaaaggtg cttattttaa tgcgaaaatc    1080
gacggcttag gtgctacttc agccactaga tacggtgata atcgtactaa ctatagattc    1140
gatgttggac aggctgtata cgcgcctgga acattaatat atgtgtttga aattatagat    1200
ggttggtgtc gcatttattg gaacaatcat aatgagtgga tatggcatga gagattgatt    1260
gtgaaagaag tgttttaa                                                  1278
```

<210> SEQ ID NO 72
<211> LENGTH: 425
<212> TYPE: PRT
<213> ORGANISM: artificial
<220> FEATURE:
<223> OTHER INFORMATION: artificial construct

<400> SEQUENCE: 72

```
Met Arg Gly Ser His His His His His Gly Ser Gly Ser Gly Ser
1               5                   10                  15

Gly Ile Glu Gly Arg Ala Ala Thr His Glu His Ser Ala Gln Trp Leu
            20                  25                  30

Asn Asn Tyr Lys Lys Gly Tyr Gly Tyr Gly Pro Tyr Pro Leu Gly Ile
        35                  40                  45

Asn Gly Gly Met His Tyr Gly Val Asp Phe Phe Met Asn Ile Gly Thr
    50                  55                  60

Pro Val Lys Ala Ile Ser Ser Gly Lys Ile Val Glu Ala Gly Trp Ser
65                  70                  75                  80

Asn Tyr Gly Gly Gly Asn Gln Ile Gly Leu Ile Glu Asn Asp Gly Val
                85                  90                  95

His Arg Gln Trp Tyr Met His Leu Ser Lys Tyr Asn Val Lys Val Gly
            100                 105                 110

Asp Tyr Val Lys Ala Gly Gln Ile Ile Gly Trp Ser Gly Ser Thr Gly
        115                 120                 125

Tyr Ser Thr Ala Pro His Leu His Phe Gln Arg Met Val Asn Ser Phe
    130                 135                 140

Ser Asn Ser Thr Ala Gln Asp Pro Met Pro Phe Leu Lys Ser Ala Gly
145                 150                 155                 160

Tyr Gly Lys Ala Gly Gly Thr Val Thr Pro Thr Pro Asn Thr Gly Glu
                165                 170                 175

Leu Ala Ala Thr His Glu His Ser Ala Gln Trp Leu Asn Asn Tyr Lys
            180                 185                 190

Lys Gly Tyr Gly Tyr Gly Pro Tyr Pro Leu Gly Ile Asn Gly Gly Met
        195                 200                 205

His Tyr Gly Val Asp Phe Phe Met Asn Ile Gly Thr Pro Val Lys Ala
    210                 215                 220

Ile Ser Ser Gly Lys Ile Val Glu Ala Gly Trp Ser Asn Tyr Gly Gly
225                 230                 235                 240

Gly Asn Gln Ile Gly Leu Ile Glu Asn Asp Gly Val His Arg Gln Trp
                245                 250                 255

Tyr Met His Leu Ser Lys Tyr Asn Val Lys Val Gly Asp Tyr Val Lys
            260                 265                 270

Ala Gly Gln Ile Ile Gly Trp Ser Gly Ser Thr Gly Tyr Ser Thr Ala
        275                 280                 285

Pro His Leu His Phe Gln Arg Met Val Asn Ser Phe Ser Asn Ser Thr
    290                 295                 300

Ala Gln Asp Pro Met Pro Phe Leu Lys Ser Ala Gly Tyr Gly Lys Ala
```

```
                305                 310                 315                 320
Gly Gly Thr Val Thr Pro Thr Pro Asn Thr Gly Gly Lys Ser Ala Ser
                325                 330                 335

Lys Ile Thr Val Gly Ser Lys Ala Pro Tyr Asn Leu Lys Trp Ser Lys
                340                 345                 350

Gly Ala Tyr Phe Asn Ala Lys Ile Asp Gly Leu Gly Ala Thr Ser Ala
                355                 360                 365

Thr Arg Tyr Gly Asp Asn Arg Thr Asn Tyr Arg Phe Asp Val Gly Gln
                370                 375                 380

Ala Val Tyr Ala Pro Gly Thr Leu Ile Tyr Val Phe Glu Ile Ile Asp
385                 390                 395                 400

Gly Trp Cys Arg Ile Tyr Trp Asn Asn His Asn Glu Trp Ile Trp His
                405                 410                 415

Glu Arg Leu Ile Val Lys Glu Val Phe
                420                 425

<210> SEQ ID NO 73
<211> LENGTH: 63
<212> TYPE: DNA
<213> ORGANISM: artificial
<220> FEATURE:
<223> OTHER INFORMATION: artificial his-tag

<400> SEQUENCE: 73
atgagaggat cgcatcacca tcaccatcac ggatctggct ctggatctgg tatcgaggga      60
agg                                                                    63

<210> SEQ ID NO 74
<211> LENGTH: 21
<212> TYPE: PRT
<213> ORGANISM: artificial
<220> FEATURE:
<223> OTHER INFORMATION: artificial Hist-tag

<400> SEQUENCE: 74

Met Arg Gly Ser His His His His His His Gly Ser Gly Ser Gly Ser
1               5                   10                  15

Gly Ile Glu Gly Arg
            20

<210> SEQ ID NO 75
<211> LENGTH: 741
<212> TYPE: DNA
<213> ORGANISM: Staphylococcus simulans

<400> SEQUENCE: 75
gctgcaacac atgaacattc agcacaatgg ttgaataatt acaaaaaagg atatggttac      60
ggtccttatc cattaggtat aaatggcggt atgcactacg agttgatttt ttttatgaat     120
attggaacac cagtaaaagc tatttcaagc ggaaaaatag ttgaagctgg ttggagtaat     180
tacggaggag gtaatcaaat aggtcttatt gaaaatgatg gagtgcatag acaatggtat     240
atgcatctaa gtaaatataa tgttaaagta ggagattatg tcaaagctgg tcaaataatc     300
ggttggtctg gaagcactgg ttattctaca gcaccacatt tacacttcca agaatggtt      360 aattcatttt caaattcaac tgcccaagat ccaatgcctt tcttaaagag cgcaggatat     420
ggaaaagcag gtggtacagt aactccaacg ccgaatacag ttggaaaaac aaacaaatat     480
ggcacactat ataatcaga gtcagctagc ttcacaccta atacagatat aataacaaga     540
```

```
acgactggtc catttagaag catgccgcag tcaggagtct taaaagcagg tcaaacaatt    600
cattatgatg aagtgatgaa acaagacggt catgtttggg taggttatac aggtaacagt    660
ggccaacgta tttacttgcc tgtaagaaca tggaataaat ctactaatac tttaggtgtt    720
ctttggggaa ctataaagtg a                                              741
```

<210> SEQ ID NO 76
<211> LENGTH: 246
<212> TYPE: PRT
<213> ORGANISM: Staphylococcus simulans

<400> SEQUENCE: 76

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30

Tyr Gly Val Asp Phe Phe Met Asn Ile Gly Thr Pro Val Lys Ala Ile
        35                  40                  45

Ser Ser Gly Lys Ile Val Glu Ala Gly Trp Ser Asn Tyr Gly Gly Gly
    50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr Gly Lys Ala Gly
    130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245
```

<210> SEQ ID NO 77
<211> LENGTH: 2019
<212> TYPE: DNA
<213> ORGANISM: artificial
<220> FEATURE:
<223> OTHER INFORMATION: artificial construct

<400> SEQUENCE: 77

```
atgagaggat cgcatcacca tcaccatcac ggatccatgc aagcaaaatt aactaaaaat     60
gagtttatag agtggttgaa aacttctgag ggaaaacaat tcaatgtgga cttatggtat    120
ggatttcaat gctttgatta tgccaatgct ggttggaaag ttttgtttgg attacttcta    180
```

```
aaaggtttag gtgcaaaaga tattccgttc gctaacaact tcgacggatt agctactgta    240
taccaaaata caccggactt cttagcacaa cctggcgaca tggtggtatt cggtagcaac    300
tacggtgctg gatatggtca cgttgcatgg gtaattgaag caactttaga ttacatcatt    360
gtatatgagc agaattggct aggcggtggc tggactgacg gaatcgaaca acccggctgg    420
ggttgggaaa aagttacaag acgacaacat gcttatgatt tccctatgtg gtttatccgt    480
ccgaatttta aaagtgagac agcgccacga tcagttcaat ctcctacaca agcacctaaa    540
aaagaaacag ctggatccat gctaactgct attgactatc ttacgaaaaa aggttggaaa    600
atatcatctg accctcgcac ttacgatggt taccctaaaa actacggcta cagaaattac    660
catgaaaacg gcattaatta tgatgagttt tgtggtggtt atcatagagc ttttgatgtt    720
tacagtaacg aaactaacga cgtgcctgct gttactagcg gaacagttat tgaagcaaac    780
gattacggta attttggtgg tacattcgtt attagagacg ctaacgataa cgattggata    840
tatgggcatc tacaacgtgg ctcaatgcga tttgttgtag cgacaaagt caatcaaggt    900 gacattattg gtttacaagg taatagcaac tattacgaca atcctatgag tgtacattta    960
catttacaat tacgccctaa agacgcaaag aaagatgaaa aatcacaagt atgtagtggt    1020
ttggctatgg aaaaatatga cattacaaat ttaaatgcta acaagataa atcaaagaat    1080 gggagcgtga aagagttgaa acatatctat tcaaaccata ttaaaggtaa caagattaca    1140
gcaccaaaac ctagtattca aggtgtggtc atccacaatg attatggtag tatgacacct    1200
agtcaatact taccatggtt atatgcacgt gagaataacg gtacacacgt taacggttgg    1260
gctagtgttt atgcaaatag aaacgaagtg cttttggtatc atccgacaga ctacgtagag    1320
tggcattgtg gtaatcaatg ggcaaatgct aacttaatcg gatttgaagt gtgtgagtcg    1380
tatcctggta gaatctcgga caaattattc ttagaaaatg aagaagcgac attgaaagta    1440
gctgcggatg tgatgaagtc gtacggatta ccagttaatc gcaacactgt acgtctgcat    1500
aacgaattct tcggaacttc ttgtccacat cgttcgtggg acttgcatgt tggcaaaggt    1560
gagccttaca caactactaa tattaataaa atgaaagact acttcatcaa acgcatcaaa    1620
cattattatg acggtggaaa gctagaagta agcaaagcag caactatcaa acaatctgac    1680
gttaagcaag aagttaaaaa gcaagaagca aaacaaattg tgaaagcaac agattggaaa    1740
cagaataaag atggcatttg gtataaagct gaacatgctt cgttcacagt gacagcacca    1800
gagggaatta tcacaagata caaaggtcct tggactggtc acccacaagc tggtgtatta    1860
caaaaaggtc aaacgattaa atatgatgag gttcaaaaat ttgacggtca tgtttggta    1920 tcgtgggaaa cgtttgaggg cgaaactgta tacatgccgg tacgcacatg ggacgctaaa    1980
actggtaaag ttggtaagtt gtggggcgaa attaaataa                          2019
```

<210> SEQ ID NO 78
<211> LENGTH: 672
<212> TYPE: PRT
<213> ORGANISM: artificial
<220> FEATURE:
<223> OTHER INFORMATION: artificial construct

<400> SEQUENCE: 78

Met Arg Gly Ser His His His His His His Gly Ser Met Gln Ala Lys
1               5                   10                  15

Leu Thr Lys Asn Glu Phe Ile Glu Trp Leu Lys Thr Ser Glu Gly Lys
            20                  25                  30

```
Gln Phe Asn Val Asp Leu Trp Tyr Gly Phe Gln Cys Phe Asp Tyr Ala
            35                  40                  45

Asn Ala Gly Trp Lys Val Leu Phe Gly Leu Leu Leu Lys Gly Leu Gly
 50                  55                  60

Ala Lys Asp Ile Pro Phe Ala Asn Asn Phe Asp Gly Leu Ala Thr Val
 65                  70                  75                  80

Tyr Gln Asn Thr Pro Asp Phe Leu Ala Gln Pro Gly Asp Met Val Val
                 85                  90                  95

Phe Gly Ser Asn Tyr Gly Ala Gly Tyr Gly His Val Ala Trp Val Ile
            100                 105                 110

Glu Ala Thr Leu Asp Tyr Ile Ile Val Tyr Glu Gln Asn Trp Leu Gly
            115                 120                 125

Gly Gly Trp Thr Asp Gly Ile Glu Gln Pro Gly Trp Gly Trp Glu Lys
            130                 135                 140

Val Thr Arg Arg Gln His Ala Tyr Asp Phe Pro Met Trp Phe Ile Arg
145                 150                 155                 160

Pro Asn Phe Lys Ser Glu Thr Ala Pro Arg Ser Val Gln Ser Pro Thr
                165                 170                 175

Gln Ala Pro Lys Lys Glu Thr Ala Gly Ser Met Leu Thr Ala Ile Asp
            180                 185                 190

Tyr Leu Thr Lys Lys Gly Trp Lys Ile Ser Ser Asp Pro Arg Thr Tyr
            195                 200                 205

Asp Gly Tyr Pro Lys Asn Tyr Gly Tyr Arg Asn Tyr His Glu Asn Gly
            210                 215                 220

Ile Asn Tyr Asp Glu Phe Cys Gly Gly Tyr His Arg Ala Phe Asp Val
225                 230                 235                 240

Tyr Ser Asn Glu Thr Asn Asp Val Pro Ala Val Thr Ser Gly Thr Val
                245                 250                 255

Ile Glu Ala Asn Asp Tyr Gly Asn Phe Gly Gly Thr Phe Val Ile Arg
            260                 265                 270

Asp Ala Asn Asp Asn Asp Trp Ile Tyr Gly His Leu Gln Arg Gly Ser
            275                 280                 285

Met Arg Phe Val Val Gly Asp Lys Val Asn Gln Gly Asp Ile Ile Gly
290                 295                 300

Leu Gln Gly Asn Ser Asn Tyr Tyr Asp Asn Pro Met Ser Val His Leu
305                 310                 315                 320

His Leu Gln Leu Arg Pro Lys Asp Ala Lys Lys Asp Glu Lys Ser Gln
                325                 330                 335

Val Cys Ser Gly Leu Ala Met Glu Lys Tyr Asp Ile Thr Asn Leu Asn
            340                 345                 350

Ala Lys Gln Asp Lys Ser Lys Asn Gly Ser Val Lys Glu Leu Lys His
            355                 360                 365

Ile Tyr Ser Asn His Ile Lys Gly Asn Lys Ile Thr Ala Pro Lys Pro
370                 375                 380

Ser Ile Gln Gly Val Val Ile His Asn Asp Tyr Gly Ser Met Thr Pro
385                 390                 395                 400

Ser Gln Tyr Leu Pro Trp Leu Tyr Ala Arg Glu Asn Asn Gly Thr His
                405                 410                 415

Val Asn Gly Trp Ala Ser Val Tyr Ala Asn Arg Asn Glu Val Leu Trp
            420                 425                 430

Tyr His Pro Thr Asp Tyr Val Glu Trp His Cys Gly Asn Gln Trp Ala
            435                 440                 445

Asn Ala Asn Leu Ile Gly Phe Glu Val Cys Glu Ser Tyr Pro Gly Arg
```

```
                   450                  455                  460
Ile Ser Asp Lys Leu Phe Leu Glu Asn Glu Ala Thr Leu Lys Val
465                  470                  475                  480

Ala Ala Asp Val Met Lys Ser Tyr Gly Leu Pro Val Asn Arg Asn Thr
                        485                  490                  495

Val Arg Leu His Asn Glu Phe Phe Gly Thr Ser Cys Pro His Arg Ser
                500                  505                  510

Trp Asp Leu His Val Gly Lys Gly Glu Pro Tyr Thr Thr Thr Asn Ile
            515                  520                  525

Asn Lys Met Lys Asp Tyr Phe Ile Lys Arg Ile Lys His Tyr Tyr Asp
        530                  535                  540

Gly Gly Lys Leu Glu Val Ser Lys Ala Ala Thr Ile Lys Gln Ser Asp
545                  550                  555                  560

Val Lys Gln Glu Val Lys Lys Gln Glu Ala Lys Gln Ile Val Lys Ala
                565                  570                  575

Thr Asp Trp Lys Gln Asn Lys Asp Gly Ile Trp Tyr Lys Ala Glu His
                580                  585                  590

Ala Ser Phe Thr Val Thr Ala Pro Glu Gly Ile Ile Thr Arg Tyr Lys
                595                  600                  605

Gly Pro Trp Thr Gly His Pro Gln Ala Gly Val Leu Gln Lys Gly Gln
            610                  615                  620

Thr Ile Lys Tyr Asp Glu Val Gln Lys Phe Asp Gly His Val Trp Val
625                  630                  635                  640

Ser Trp Glu Thr Phe Glu Gly Glu Thr Val Tyr Met Pro Val Arg Thr
                645                  650                  655

Trp Asp Ala Lys Thr Gly Lys Val Gly Lys Leu Trp Gly Glu Ile Lys
                660                  665                  670

<210> SEQ ID NO 79
<211> LENGTH: 2145
<212> TYPE: DNA
<213> ORGANISM: artificial
<220> FEATURE:
<223> OTHER INFORMATION: artificial construct

<400> SEQUENCE: 79
atgagaggat cgcatcacca tcaccatcac ggatccaagc cacaacctaa agcagtagaa      60
cttaaaatca tcaaagatgt ggttaaaggt tatgacctac ctaagcgtgg tagtaaccct     120
aaaggtatag ttatacacaa cgacgcaggg agcaaagggg cgactgctga agcatatcgt     180
aacggattag taaatgcacc tttatcaaga ttagaagcgg gcattgcgca tagttacgta     240
tcaggcaaca cagtttggca agccttagat gaatcacaag taggttggca taccgctaat     300
caaataggta ataaatatta ttacggtatt gaagtatgtc aatcaatggg cgcagataac     360
gcgacattct taaaaaatga acaggcaact ttccaagaat cgctagatt gttgaaaaaa      420
tgggattac cagcaaacag aaatacaatc agattgcaca atgaatttac ttcaacatca     480
tgccctcata gaagttcggt tttacacact ggttttgacc cagtaactcg cggtctattg     540
ccagaagaca agcggttgca acttaaagac tactttatca agcagattag ggcgtacatg     600
gatggtaaaa taccggttgc cactgtctct aatgagtcaa gcgcttcaag taatacagtt     660
aaaccagttg caagtgcagg atccatgcta actgctattg actatcttac gaaaaaaggt     720
tggaaaatat catctgaccc tcgcacttac gatggttacc ctaaaaacta cggctacaga     780
aattaccatg aaaacggcat taattatgat gagttttgtg gtggttatca tagagctttt     840
```

```
gatgtttaca gtaacgaaac taacgacgtg cctgctgtta ctagcggaac agttattgaa    900
gcaaacgatt acggtaattt tggtggtaca ttcgttatta gagacgctaa cgataacgat    960
tggatatatg ggcatctaca acgtggctca atgcgatttg ttgtaggcga caaagtcaat   1020
caaggtgaca ttattggttt acaaggtaat agcaactatt acgacaatcc tatgagtgta   1080
catttacatt tacaattacg ccctaaagac gcaaagaaag atgaaaaatc acaagtatgt   1140
agtggtttgg ctatggaaaa atatgacatt acaaatttaa atgctaaaca agataaaatca  1200
aagaatggga gcgtgaaaga gttgaaacat atctattcaa accatattaa aggtaacaag   1260
attacagcac caaaacctag tattcaaggt gtggtcatcc acaatgatta tggtagtatg   1320
acacctagtc aatacttacc atggttatat gcacgtgaga ataacggtac acacgttaac   1380
ggttgggcta gtgtttatgc aaatagaaac gaagtgcttt ggtatcatcc gacagactac   1440
gtagagtggc attgtggtaa tcaatgggca aatgctaact taatcggatt tgaagtgtgt   1500
gagtcgtatc ctggtagaat ctcggacaaa ttattcttag aaaatgaaga agcgacattg   1560
aaagtagctg cggatgtgat gaagtcgtac ggattaccag ttaatcgcaa cactgtacgt   1620
ctgcataacg aattcttcgg aacttcttgt ccacatcgtt cgtgggactt gcatgttggc   1680
aaaggtgagc cttacacaac tactaatatt aataaaatga agactactt catcaaacgc    1740
atcaaacatt attatgacgg tggaaagcta gaagtaagca agcagcaac tatcaaacaa   1800
tctgacgtta agcaagaagt taaaaagcaa gaagcaaaac aaattgtgaa agcaacagat   1860
tggaaacaga ataaagatgg catttggtat aaagctgaac atgcttcgtt cacagtgaca   1920
gcaccgagg gaattatcac aagatacaaa ggtccttgga ctggtcaccc acaagctggt   1980
gtattacaaa aaggtcaaac gattaaatat gatgaggttc aaaaatttga cggtcatgtt   2040
tgggtatcgt gggaaacgtt tgagggcgaa actgtataca tgccggtacg cacatgggac   2100
gctaaaactg gtaaagttgg taagttgtgg ggcgaaatta aataa                   2145
```

<210> SEQ ID NO 80
<211> LENGTH: 714
<212> TYPE: PRT
<213> ORGANISM: artificial
<220> FEATURE:
<223> OTHER INFORMATION: artificial construct

<400> SEQUENCE: 80

```
Met Arg Gly Ser His His His His His His Gly Ser Lys Pro Gln Pro
  1               5                  10                  15

Lys Ala Val Glu Leu Lys Ile Ile Lys Asp Val Val Lys Gly Tyr Asp
             20                  25                  30

Leu Pro Lys Arg Gly Ser Asn Pro Lys Gly Ile Val Ile His Asn Asp
         35                  40                  45

Ala Gly Ser Lys Gly Ala Thr Ala Glu Ala Tyr Arg Asn Gly Leu Val
     50                  55                  60

Asn Ala Pro Leu Ser Arg Leu Glu Ala Gly Ile Ala His Ser Tyr Val
 65                  70                  75                  80

Ser Gly Asn Thr Val Trp Gln Ala Leu Asp Glu Ser Gln Val Gly Trp
                 85                  90                  95

His Thr Ala Asn Gln Ile Gly Asn Lys Tyr Tyr Gly Ile Glu Val
            100                 105                 110

Cys Gln Ser Met Gly Ala Asp Asn Ala Thr Phe Leu Lys Asn Glu Gln
        115                 120                 125

Ala Thr Phe Gln Glu Cys Ala Arg Leu Leu Lys Lys Trp Gly Leu Pro
```

```
            130                 135                 140
Ala Asn Arg Asn Thr Ile Arg Leu His Asn Glu Phe Thr Ser Thr Ser
145                 150                 155                 160

Cys Pro His Arg Ser Ser Val Leu His Thr Gly Phe Asp Pro Val Thr
                165                 170                 175

Arg Gly Leu Leu Pro Glu Asp Lys Arg Leu Gln Leu Lys Asp Tyr Phe
            180                 185                 190

Ile Lys Gln Ile Arg Ala Tyr Met Asp Gly Lys Ile Pro Val Ala Thr
        195                 200                 205

Val Ser Asn Glu Ser Ser Ala Ser Ser Asn Thr Val Lys Pro Val Ala
    210                 215                 220

Ser Ala Gly Ser Met Leu Thr Ala Ile Asp Tyr Leu Thr Lys Lys Gly
225                 230                 235                 240

Trp Lys Ile Ser Ser Asp Pro Arg Thr Tyr Asp Gly Tyr Pro Lys Asn
                245                 250                 255

Tyr Gly Tyr Arg Asn Tyr His Glu Asn Gly Ile Asn Tyr Asp Glu Phe
            260                 265                 270

Cys Gly Gly Tyr His Arg Ala Phe Asp Val Tyr Ser Asn Glu Thr Asn
        275                 280                 285

Asp Val Pro Ala Val Thr Ser Gly Thr Val Ile Glu Ala Asn Asp Tyr
    290                 295                 300

Gly Asn Phe Gly Gly Thr Phe Val Ile Arg Asp Ala Asn Asp Asn Asp
305                 310                 315                 320

Trp Ile Tyr Gly His Leu Gln Arg Gly Ser Met Arg Phe Val Val Gly
                325                 330                 335

Asp Lys Val Asn Gln Gly Asp Ile Ile Gly Leu Gln Gly Asn Ser Asn
            340                 345                 350

Tyr Tyr Asp Asn Pro Met Ser Val His Leu His Leu Gln Leu Arg Pro
        355                 360                 365

Lys Asp Ala Lys Lys Asp Glu Lys Ser Gln Val Cys Ser Gly Leu Ala
    370                 375                 380

Met Glu Lys Tyr Asp Ile Thr Asn Leu Asn Ala Lys Gln Asp Lys Ser
385                 390                 395                 400

Lys Asn Gly Ser Val Lys Glu Leu Lys His Ile Tyr Ser Asn His Ile
                405                 410                 415

Lys Gly Asn Lys Ile Thr Ala Pro Lys Pro Ser Ile Gln Gly Val Val
            420                 425                 430

Ile His Asn Asp Tyr Gly Ser Met Thr Pro Ser Gln Tyr Leu Pro Trp
        435                 440                 445

Leu Tyr Ala Arg Glu Asn Asn Gly Thr His Val Asn Gly Trp Ala Ser
    450                 455                 460

Val Tyr Ala Asn Arg Asn Glu Val Leu Trp Tyr His Pro Thr Asp Tyr
465                 470                 475                 480

Val Glu Trp His Cys Gly Asn Gln Trp Ala Asn Ala Asn Leu Ile Gly
                485                 490                 495

Phe Glu Val Cys Glu Ser Tyr Pro Gly Arg Ile Ser Asp Lys Leu Phe
            500                 505                 510

Leu Glu Asn Glu Glu Ala Thr Leu Lys Val Ala Ala Asp Val Met Lys
        515                 520                 525

Ser Tyr Gly Leu Pro Val Asn Arg Asn Thr Val Arg Leu His Asn Glu
    530                 535                 540

Phe Phe Gly Thr Ser Cys Pro His Arg Ser Trp Asp Leu His Val Gly
545                 550                 555                 560
```

```
Lys Gly Glu Pro Tyr Thr Thr Thr Asn Ile Asn Lys Met Lys Asp Tyr
            565                 570                 575
Phe Ile Lys Arg Ile Lys His Tyr Tyr Asp Gly Lys Leu Glu Val
            580                 585                 590
Ser Lys Ala Ala Thr Ile Lys Gln Ser Asp Val Lys Gln Glu Val Lys
            595                 600                 605
Lys Gln Glu Ala Lys Gln Ile Val Lys Ala Thr Asp Trp Lys Gln Asn
            610                 615                 620
Lys Asp Gly Ile Trp Tyr Lys Ala Glu His Ala Ser Phe Thr Val Thr
625                 630                 635                 640
Ala Pro Glu Gly Ile Ile Thr Arg Tyr Lys Gly Pro Trp Thr Gly His
            645                 650                 655
Pro Gln Ala Gly Val Leu Gln Lys Gly Gln Thr Ile Lys Tyr Asp Glu
            660                 665                 670
Val Gln Lys Phe Asp Gly His Val Trp Val Ser Trp Glu Thr Phe Glu
            675                 680                 685
Gly Glu Thr Val Tyr Met Pro Val Arg Thr Trp Asp Ala Lys Thr Gly
            690                 695                 700
Lys Val Gly Lys Leu Trp Gly Glu Ile Lys
705                 710

<210> SEQ ID NO 81
<211> LENGTH: 1959
<212> TYPE: DNA
<213> ORGANISM: artificial
<220> FEATURE:
<223> OTHER INFORMATION: artificial construct

<400> SEQUENCE: 81
atgagaggat cgcatcacca tcaccatcac ggatccatga aaaccctgaa acaagcagag    60
tcctacatta agagtaaagt aaatacagga actgattttg atggtttata tgggtatcag   120
tgtatggact tagcagtaga ttatatttac catgtaacag atggtaaaat aagaatgtgg   180
ggtaatgcta aggatgcgat aaataactct tttggtggta ctgctacggt atataaaaac   240
taccctgctt ttagacctaa gtacggtgat gtagtcgtat ggactactgg taattttgca   300
acttatggtc atatcgcaat agttactaac cctgacccct tatggagacct tcaatatgtt   360 acagttcttg aacaaaactg gaacggtaac gggatttata aaaccgagtt agctacaatc   420
agaacacacg attacacagg aattacacat tttattaaag acgcaaagaa agatgaaaaa   480
tcacaagtat gtagtggttt ggctatggaa aaatatgaca ttacaaattt aaatgctaaa   540
caagataaat caagaatgg gagcgtgaaa gagttgaaac atatctattc aaaccatatt   600
aaaggtaaca gattacagc accaaaacct agtattcaag gtgtggtcat ccacaatgat   660
tatggtagta tgacacctag tcaatactta ccatggttat atgcacgtga ataacggt    720 acacacgtta acgttgggc tagtgtttat gcaaatagaa acgaagtgct ttggtatcat   780
ccgacagact acgtagagtg gcattgtggt aatcaatggg caaatgctaa cttaatcgga   840
tttgaagtgt gtgagtcgta tcctggtaga atctcggaca aattattctt agaaaatgaa   900
gaagcgacat tgaaagtagc tgcggatgtg atgagtcgt acggattacc agttaatcgc   960
aacactgtac gtctgcataa cgaattcttc ggaacttctt gtccacatcg ttcgtgggac  1020
ttgcatgttg gcaaaggtga gccttacaca actactaata ttaataaaat gaaagactac  1080
ttcatcaaac gcatcaaaca ttattatgac ggtggaaagc tagaagtaag caaagcagca  1140
```

```
actatcaaac aatctgacgt taagcaagaa gttaaaaagc aagaagcaaa acaaattgtg    1200
aaagcaacag atgctgcaac acatgaacat tcagcacaat ggttgaataa ttacaaaaaa    1260
ggatatggtt acggtcctta tccattaggt ataaatggcg gtatgcacta cggagttgat    1320
ttttttatga atattggaac accagtaaaa gctatttcaa gcggaaaaat agttgaagct    1380
ggttggagta attacggagg aggtaatcaa ataggtctta ttgaaaatga tggagtgcat    1440
agacaatggt atatgcatct aagtaaatat aatgttaaag taggagatta tgtcaaagct    1500
ggtcaaataa tcggttggtc tggaagcact ggttattcta cagcaccaca tttacacttc    1560
caaagaatgg ttaattcatt ttcaaattca actgcccaag atccaatgcc tttcttaaag    1620
agcgcaggat atggaaaagc aggtggtaca gtaactccaa cgccgaatac aggttggaaa    1680
cagaataaag atggcatttg gtataaagct gaacatgctt cgttcacagt gacagcacca    1740
gagggaatta tcacaagata caaaggtcct tggactggtc acccacaagc tggtgtatta    1800
caaaaaggtc aaacgattaa atatgatgag gttcaaaaat ttgacggtca tgtttgggta    1860
tcgtgggaaa cgtttgaggg cgaaactgta tacatgccgg tacgcacatg ggacgctaaa    1920
actggtaaag ttggtaagtt gtggggcgaa attaaataa                          1959
```

<210> SEQ ID NO 82
<211> LENGTH: 652
<212> TYPE: PRT
<213> ORGANISM: artificial
<220> FEATURE:
<223> OTHER INFORMATION: artificial construct

<400> SEQUENCE: 82

```
Met Arg Gly Ser His His His His His Gly Ser Met Lys Thr Leu
1               5                   10                  15

Lys Gln Ala Glu Ser Tyr Ile Lys Ser Lys Val Asn Thr Gly Thr Asp
            20                  25                  30

Phe Asp Gly Leu Tyr Gly Tyr Gln Cys Met Asp Leu Ala Val Asp Tyr
        35                  40                  45

Ile Tyr His Val Thr Asp Gly Lys Ile Arg Met Trp Gly Asn Ala Lys
    50                  55                  60

Asp Ala Ile Asn Asn Ser Phe Gly Gly Thr Ala Thr Val Tyr Lys Asn
65                  70                  75                  80

Tyr Pro Ala Phe Arg Pro Lys Tyr Gly Asp Val Val Trp Thr Thr
                85                  90                  95

Gly Asn Phe Ala Thr Tyr Gly His Ile Ala Ile Val Thr Asn Pro Asp
            100                 105                 110

Pro Tyr Gly Asp Leu Gln Tyr Val Thr Val Leu Glu Gln Asn Trp Asn
        115                 120                 125

Gly Asn Gly Ile Tyr Lys Thr Glu Leu Ala Thr Ile Arg Thr His Asp
    130                 135                 140

Tyr Thr Gly Ile Thr His Phe Ile Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220
```

```
Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Glu Ala Thr Leu
    290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Ala Thr Ile Lys Gln
370                 375                 380

Ser Asp Val Lys Gln Glu Val Lys Lys Gln Glu Ala Lys Gln Ile Val
385                 390                 395                 400

Lys Ala Thr Asp Ala Ala Thr His Glu His Ser Ala Gln Trp Leu Asn
                405                 410                 415

Asn Tyr Lys Lys Gly Tyr Gly Tyr Gly Pro Tyr Pro Leu Gly Ile Asn
            420                 425                 430

Gly Gly Met His Tyr Gly Val Asp Phe Phe Met Asn Ile Gly Thr Pro
        435                 440                 445

Val Lys Ala Ile Ser Ser Gly Lys Ile Val Glu Ala Gly Trp Ser Asn
    450                 455                 460

Tyr Gly Gly Gly Asn Gln Ile Gly Leu Ile Glu Asn Asp Gly Val His
465                 470                 475                 480

Arg Gln Trp Tyr Met His Leu Ser Lys Tyr Asn Val Lys Val Gly Asp
                485                 490                 495

Tyr Val Lys Ala Gly Gln Ile Ile Gly Trp Ser Gly Ser Thr Gly Tyr
            500                 505                 510

Ser Thr Ala Pro His Leu His Phe Gln Arg Met Val Asn Ser Phe Ser
        515                 520                 525

Asn Ser Thr Ala Gln Asp Pro Met Pro Phe Leu Lys Ser Ala Gly Tyr
    530                 535                 540

Gly Lys Ala Gly Gly Thr Val Thr Pro Thr Pro Asn Thr Gly Trp Lys
545                 550                 555                 560

Gln Asn Lys Asp Gly Ile Trp Tyr Lys Ala Glu His Ala Ser Phe Thr
                565                 570                 575

Val Thr Ala Pro Glu Gly Ile Ile Thr Arg Tyr Lys Gly Pro Trp Thr
            580                 585                 590

Gly His Pro Gln Ala Gly Val Leu Gln Lys Gly Gln Thr Ile Lys Tyr
        595                 600                 605

Asp Glu Val Gln Lys Phe Asp Gly His Val Trp Val Ser Trp Glu Thr
    610                 615                 620

Phe Glu Gly Glu Thr Val Tyr Met Pro Val Arg Thr Trp Asp Ala Lys
625                 630                 635                 640
```

Thr Gly Lys Val Gly Lys Leu Trp Gly Glu Ile Lys
            645                 650

<210> SEQ ID NO 83
<211> LENGTH: 1554
<212> TYPE: DNA
<213> ORGANISM: artificial
<220> FEATURE:
<223> OTHER INFORMATION: artificial construct

<400> SEQUENCE: 83

| | | |
|---|---|---|
| atgagaggat cgcatcacca tcaccatcac ggatccgctg caacacatga acattcagca | 60 |
| caatggttga ataattacaa aaaggatatg gttacggtc cttatccatt aggtataaat | 120 |
| ggcggtatgc actacggagt tgattttttt atgaatattg aacaccagt aaaagctatt | 180 |
| tcaagcggaa aaatagttga agctggttgg agtaattacg gaggaggtaa tcaaataggt | 240 |
| cttattgaaa tgatggagt gcatagacaa tggtatatgc atctaagtaa atataatgtt | 300 |
| aaagtaggag attatgtcaa agctggtcaa ataatcggtt ggtctggaag cactggttat | 360 |
| tctacagcac cacatttaca cttccaaaga atggttaatt cattttcaaa ttcaactgcc | 420 |
| caagatccaa tgcctttctt aaagagcgca ggatatggaa aagcaggtgg tacagtaact | 480 |
| ccaacgccga atacaggtga gctcttacgc cctaaagacg caagaaaga tgaaaaatca | 540 |
| caagtatgta gtggtttggc tatggaaaaa tatgacatta caaatttaaa tgctaaacaa | 600 |
| gataaatcaa agaatgggag cgtgaaagag ttgaaacata tctattcaaa ccatattaaa | 660 |
| ggtaacaaga ttacagcacc aaaacctagt attcaaggtg tggtcatcca caatgattat | 720 |
| ggtagtatga cacctagtca atacttacca tggttatatg cacgtgagaa taacggtaca | 780 |
| cacgttaacg gttgggctag tgtttatgca aatagaaacg aagtgctttg gtatcatccg | 840 |
| acagactacg tagagtggca ttgtggtaat caatgggcaa atgctaactt aatcggatt | 900 |
| gaagtgtgtg agtcgtatcc tggtagaatc tcggacaaat tattcttaga aaatgaagaa | 960 |
| gcgacattga agtagctgc ggatgtgatg aagtcgtacg gattaccagt taatcgcaac | 1020 |
| actgtacgtc tgcataacga attcttcgga acttcttgtc cacatcgttc gtgggacttg | 1080 |
| catgttggca aaggtgagcc ttacacaact actaatatta taaaatgaa agactacttc | 1140 |
| atcaaacgca tcaaacatta ttatgacggt ggaaagctag aagtaagcaa agcagcaact | 1200 |
| atcaaacaat ctgacgttaa gcaagaagtt aaaaagcaag aagcaaaaca aattgtgaaa | 1260 |
| gcaacagatt ggaaacagaa taaagatggc atttggtata agctgaaca tgcttcgttc | 1320 |
| acagtgacag caccagaggg aattatcaca agatacaaag gtccttggac tggtcaccca | 1380 |
| caagctggtg tattacaaaa aggtcaaacg attaaatatg atgaggttca aaaatttgac | 1440 |
| ggtcatgttt gggtatcgtg ggaaacgttt gagggcgaaa ctgtatacat gccggtacgc | 1500 |
| acatgggacg ctaaaactgg taaagttggt aagttgtggg gcgaaattaa ataa | 1554 |

<210> SEQ ID NO 84
<211> LENGTH: 517
<212> TYPE: PRT
<213> ORGANISM: artificial
<220> FEATURE:
<223> OTHER INFORMATION: artificial construct

<400> SEQUENCE: 84

Met Arg Gly Ser His His His His His His Gly Ser Ala Ala Thr His
1               5                   10                  15

Glu His Ser Ala Gln Trp Leu Asn Asn Tyr Lys Lys Gly Tyr Gly Tyr

-continued

```
                20                  25                  30
Gly Pro Tyr Pro Leu Gly Ile Asn Gly Gly Met His Tyr Gly Val Asp
            35                  40                  45
Phe Phe Met Asn Ile Gly Thr Pro Val Lys Ala Ile Ser Ser Gly Lys
        50                  55                  60
Ile Val Glu Ala Gly Trp Ser Asn Tyr Gly Gly Asn Gln Ile Gly
 65                  70                  75                  80
Leu Ile Glu Asn Asp Gly Val His Arg Gln Trp Tyr Met His Leu Ser
                85                  90                  95
Lys Tyr Asn Val Lys Val Gly Asp Tyr Val Lys Ala Gly Gln Ile Ile
            100                 105                 110
Gly Trp Ser Gly Ser Thr Gly Tyr Ser Thr Ala Pro His Leu His Phe
        115                 120                 125
Gln Arg Met Val Asn Ser Phe Ser Asn Ser Thr Ala Gln Asp Pro Met
    130                 135                 140
Pro Phe Leu Lys Ser Ala Gly Tyr Gly Lys Ala Gly Gly Thr Val Thr
145                 150                 155                 160
Pro Thr Pro Asn Thr Gly Glu Leu Leu Arg Pro Lys Asp Ala Lys Lys
                165                 170                 175
Asp Glu Lys Ser Gln Val Cys Ser Gly Leu Ala Met Glu Lys Tyr Asp
            180                 185                 190
Ile Thr Asn Leu Asn Ala Lys Gln Asp Lys Ser Lys Asn Gly Ser Val
        195                 200                 205
Lys Glu Leu Lys His Ile Tyr Ser Asn His Ile Lys Gly Asn Lys Ile
    210                 215                 220
Thr Ala Pro Lys Pro Ser Ile Gln Gly Val Val Ile His Asn Asp Tyr
225                 230                 235                 240
Gly Ser Met Thr Pro Ser Gln Tyr Leu Pro Trp Leu Tyr Ala Arg Glu
                245                 250                 255
Asn Asn Gly Thr His Val Asn Gly Trp Ala Ser Val Tyr Ala Asn Arg
            260                 265                 270
Asn Glu Val Leu Trp Tyr His Pro Thr Asp Tyr Val Glu Trp His Cys
        275                 280                 285
Gly Asn Gln Trp Ala Asn Ala Asn Leu Ile Gly Phe Glu Val Cys Glu
    290                 295                 300
Ser Tyr Pro Gly Arg Ile Ser Asp Lys Leu Phe Leu Glu Asn Glu Glu
305                 310                 315                 320
Ala Thr Leu Lys Val Ala Ala Asp Val Met Lys Ser Tyr Gly Leu Pro
                325                 330                 335
Val Asn Arg Asn Thr Val Arg Leu His Asn Glu Phe Phe Gly Thr Ser
            340                 345                 350
Cys Pro His Arg Ser Trp Asp Leu His Val Gly Lys Gly Glu Pro Tyr
        355                 360                 365
Thr Thr Thr Asn Ile Asn Lys Met Lys Asp Tyr Phe Ile Lys Arg Ile
    370                 375                 380
Lys His Tyr Tyr Asp Gly Gly Lys Leu Glu Val Ser Lys Ala Ala Thr
385                 390                 395                 400
Ile Lys Gln Ser Asp Val Lys Gln Glu Val Lys Gln Glu Ala Lys
                405                 410                 415
Gln Ile Val Lys Ala Thr Asp Trp Lys Gln Asn Lys Asp Gly Ile Trp
            420                 425                 430
Tyr Lys Ala Glu His Ala Ser Phe Thr Val Thr Ala Pro Glu Gly Ile
        435                 440                 445
```

```
Ile Thr Arg Tyr Lys Gly Pro Trp Thr Gly His Pro Gln Ala Gly Val
    450                 455                 460

Leu Gln Lys Gly Gln Thr Ile Lys Tyr Asp Glu Val Gln Lys Phe Asp
465                 470                 475                 480

Gly His Val Trp Val Ser Trp Glu Thr Phe Glu Gly Glu Thr Val Tyr
                485                 490                 495

Met Pro Val Arg Thr Trp Asp Ala Lys Thr Gly Lys Val Gly Lys Leu
            500                 505                 510

Trp Gly Glu Ile Lys
        515

<210> SEQ ID NO 85
<211> LENGTH: 1887
<212> TYPE: DNA
<213> ORGANISM: artificial
<220> FEATURE:
<223> OTHER INFORMATION: artificial construct

<400> SEQUENCE: 85
atgagaggat cgcatcacca tcaccatcac ggatccatgc taactgctat tgactatctt      60
acgaaaaaag gttggaaaat atcatctgac cctcgcactt acgatggtta ccctaaaaac     120
tacggctaca gaaattacca tgaaaacggc attaattatg atgagttttg tggtggttat     180
catagagctt ttgatgttta cagtaacgaa actaacgacg tgcctgctgt tactagcgga     240
acagttattg aagcaaacga ttacggtaat tttggtggta cattcgttat tagagacgct     300
aacgataacg attggatata tgggcatcta caacgtggct caatgcgatt tgttgtaggc     360
gacaaagtca atcaaggtga cattattggt ttacaaggta atagcaacta ttacgacaat     420
cctatgagtg tacatttaca tttacaatta cgccctaaag acgcaaagaa agatgaaaaa     480
tcacaagtat gtagtggttt ggctatggaa aaatatgaca ttacaaattt aaatgctaaa     540
caagataaat caaagaatgg gagcgtgaaa gagttgaaac atatctattc aaaccatatt     600
aaaggtaaca agattacagc accaaaacct agtattcaag gtgtggtcat ccacaatgat     660
tatggtagta tgacacctag tcaatactta ccatggttat atgcacgtga ataacggt      720 acacacgtta acggttgggc tagtgtttat gcaaatagaa acgaagtgct ttggtatcat     780
ccgacagact acgtagagtg gcattgtggt aatcaatggg caaatgctaa cttaatcgga     840
tttgaagtgt gtgagtcgta tcctggtaga atctcggaca aattattctt agaaaatgaa     900
gaagcgacat tgaaagtagc tgcggatgtg atgaagtcgt acggattacc agttaatcgc     960
aacactgtac gtctgcataa cgaattcttc ggaacttctt gtccacatcg ttcgtgggac    1020
ttgcatgttg gcaaaggtga gccttacaca actactaata ttaataaaat gaaagactac    1080
ttcatcaaac gcatcaaaca ttattatgac ggtggaaagc tagaagtaag caaagcagca    1140
actatcaaac aatctgacgt taagcaagaa gttaaaaagc aagaagcaaa acaaattgtg    1200
aaagcaacag attggaaaca gaataaagat ggcatttggt ataaagctga acatgcttcg    1260
ttcacagtga cagcaccaga gggaattatc acaagataca aggtccttg gactggtcac    1320 ccacaagctg gtgtattaca aaaaggtcaa acgattaaat atgatgaggt tcaaaaattt    1380
gacggtcatg tttgggtatc gtgggaaacg tttgagggcg aaactgtata catgccggta    1440
cgcacatggg acgctaaaac tggtaaagtt ggtaagttgt ggggcgaaat taagagctc    1500 ggtggaaagc tagaagtaag caaagcagca actatcaaac aatctgacgt taagcaagaa    1560
gttaaaaagc aagaagcaaa acaaattgtg aaagcaacag attggaaaca gaataaagat    1620
```

```
ggcatttggt ataaagctga acatgcttcg ttcacagtga cagcaccaga gggaattatc   1680
acaagataca aaggtccttg gactggtcac ccacaagctg gtgtattaca aaaaggtcaa   1740
acgattaaat atgatgaggt tcaaaaattt gacggtcatg tttgggtatc gtgggaaacg   1800
tttgagggcg aaactgtata catgccggta cgcacatggg acgctaaaac tggtaaagtt   1860
ggtaagttgt ggggcgaaat taaataa                                       1887
```

<210> SEQ ID NO 86
<211> LENGTH: 628
<212> TYPE: PRT
<213> ORGANISM: artificial
<220> FEATURE:
<223> OTHER INFORMATION: artificial construct

<400> SEQUENCE: 86

```
Met Arg Gly Ser His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
        35                  40                  45

Asn Gly Ile Asn Tyr Asp Glu Phe Cys Gly Gly Tyr His Arg Ala Phe
    50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Gly Thr Phe Val
                85                  90                  95

Ile Arg Asp Ala Asn Asp Asn Asp Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Glu Ala Thr Leu
    290                 295                 300

Lys Val Ala Ala Asp Val Met Lys Ser Tyr Gly Leu Pro Val Asn Arg
```

```
            305                 310                 315                 320
        Asn Thr Val Arg Leu His Asn Glu Phe Phe Gly Thr Ser Cys Pro His
                        325                 330                 335

Arg Ser Trp Asp Leu His Val Gly Lys Gly Glu Pro Tyr Thr Thr Thr
                        340                 345                 350

Asn Ile Asn Lys Met Lys Asp Tyr Phe Ile Lys Arg Ile Lys His Tyr
                        355                 360                 365

Tyr Asp Gly Gly Lys Leu Glu Val Ser Lys Ala Ala Thr Ile Lys Gln
                370                 375                 380

Ser Asp Val Lys Gln Glu Val Lys Lys Gln Glu Ala Lys Gln Ile Val
        385                 390                 395                 400

Lys Ala Thr Asp Trp Lys Gln Asn Lys Asp Gly Ile Trp Tyr Lys Ala
                        405                 410                 415

Glu His Ala Ser Phe Thr Val Thr Ala Pro Glu Gly Ile Ile Thr Arg
                        420                 425                 430

Tyr Lys Gly Pro Trp Thr Gly His Pro Gln Ala Gly Val Leu Gln Lys
                        435                 440                 445

Gly Gln Thr Ile Lys Tyr Asp Glu Val Gln Lys Phe Asp Gly His Val
                450                 455                 460

Trp Val Ser Trp Glu Thr Phe Glu Gly Glu Thr Val Tyr Met Pro Val
        465                 470                 475                 480

Arg Thr Trp Asp Ala Lys Thr Gly Lys Val Gly Lys Leu Trp Gly Glu
                        485                 490                 495

Ile Lys Glu Leu Gly Gly Lys Leu Glu Val Ser Lys Ala Ala Thr Ile
                        500                 505                 510

Lys Gln Ser Asp Val Lys Gln Glu Val Lys Lys Gln Glu Ala Lys Gln
                        515                 520                 525

Ile Val Lys Ala Thr Asp Trp Lys Gln Asn Lys Asp Gly Ile Trp Tyr
                530                 535                 540

Lys Ala Glu His Ala Ser Phe Thr Val Thr Ala Pro Glu Gly Ile Ile
        545                 550                 555                 560

Thr Arg Tyr Lys Gly Pro Trp Thr Gly His Pro Gln Ala Gly Val Leu
                        565                 570                 575

Gln Lys Gly Gln Thr Ile Lys Tyr Asp Glu Val Gln Lys Phe Asp Gly
                        580                 585                 590

His Val Trp Val Ser Trp Glu Thr Phe Glu Gly Glu Thr Val Tyr Met
                        595                 600                 605

Pro Val Arg Thr Trp Asp Ala Lys Thr Gly Lys Val Gly Lys Leu Trp
                610                 615                 620

Gly Glu Ile Lys
        625

<210> SEQ ID NO 87
<211> LENGTH: 1035
<212> TYPE: DNA
<213> ORGANISM: artificial
<220> FEATURE:
<223> OTHER INFORMATION: artificial construct

<400> SEQUENCE: 87
atgagaggat cgcatcacca tcaccatcac ggatccatgc taactgctat tgactatctt        60
acgaaaaaag gttggaaaat atcatctgac cctcgcactt acgatggtta ccctaaaaac      120
tacggctaca gaaattacca tgaaaacggc attaattatg atgagttttg tggtggttat      180
catagagctt ttgatgttta cagtaacgaa actaacgacg tgcctgctgt tactagcgga      240
```

```
acagttattg aagcaaacga ttacggtaat tttggtggta cattcgttat tagagacgct    300
aacgataacg attggatata tgggcatcta caacgtggct caatgcgatt tgttgtaggc    360
gacaaagtca atcaaggtga cattattggt ttacaaggta atagcaacta ttacgacaat    420
cctatgagtg tacatttaca tttacaatta cgccctaaag acgcaaagaa agatgaaaaa    480
tcacaagtat gtagtggttt ggctatggaa aaatatgaca ttacaaattt aaatgctaaa    540
caagataaat caaagaatgg gagcgtgaaa gagttgaaac atatctattc aaaccatatt    600
aaaggtaaca agattacagc accaaaacct agtattcaag gtgagctcgg tggaaagcta    660
gaagtaagca aagcagcaac tatcaaacaa tctgacgtta agcaagaagt taaaaagcaa    720
gaagcaaaac aaattgtgaa agcaacagat tggaaacaga ataaagatgg catttggtat    780
aaagctgaac atgcttcgtt cacagtgaca gcaccagagg gaattatcac aagatacaaa    840
ggtccttgga ctggtcaccc acaagctggt gtattacaaa aaggtcaaac gattaaatat    900
gatgaggttc aaaaatttga cggtcatgtt tgggtatcgt gggaaacgtt tgagggcgaa    960
actgtataca tgccggtacg cacatgggac gctaaaactg gtaaagttgg taagttgtgg   1020
ggcgaaatta aataa                                                    1035
```

<210> SEQ ID NO 88
<211> LENGTH: 344
<212> TYPE: PRT
<213> ORGANISM: artificial
<220> FEATURE:
<223> OTHER INFORMATION: artificial construct

<400> SEQUENCE: 88

```
Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
        35                  40                  45

Asn Gly Ile Asn Tyr Asp Glu Phe Cys Gly Gly Tyr His Arg Ala Phe
    50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Thr Phe Val
                85                  90                  95

Ile Arg Asp Ala Asn Asp Asn Asp Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Glu Leu Gly Gly Lys Leu Glu Val Ser Lys
```

```
                    210                 215                 220
Ala Ala Thr Ile Lys Gln Ser Asp Val Lys Gln Glu Val Lys Gln
225                 230                 235                 240

Glu Ala Lys Gln Ile Val Lys Ala Thr Asp Trp Lys Gln Asn Lys Asp
                245                 250                 255

Gly Ile Trp Tyr Lys Ala Glu His Ala Ser Phe Thr Val Thr Ala Pro
            260                 265                 270

Glu Gly Ile Ile Thr Arg Tyr Lys Gly Pro Trp Thr Gly His Pro Gln
        275                 280                 285

Ala Gly Val Leu Gln Lys Gly Gln Thr Ile Lys Tyr Asp Glu Val Gln
    290                 295                 300

Lys Phe Asp Gly His Val Trp Val Ser Trp Glu Thr Phe Glu Gly Glu
305                 310                 315                 320

Thr Val Tyr Met Pro Val Arg Thr Trp Asp Ala Lys Thr Gly Lys Val
                325                 330                 335

Gly Lys Leu Trp Gly Glu Ile Lys
            340
```

<210> SEQ ID NO 89
<211> LENGTH: 2961
<212> TYPE: DNA
<213> ORGANISM: artificial
<220> FEATURE:
<223> OTHER INFORMATION: artificial construct

<400> SEQUENCE: 89

| | | | | | |
|---|---|---|---|---|---|
| atgagaggat | cgcatcacca | tcaccatcac | ggatccatgc | taactgctat | tgactatctt | 60 |
| acgaaaaaag | gttggaaaat | atcatctgac | cctcgcactt | acgatggtta | ccctaaaaac | 120 |
| tacggctaca | gaaattacca | tgaaaacggc | attaattatg | atgagttttg | tggtggttat | 180 |
| catagagctt | ttgatgttta | cagtaacgaa | actaacgacg | tgcctgctgt | tactagcgga | 240 |
| acagttattg | aagcaaacga | ttacggtaat | tttggtggta | cattcgttat | tagagacgct | 300 |
| aacgataacg | attggatata | tgggcatcta | caacgtggct | caatgcgatt | tgttgtaggc | 360 |
| gacaaagtca | tcaaggtgac | cattattggt | ttacaaggta | tagcaactaa | ttacgacaat | 420 |
| cctatgagtg | tacatttaca | tttacaatta | cgccctaaag | acgcaaagaa | agatgaaaaa | 480 |
| tcacaagtat | gtagtggttt | ggctatggaa | aaatatgaca | ttacaaattt | aaatgctaaa | 540 |
| caagataaat | caagaatgg | gagcgtgaaa | gagttgaaac | atatctattc | aaaccatatt | 600 |
| aaaggtaaca | agattacagc | accaaaacct | agtattcaag | gtgtggtcat | ccacaatgat | 660 |
| tatggtagta | tgacacctag | tcaatactta | ccatggttat | atgcacgtga | gaataacggt | 720 |
| acacacgtta | acgttgggc | tagtgtttat | gcaaatagaa | acgaagtgct | ttggtatcat | 780 |
| ccgacagact | acgtagagtg | gcattgtggt | aatcaatggg | caaatgctaa | cttaatcgga | 840 |
| tttgaagtgt | gtgagtcgta | tcctggtaga | atctcggaca | aattattctt | agaaaatgaa | 900 |
| gaagcgacat | tgaaagtagc | tgcggatgtg | atgagtcgt | acggattacc | agttaatcgc | 960 |
| aacactgtac | gtctgcataa | cgaattcttc | ggaacttctt | gtccacatcg | ttcgtgggac | 1020 |
| ttgcatgttg | gcaaaggtga | gccttacaca | actactaata | ttaataaaat | gaaagactac | 1080 |
| ttcatcaaac | gcatcaaaca | ttattatgac | ggtggaaagc | tagaagtaag | caaagcagca | 1140 |
| actatcaaac | aatctgacgt | taagcaagaa | gttaaaaagc | aagaagcaaa | acaaattgtg | 1200 |
| aaagcaacag | attggaaaca | gaataaagat | ggcatttgg | ataaagctga | acatgcttcg | 1260 |
| ttcacagtga | cagcaccaga | gggaattatc | acaagataca | aaggtccttg | gactggtcac | 1320 |

```
ccacaagctg gtgtattaca aaaaggtcaa acgattaaat atgatgaggt tcaaaaattt    1380
gacggtcatg tttgggtatc gtgggaaacg tttgagggcg aaactgtata catgccggta    1440
cgcacatggg acgctaaaac tggtaaagtt ggtaagttgt ggggcgaaat taaagagctc    1500
atgctaactc tctattgacta tcttacgaaa aaaggttgga aaatatcatc tgaccctcgc    1560
acttacgatg gttaccctaa aaactacggc tacagaaatt accatgaaaa cggcattaat    1620
tatgatgagt tttgtggtgg ttatcataga gcttttgatg tttacagtaa cgaaactaac    1680
gacgtgcctg ctgttactag cggaacagtt attgaagcaa acgattacgg taattttggt    1740
ggtacattcg ttattagaga cgctaacgat aacgattgga tatatgggca tctacaacgt    1800
ggctcaatgc gatttgttgt aggcgacaaa gtcaatcaag gtgacattat tggtttacaa    1860
ggtaatagca actattacga caatcctatg agtgtacatt tacatttaca attacgccct    1920
aaagacgcaa agaaagatga aaaatcacaa gtatgtagtg gtttggctat ggaaaaatat    1980
gacattacaa atttaaatgc taaacaagat aaatcaaaga atgggagcgt gaaagagttg    2040
aaacatatct attcaaacca tattaaaggt aacaagatta cagcaccaaa acctagtatt    2100
caaggtgtgg tcatccacaa tgattatggt agtatgacac ctagtcaata cttaccatgg    2160
ttatatgcac gtgagaataa cggtacacac gttaacggtt gggctagtgt ttatgcaaat    2220
agaaacgaag tgctttggta tcatccgaca gactacgtag agtggcattg tggtaatcaa    2280
tgggcaaatg ctaacttaat cggatttgaa gtgtgtgagt cgtatcctgg tagaatctcg    2340
gacaaattat tcttagaaaa tgaagaagcg acattgaaag tagctgcgga tgtgatgaag    2400
tcgtacggat taccagttaa tcgcaacact gtacgtctgc ataacgaatt cttcggaact    2460
tcttgtccac atcgttcgtg ggacttgcat gttggcaaag gtgagcctta cacaactact    2520
aatattaata aaatgaaaga ctacttcatc aaacgcatca acattatta tgacggtgga    2580
aagctagaag taagcaaagc agcaactatc aaacaatctg acgttaagca agaagttaaa    2640
aagcaagaag caaacaaat tgtgaaagca acagattgga acagaataa agatggcatt    2700
tggtataaag ctgaacatgc ttcgttcaca gtgacagcac cagagggaat tatcacaaga    2760
tacaaaggtc cttggactgg tcacccacaa gctggtgtat tacaaaaagg tcaaacgatt    2820
aaatatgatg aggttcaaaa atttgacggt catgtttggg tatcgtggga aacgtttgag    2880
ggcgaaactg tatacatgcc ggtacgcaca tgggacgcta aaactggtaa agttggtaag    2940
ttgtggggcg aaattaaata a                                              2961
```

<210> SEQ ID NO 90
<211> LENGTH: 986
<212> TYPE: PRT
<213> ORGANISM: artificial
<220> FEATURE:
<223> OTHER INFORMATION: artificial construct

<400> SEQUENCE: 90

```
Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
        35                  40                  45

Asn Gly Ile Asn Tyr Asp Glu Phe Cys Gly Gly Tyr His Arg Ala Phe
    50                  55                  60
```

```
Asp Val Tyr Ser Asn Glu Thr Asn Asp Val Pro Ala Val Thr Ser Gly
 65                  70                  75                  80

Thr Val Ile Glu Ala Asn Asp Tyr Gly Asn Phe Gly Gly Thr Phe Val
                 85                  90                  95

Ile Arg Asp Ala Asn Asp Asn Asp Trp Ile Tyr Gly His Leu Gln Arg
                100                 105                 110

Gly Ser Met Arg Phe Val Val Gly Asp Lys Val Asn Gln Gly Asp Ile
            115                 120                 125

Ile Gly Leu Gln Gly Asn Ser Asn Tyr Tyr Asp Asn Pro Met Ser Val
            130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
                180                 185                 190

Lys His Ile Tyr Ser Asn His Ile Lys Gly Asn Lys Ile Thr Ala Pro
            195                 200                 205

Lys Pro Ser Ile Gln Gly Val Val Ile His Asn Asp Tyr Gly Ser Met
210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
            275                 280                 285

Gly Arg Ile Ser Asp Lys Leu Phe Leu Glu Asn Glu Glu Ala Thr Leu
            290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
            355                 360                 365

Tyr Asp Gly Gly Lys Leu Glu Val Ser Lys Ala Ala Thr Ile Lys Gln
370                 375                 380

Ser Asp Val Lys Gln Glu Val Lys Gln Glu Ala Lys Gln Ile Val
385                 390                 395                 400

Lys Ala Thr Asp Trp Lys Gln Asn Lys Asp Gly Ile Trp Lys Ala
            405                 410                 415

Glu His Ala Ser Phe Thr Val Thr Ala Pro Glu Gly Ile Ile Thr Arg
                420                 425                 430

Tyr Lys Gly Pro Trp Thr Gly His Pro Gln Ala Gly Val Leu Gln Lys
            435                 440                 445

Gly Gln Thr Ile Lys Tyr Asp Glu Val Gln Lys Phe Asp Gly His Val
            450                 455                 460

Trp Val Ser Trp Glu Thr Phe Glu Gly Glu Thr Val Tyr Met Pro Val
465                 470                 475                 480

Arg Thr Trp Asp Ala Lys Thr Gly Lys Val Gly Lys Leu Trp Gly Glu
```

-continued

```
                485                 490                 495
Ile Lys Glu Leu Met Leu Thr Ala Ile Asp Tyr Leu Thr Lys Lys Gly
                500                 505                 510

Trp Lys Ile Ser Ser Asp Pro Arg Thr Tyr Asp Gly Tyr Pro Lys Asn
            515                 520                 525

Tyr Gly Tyr Arg Asn Tyr His Glu Asn Gly Ile Asn Tyr Asp Glu Phe
            530                 535                 540

Cys Gly Tyr His Arg Ala Phe Asp Val Tyr Ser Asn Glu Thr Asn
545                 550                 555                 560

Asp Val Pro Ala Val Thr Ser Gly Thr Val Ile Glu Ala Asn Asp Tyr
                565                 570                 575

Gly Asn Phe Gly Gly Thr Phe Val Ile Arg Asp Ala Asn Asp Asn Asp
            580                 585                 590

Trp Ile Tyr Gly His Leu Gln Arg Gly Ser Met Arg Phe Val Val Gly
            595                 600                 605

Asp Lys Val Asn Gln Gly Asp Ile Ile Gly Leu Gln Gly Asn Ser Asn
            610                 615                 620

Tyr Tyr Asp Asn Pro Met Ser Val His Leu His Leu Gln Leu Arg Pro
625                 630                 635                 640

Lys Asp Ala Lys Lys Asp Glu Lys Ser Gln Val Cys Ser Gly Leu Ala
                645                 650                 655

Met Glu Lys Tyr Asp Ile Thr Asn Leu Asn Ala Lys Gln Asp Lys Ser
                660                 665                 670

Lys Asn Gly Ser Val Lys Glu Leu Lys His Ile Tyr Ser Asn His Ile
            675                 680                 685

Lys Gly Asn Lys Ile Thr Ala Pro Lys Pro Ser Ile Gln Gly Val Val
            690                 695                 700

Ile His Asn Asp Tyr Gly Ser Met Thr Pro Ser Gln Tyr Leu Pro Trp
705                 710                 715                 720

Leu Tyr Ala Arg Glu Asn Asn Gly Thr His Val Asn Gly Trp Ala Ser
                725                 730                 735

Val Tyr Ala Asn Arg Asn Glu Val Leu Trp Tyr His Pro Thr Asp Tyr
            740                 745                 750

Val Glu Trp His Cys Gly Asn Gln Trp Ala Asn Ala Asn Leu Ile Gly
            755                 760                 765

Phe Glu Val Cys Glu Ser Tyr Pro Gly Arg Ile Ser Asp Lys Leu Phe
770                 775                 780

Leu Glu Asn Glu Glu Ala Thr Leu Lys Val Ala Ala Asp Val Met Lys
                785                 790                 795                 800

Ser Tyr Gly Leu Pro Val Asn Arg Asn Thr Val Arg Leu His Asn Glu
                805                 810                 815

Phe Phe Gly Thr Ser Cys Pro His Arg Ser Trp Asp Leu His Val Gly
            820                 825                 830

Lys Gly Glu Pro Tyr Thr Thr Thr Asn Ile Asn Lys Met Lys Asp Tyr
            835                 840                 845

Phe Ile Lys Arg Ile Lys His Tyr Tyr Asp Gly Gly Lys Leu Glu Val
850                 855                 860

Ser Lys Ala Ala Thr Ile Lys Gln Ser Asp Val Lys Gln Glu Val Lys
865                 870                 875                 880

Lys Gln Glu Ala Lys Gln Ile Val Lys Ala Thr Asp Trp Lys Gln Asn
                885                 890                 895

Lys Asp Gly Ile Trp Tyr Lys Ala Glu His Ala Ser Phe Thr Val Thr
            900                 905                 910
```

```
Ala Pro Glu Gly Ile Ile Thr Arg Tyr Lys Gly Pro Trp Thr Gly His
        915                 920                 925

Pro Gln Ala Gly Val Leu Gln Lys Gly Gln Thr Ile Lys Tyr Asp Glu
    930                 935                 940

Val Gln Lys Phe Asp Gly His Val Trp Val Ser Trp Glu Thr Phe Glu
945                 950                 955                 960

Gly Glu Thr Val Tyr Met Pro Val Arg Thr Trp Asp Ala Lys Thr Gly
                965                 970                 975

Lys Val Gly Lys Leu Trp Gly Glu Ile Lys
            980                 985

<210> SEQ ID NO 91
<211> LENGTH: 1953
<212> TYPE: DNA
<213> ORGANISM: artificial
<220> FEATURE:
<223> OTHER INFORMATION: artificial construct

<400> SEQUENCE: 91
atgagaggat cgcatcacca tcaccatcac ggatccatga aaaccctgaa acaagcagag      60
tcctacatta gagtaaagt aaatacagga actgattttg atggtttata tgggtatcag     120
tgtatggact tagcagtaga ttatatttac catgtaacag atggtaaaat aagaatgtgg     180
ggtaatgcta aggatgcgat aaataactct tttggtggta ctgctacggt atataaaaac     240
taccctgctt ttagacctaa gtacggtgat gtagtcgtat ggactactgg taattttgca     300
acttatggtc atatcgcaat agttactaac cctgacccct atggagacct tcaatatgtt     360
acagttcttg aacaaaactg gaacggtaac gggatttata aaccgagtt agctacaatc     420 agaacacacg attacacagg aattacacat tttattaaag acgcaaagaa agatgaaaaa     480
tcacaagtat gtagtggttt ggctatggaa aaatatgaca ttacaaattt aaatgctaaa     540
caagataaat caagaatgg gagcgtgaaa gagttgaaac atatctattc aaaccatatt     600
aaaggtaaca agattacagc accaaaacct agtattcaag gtgtggtcat ccacaatgat     660
tatggtagta tgacacctag tcaatactta ccatggttat atgcacgtga gaataacggt     720
acacacgtta acggttgggc tagtgtttat gcaaatagaa acgaagtgct ttggtatcat     780
ccgacagact acgtagagtg gcattgtggt aatcaatggg caaatgctaa cttaatcgga     840
tttgaagtgt gtgagtcgta tcctggtaga atctcggaca attattctt agaaaatgaa     900 gaagcgacat tgaaagtagc tgcggatgtg atgaagtcgt acggattacc agttaatcgc     960
aacactgtac gtctgcataa cgaattcttc ggaacttctt gtccacatcg ttcgtgggac    1020
ttgcatgttg gcaaaggtga gccttacaca actactaata ttaataaaat gaaagactac    1080
ttcatcaaac gcatcaaaca ttattatgac ggtggaaagc tagaagtaag caaagcagca    1140
actatcaaac aatctgacgt taagcaagaa gttaaaaagc aagaagcaaa acaaattgtg    1200
aaagcaacag atgctgcaac acatgaacat tcagcacaat ggttgaataa ttacaaaaaa    1260
ggatatggtt acggtcctta tccattaggt ataaatggcg gtatgcacta cggagttgat    1320
ttttttatga atattggaac accagtaaaa gctatttcaa gcggaaaaat agttgaagct    1380
ggttggagta attacggagg aggtaatcaa ataggtctta ttgaaaatga tggagtgcat    1440
agacaatggt atatgcatct aagtaaatat aatgttaaag taggagatta tgtcaaagct    1500
ggtcaaataa tcggttggtc tggaagcact ggttattcta cagcaccaca tttcacttc    1560 caaagaatgg ttaattcatt ttcaaattca actgcccaag atccaatgcc tttcttaaag    1620
```

-continued

```
agcgcaggat atggaaaagc aggtggtaca gtaactccaa cgccgaatac aggttggaaa    1680
acaaacaaat atggcacact atataaatca gagtcagcta gcttcacacc taatacagat    1740
ataataacaa gaacgactgg tccatttaga agcatgccgc agtcaggagt cttaaaagca    1800
ggtcaaacaa ttcattatga tgaagtgatg aaacaagacg tcatgtttg ggtaggttat     1860 acaggtaaca gtggccaacg tatttacttg cctgtaagaa catggaataa atctactaat    1920
actttaggtg ttctttgggg aactataaag taa                                 1953
```

<210> SEQ ID NO 92
<211> LENGTH: 650
<212> TYPE: PRT
<213> ORGANISM: artificial
<220> FEATURE:
<223> OTHER INFORMATION: artificial construct

<400> SEQUENCE: 92

```
Met Arg Gly Ser His His His His His His Gly Ser Met Lys Thr Leu
1               5                   10                  15

Lys Gln Ala Glu Ser Tyr Ile Lys Ser Lys Val Asn Thr Gly Thr Asp
            20                  25                  30

Phe Asp Gly Leu Tyr Gly Tyr Gln Cys Met Asp Leu Ala Val Asp Tyr
        35                  40                  45

Ile Tyr His Val Thr Asp Gly Lys Ile Arg Met Trp Gly Asn Ala Lys
50                  55                  60

Asp Ala Ile Asn Asn Ser Phe Gly Gly Thr Ala Thr Val Tyr Lys Asn
65                  70                  75                  80

Tyr Pro Ala Phe Arg Pro Lys Tyr Gly Asp Val Val Trp Thr Thr
                85                  90                  95

Gly Asn Phe Ala Thr Tyr Gly His Ile Ala Ile Val Thr Asn Pro Asp
            100                 105                 110

Pro Tyr Gly Asp Leu Gln Tyr Val Thr Val Leu Glu Gln Asn Trp Asn
        115                 120                 125

Gly Asn Gly Ile Tyr Lys Thr Glu Leu Ala Thr Ile Arg Thr His Asp
130                 135                 140

Tyr Thr Gly Ile Thr His Phe Ile Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
    210                 215                 220

Thr Pro Ser Gln Tyr Leu Pro Trp Leu Tyr Ala Arg Glu Asn Gly
225                 230                 235                 240

Thr His Val Asn Gly Trp Ala Ser Val Tyr Ala Asn Arg Asn Glu Val
            245                 250                 255

Leu Trp Tyr His Pro Thr Asp Tyr Val Glu Trp His Cys Gly Asn Gln
        260                 265                 270

Trp Ala Asn Ala Asn Leu Ile Gly Phe Glu Val Cys Glu Ser Tyr Pro
    275                 280                 285

Gly Arg Ile Ser Asp Lys Leu Phe Leu Glu Asn Glu Glu Ala Thr Leu
290                 295                 300
```

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
            325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
            355                 360                 365

Tyr Asp Gly Gly Lys Leu Glu Val Ser Lys Ala Ala Thr Ile Lys Gln
            370                 375                 380

Ser Asp Val Lys Gln Glu Val Lys Gln Glu Ala Lys Gln Ile Val
385                 390                 395                 400

Lys Ala Thr Asp Ala Ala Thr His Glu His Ser Ala Gln Trp Leu Asn
                405                 410                 415

Asn Tyr Lys Lys Gly Tyr Gly Tyr Pro Tyr Pro Leu Gly Ile Asn
            420                 425                 430

Gly Gly Met His Tyr Gly Val Asp Phe Phe Met Asn Ile Gly Thr Pro
                435                 440                 445

Val Lys Ala Ile Ser Ser Gly Lys Ile Val Glu Ala Gly Trp Ser Asn
450                 455                 460

Tyr Gly Gly Asn Gln Ile Gly Leu Ile Glu Asn Asp Gly Val His
465                 470                 475                 480

Arg Gln Trp Tyr Met His Leu Ser Lys Tyr Asn Val Lys Val Gly Asp
                485                 490                 495

Tyr Val Lys Ala Gly Gln Ile Ile Gly Trp Ser Gly Ser Thr Gly Tyr
            500                 505                 510

Ser Thr Ala Pro His Leu His Phe Gln Arg Met Val Asn Ser Phe Ser
            515                 520                 525

Asn Ser Thr Ala Gln Asp Pro Met Pro Phe Leu Lys Ser Ala Gly Tyr
            530                 535                 540

Gly Lys Ala Gly Gly Thr Val Thr Pro Thr Pro Asn Thr Gly Trp Lys
545                 550                 555                 560

Thr Asn Lys Tyr Gly Thr Leu Tyr Lys Ser Glu Ser Ala Ser Phe Thr
                565                 570                 575

Pro Asn Thr Asp Ile Ile Thr Arg Thr Thr Gly Pro Phe Arg Ser Met
            580                 585                 590

Pro Gln Ser Gly Val Leu Lys Ala Gly Gln Thr Ile His Tyr Asp Glu
            595                 600                 605

Val Met Lys Gln Asp Gly His Val Trp Val Gly Tyr Thr Gly Asn Ser
            610                 615                 620

Gly Gln Arg Ile Tyr Leu Pro Val Arg Thr Trp Asn Lys Ser Thr Asn
625                 630                 635                 640

Thr Leu Gly Val Leu Trp Gly Thr Ile Lys
                645                 650

<210> SEQ ID NO 93
<211> LENGTH: 1521
<212> TYPE: DNA
<213> ORGANISM: artificial
<220> FEATURE:
<223> OTHER INFORMATION: artificial construct

<400> SEQUENCE: 93
atgagaggat cgcatcacca tcaccatcac ggatccgctg caaacatgaa acattcagca    60

```
caatggttga ataattacaa aaaaggatat ggttacggtc cttatccatt aggtataaat     120
ggcggtatgc actacggagt tgattttttt atgaatattg aacaccagt aaaagctatt      180 tcaagcggaa aaatagttga agctggttgg agtaattacg gaggaggtaa tcaaataggt    240
cttattgaaa atgatggagt gcatagacaa tggtatatgc atctaagtaa atataatgtt   300
aaagtaggag attatgtcaa agctggtcaa ataatcggtt ggtctggaag cactggttat   360
tctacagcac cacatttaca cttccaaaga atggttaatt cattttcaaa ttcaactgcc   420
caagatccaa tgcctttctt aaagagcgca ggatatggaa aagcaggtgg tacagtaact   480
ccaacgccga atacaggttg gaaaacaaac aaatatggca cactatataa atcagagtca   540
gctagcttca cacctaatac agatataata acaagaacga ctggtccatt tagaagcatg   600
ccgcagtcag gagtcttaaa agcaggtcaa acaattcatt atgatgaagt gatgaaacaa   660
gacggtcatg tttgggtagg ttatacaggt aacagtggcc aacgtattta cttgcctgta   720
agaacatgga ataaatctac taatacttta ggtgttcttt ggggaactat aaaggagctc   780
gctgcaacac atgaacattc agcacaatgg ttgaataatt acaaaaaagg atatggttac   840
ggtccttatc cattaggtat aaatggcggt atgcactacg gagttgattt ttttatgaat   900
attggaacac cagtaaaagc tatttcaagc ggaaaaatag ttgaagctgg ttggagtaat   960
tacggaggag gtaatcaaat aggtcttatt gaaaatgatg gagtgcatag acaatggtat  1020
atgcatctaa gtaaatataa tgttaaagta ggagattatg tcaaagctgg tcaaataatc  1080
ggttggtctg gaagcactgg ttattctaca gcaccacatt tacacttcca agaatggtt   1140 aattcatttt caaattcaac tgcccaagat ccaatgcctt tcttaaagag cgcaggatat  1200
ggaaaagcag gtggtacagt aactccaacg ccgaatacag gttggaaaac aaacaaatat  1260
ggcacactat ataatcaga gtcagctagc ttcacaccta atacagatat aataacaaga   1320
acgactggtc catttagaag catgccgcag tcaggagtct taaaagcagg tcaaacaatt  1380
cattatgatg aagtgatgaa acaagacggt catgtttggg taggttatac aggtaacagt  1440
ggccaacgta tttacttgcc tgtaagaaca tggaataaat ctactaatac tttaggtgtt  1500
ctttggggaa ctataaagtg a                                            1521
```

<210> SEQ ID NO 94
<211> LENGTH: 506
<212> TYPE: PRT
<213> ORGANISM: artificial
<220> FEATURE:
<223> OTHER INFORMATION: artificial construct

<400> SEQUENCE: 94

Met Arg Gly Ser His His His His His His Gly Ser Ala Ala Thr His
1               5                   10                  15

Glu His Ser Ala Gln Trp Leu Asn Asn Tyr Lys Lys Gly Tyr Gly Tyr
            20                  25                  30

Gly Pro Tyr Pro Leu Gly Ile Asn Gly Met His Tyr Gly Val Asp
        35                  40                  45

Phe Phe Met Asn Ile Gly Thr Pro Val Lys Ala Ile Ser Ser Gly Lys
    50                  55                  60

Ile Val Glu Ala Gly Trp Ser Asn Tyr Gly Gly Asn Gln Ile Gly
65                  70                  75                  80

Leu Ile Glu Asn Asp Gly Val His Arg Gln Trp Tyr Met His Leu Ser
                85                  90                  95

Lys Tyr Asn Val Lys Val Gly Asp Tyr Val Lys Ala Gly Gln Ile Ile

-continued

```
                100                 105                 110
Gly Trp Ser Gly Ser Thr Gly Tyr Ser Thr Ala Pro His Leu His Phe
            115                 120                 125

Gln Arg Met Val Asn Ser Phe Ser Asn Ser Thr Ala Gln Asp Pro Met
        130                 135                 140

Pro Phe Leu Lys Ser Ala Gly Tyr Gly Lys Ala Gly Gly Thr Val Thr
145                 150                 155                 160

Pro Thr Pro Asn Thr Gly Trp Lys Thr Asn Lys Tyr Gly Thr Leu Tyr
                165                 170                 175

Lys Ser Glu Ser Ala Ser Phe Thr Pro Asn Thr Asp Ile Ile Thr Arg
            180                 185                 190

Thr Thr Gly Pro Phe Arg Ser Met Pro Gln Ser Gly Val Leu Lys Ala
        195                 200                 205

Gly Gln Thr Ile His Tyr Asp Glu Val Met Lys Gln Asp Gly His Val
    210                 215                 220

Trp Val Gly Tyr Thr Gly Asn Ser Gly Gln Arg Ile Tyr Leu Pro Val
225                 230                 235                 240

Arg Thr Trp Asn Lys Ser Thr Asn Thr Leu Gly Val Leu Trp Gly Thr
                245                 250                 255

Ile Lys Glu Leu Ala Ala Thr His Glu His Ser Ala Gln Trp Leu Asn
            260                 265                 270

Asn Tyr Lys Lys Gly Tyr Gly Tyr Gly Pro Tyr Pro Leu Gly Ile Asn
        275                 280                 285

Gly Gly Met His Tyr Gly Val Asp Phe Phe Met Asn Ile Gly Thr Pro
    290                 295                 300

Val Lys Ala Ile Ser Ser Gly Lys Ile Val Glu Ala Gly Trp Ser Asn
305                 310                 315                 320

Tyr Gly Gly Gly Asn Gln Ile Gly Leu Ile Glu Asn Asp Gly Val His
                325                 330                 335

Arg Gln Trp Tyr Met His Leu Ser Lys Tyr Asn Val Lys Val Gly Asp
            340                 345                 350

Tyr Val Lys Ala Gly Gln Ile Ile Gly Trp Ser Gly Ser Thr Gly Tyr
        355                 360                 365

Ser Thr Ala Pro His Leu His Phe Gln Arg Met Val Asn Ser Phe Ser
    370                 375                 380

Asn Ser Thr Ala Gln Asp Pro Met Pro Phe Leu Lys Ser Ala Gly Tyr
385                 390                 395                 400

Gly Lys Ala Gly Gly Thr Val Thr Pro Thr Pro Asn Thr Gly Trp Lys
                405                 410                 415

Thr Asn Lys Tyr Gly Thr Leu Tyr Lys Ser Glu Ser Ala Ser Phe Thr
            420                 425                 430

Pro Asn Thr Asp Ile Ile Thr Arg Thr Gly Pro Phe Arg Ser Met
        435                 440                 445

Pro Gln Ser Gly Val Leu Lys Ala Gly Gln Thr Ile His Tyr Asp Glu
    450                 455                 460

Val Met Lys Gln Asp Gly His Val Trp Val Gly Tyr Thr Gly Asn Ser
465                 470                 475                 480

Gly Gln Arg Ile Tyr Leu Pro Val Arg Thr Trp Asn Lys Ser Thr Asn
                485                 490                 495

Thr Leu Gly Val Leu Trp Gly Thr Ile Lys
            500                 505
```

<210> SEQ ID NO 95

<211> LENGTH: 1143
<212> TYPE: DNA
<213> ORGANISM: artificial
<220> FEATURE:
<223> OTHER INFORMATION: artificial construct

<400> SEQUENCE: 95

| | | | | | |
|---|---|---|---|---|---|
| atgagaggat | cgcatcacca | tcaccatcac | ggatccatga | gtaaaggaga | agaactttc 60 |
| actggagttg | tcccaattct | tgttgaatta | gatggtgatg | ttaatgggca | caaattttct 120 |
| gtcagtggag | agggtgaagg | tgatgcaaca | tacggaaaac | ttacccttaa | atttatttgc 180 |
| actactggaa | aactacctgt | tccatggcca | acacttgtca | ctactttcgc | gtatggtctt 240 |
| caatgctttg | cgagataccc | agatcatatg | aaacggcatg | acttttcaa | gagtgccatg 300 |
| cccgaaggtt | atgtacagga | agaactata | ttttcaaag | atgacgggaa | ctacaagaca 360 |
| cgtgctgaag | tcaagtttga | aggtgatacc | cttgttaata | gaatcgagtt | aaaaggtatt 420 |
| gattttaaag | aagatggaaa | cattcttgga | cacaaattgg | aatacaacta | taactcacac 480 |
| aatgtataca | tcatggcaga | caaacaaaag | aatggaatca | aagttaactt | caaaattaga 540 |
| cacaacattg | aagatggaag | cgttcaacta | gcagaccatt | atcaacaaaa | tactccaatt 600 |
| ggcgatggcc | ctgtcctttt | accagacaac | cattacctgt | ccacacaatc | tgcccttcg 660 |
| aaagatccca | acgaaaagag | agaccacatg | gtccttcttg | agtttgtaac | agctgctggg 720 |
| attacacatg | gcatggatga | actatacaaa | gagctcggtg | aaagctaga | agtaagcaaa 780 |
| gcagcaacta | tcaaacaatc | tgacgttaag | caagaagtta | aaaagcaaga | agcaaaacaa 840 |
| attgtgaaag | caacgattg | gaaacagaat | aaagatggca | tttggtataa | agctgaacat 900 |
| gcttcgttca | cagtgacagc | accagaggga | attatcacaa | gatacaaagg | tccttggact 960 |
| ggtcacccac | aagctggtgt | attacaaaaa | ggtcaaacga | ttaaatatga | tgaggttcaa 1020 |
| aaatttgacg | gtcatgtttg | ggtatcgtgg | gaaacgtttg | agggcgaaac | tgtatacatg 1080 |
| ccggtacgca | catgggacgc | taaaactggt | aaagttggta | agttgtgggg | cgaaattaaa 1140 |
| taa | | | | | 1143 |

<210> SEQ ID NO 96
<211> LENGTH: 380
<212> TYPE: PRT
<213> ORGANISM: artificial
<220> FEATURE:
<223> OTHER INFORMATION: artificial construct

<400> SEQUENCE: 96

Met Arg Gly Ser His His His His His His Gly Ser Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Phe Ala Tyr Gly Leu
65                  70                  75                  80

Gln Cys Phe Ala Arg Tyr Pro Asp His Met Lys Arg His Asp Phe Phe
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
            115                 120                 125

Asp Thr Leu Val Asn Arg Ile Glu Leu Lys Gly Ile Asp Phe Lys Glu
130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Ser Lys Asp Pro Asn
    210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
        275                 280                 285

Gln Asn Lys Asp Gly Ile Trp Tyr Lys Ala Glu His Ala Ser Phe Thr
    290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

Asp Glu Val Gln Lys Phe Asp Gly His Val Trp Val Ser Trp Glu Thr
            340                 345                 350

Phe Glu Gly Glu Thr Val Tyr Met Pro Val Arg Thr Trp Asp Ala Lys
        355                 360                 365

Thr Gly Lys Val Gly Lys Leu Trp Gly Glu Ile Lys
    370                 375                 380

<210> SEQ ID NO 97
<211> LENGTH: 516
<212> TYPE: DNA
<213> ORGANISM: Staphylococcus bacteriophage phi 11

<400> SEQUENCE: 97

```
atgcaagcaa aattaactaa aaatgagttt atagagtggt tgaaaacttc tgagggaaaa      60
caattcaatg tggacttatg gtatggattt caatgctttg attatgccaa tgctggttgg     120
aaagttttgt ttggattact tctaaaaggt ttaggtgcaa agatattcc gttcgctaac      180 aacttcgacg gattagctac tgtataccaa aatacaccgg acttcttagc acaacctggc     240
gacatggtgg tattcggtag caactacggt gctggatatg gtcacgttgc atgggtaatt     300
gaagcaactt tagattacat cattgtatat gagcagaatt ggctaggcgg tggctggact     360
gacggaatcg aacaacccgg ctggggttgg gaaaaagtta caagacgaca acatgcttat     420
gatttcccta tgtggtttat ccgtccgaat tttaaaagtg agacagcgcc acgatcagtt     480
caatctccta cacaagcacc taaaaaagaa acagct                               516
```

<210> SEQ ID NO 98

<211> LENGTH: 158
<212> TYPE: PRT
<213> ORGANISM: Staphylococcus bacteriophage phi 11

<400> SEQUENCE: 98

Met Ser Ile Ile Met Glu Val Ala Thr Met Gln Ala Lys Leu Thr Lys
1               5                   10                  15
Asn Glu Phe Ile Glu Trp Leu Lys Thr Ser Glu Gly Lys Gln Phe Asn
            20                  25                  30
Val Asp Leu Trp Tyr Gly Phe Gln Cys Phe Asp Tyr Ala Asn Ala Gly
        35                  40                  45
Trp Lys Val Leu Phe Gly Leu Leu Lys Gly Leu Gly Ala Lys Asp
    50                  55                  60
Ile Pro Phe Ala Asn Asn Phe Asp Gly Leu Ala Thr Val Tyr Gln Asn
65                  70                  75                  80
Thr Pro Asp Phe Leu Ala Gln Pro Gly Asp Met Val Val Phe Gly Ser
                85                  90                  95
Asn Tyr Gly Ala Gly Tyr Gly His Val Ala Trp Val Ile Glu Ala Thr
            100                 105                 110
Leu Asp Tyr Ile Ile Val Tyr Glu Gln Asn Trp Leu Gly Gly Gly Trp
        115                 120                 125
Thr Asp Gly Ile Glu Gln Pro Gly Trp Gly Trp Glu Lys Val Thr Arg
    130                 135                 140
Arg Gln His Ala Tyr Asp Phe Pro Met Trp Phe Ile Arg Pro
145                 150                 155

<210> SEQ ID NO 99
<211> LENGTH: 642
<212> TYPE: DNA
<213> ORGANISM: Staphylococcus bacteriophage phi 11

<400> SEQUENCE: 99
aagccacaac ctaaagcagt agaacttaaa atcatcaaag atgtggttaa aggttatgac      60
ctacctaagc gtggtagtaa ccctaaaggt atagttatac acaacgacgc agggagcaaa     120
ggggcgactg ctgaagcata tcgtaacgga ttagtaaatg cacctttatc aagattagaa     180
gcgggcattg cgcatagtta cgtatcaggc aacacagttt ggcaagcctt agatgaatca     240
caagtaggtt ggcataccgc taatcaaata ggtaataaat attattacgg tattgaagta     300
tgtcaatcaa tgggcgcaga taacgcgaca ttcttaaaaa atgaacaggc aactttccaa     360
gaatgcgcta gattgttgaa aaaatgggga ttaccagcaa acagaaatac aatcagattg     420
cacaatgaat ttacttcaac atcatgccct catagaagtt cggttttaca cactggtttt     480
gacccagtaa ctcgcggtct attgccagaa gacaagcgt tgcaacttaa agactacttt     540
atcaagcaga ttagggcgta catggatggt aaaataccgg ttgccactgt ctctaatgag     600
tcaagcgctt caagtaatac agttaaacca gttgcaagtg ca                        642

<210> SEQ ID NO 100
<211> LENGTH: 163
<212> TYPE: PRT
<213> ORGANISM: Staphylococcus bacteriophage phi 11

<400> SEQUENCE: 100

Asn Pro Lys Gly Ile Val Ile His Asn Asp Ala Gly Ser Lys Gly Ala
1               5                   10                  15
Thr Ala Glu Ala Tyr Arg Asn Gly Leu Val Asn Ala Pro Leu Ser Arg
            20                  25                  30

```
Leu Glu Ala Gly Ile Ala His Ser Tyr Val Ser Gly Asn Thr Val Trp
            35                  40                  45

Gln Ala Leu Asp Glu Ser Gln Val Gly Trp His Thr Ala Asn Gln Ile
 50                  55                  60

Gly Asn Lys Tyr Tyr Gly Ile Glu Val Cys Gln Ser Met Gly Ala
 65                  70                  75                  80

Asp Asn Ala Thr Phe Leu Lys Asn Glu Gln Ala Thr Phe Gln Glu Cys
                    85                  90                  95

Ala Arg Leu Leu Lys Lys Trp Gly Leu Pro Ala Asn Arg Asn Thr Ile
                100                 105                 110

Arg Leu His Asn Glu Phe Thr Ser Thr Ser Cys Pro His Arg Ser Ser
            115                 120                 125

Val Leu His Thr Gly Phe Asp Pro Val Thr Arg Gly Leu Leu Pro Glu
        130                 135                 140

Asp Lys Arg Leu Gln Leu Lys Asp Tyr Phe Ile Lys Gln Ile Arg Ala
145                 150                 155                 160

Tyr Met Asp

<210> SEQ ID NO 101
<211> LENGTH: 462
<212> TYPE: PRT
<213> ORGANISM: Artificial Sequence
<220> FEATURE:
<223> OTHER INFORMATION: Synthetic construct

<400> SEQUENCE: 101

Met Ala Ala Thr His Glu His Ser Ala Gln Trp Leu Asn Asn Tyr Lys
 1                   5                  10                  15

Lys Gly Tyr Gly Tyr Gly Pro Tyr Pro Leu Gly Ile Asn Gly Gly Met
                20                  25                  30

His Tyr Gly Val Asp Phe Phe Met Asn Ile Gly Thr Pro Val Lys Ala
            35                  40                  45

Ile Ser Ser Gly Lys Ile Val Glu Ala Gly Trp Ser Asn Tyr Gly Gly
 50                  55                  60

Gly Asn Gln Ile Gly Leu Ile Glu Asn Asp Gly Val His Arg Gln Trp
 65                  70                  75                  80

Tyr Met His Leu Ser Lys Tyr Asn Val Lys Val Gly Asp Tyr Val Lys
                    85                  90                  95

Ala Gly Gln Ile Ile Gly Trp Ser Gly Ser Thr Gly Tyr Ser Thr Ala
                100                 105                 110

Pro His Leu His Phe Gln Arg Met Val Asn Ser Phe Ser Asn Ser Thr
            115                 120                 125

Ala Gln Asp Pro Met Pro Phe Leu Lys Ser Ala Gly Tyr Gly Lys Ala
        130                 135                 140

Gly Gly Thr Val Thr Pro Thr Pro Asn Thr Gly Leu Lys His Ile Tyr
145                 150                 155                 160

Ser Asn His Ile Lys Gly Asn Lys Ile Thr Ala Pro Lys Pro Ser Ile
                    165                 170                 175

Gln Gly Val Val Ile His Asn Asp Tyr Gly Ser Met Thr Pro Ser Gln
                180                 185                 190

Tyr Leu Pro Trp Leu Tyr Ala Arg Glu Asn Asn Gly Thr His Val Asn
            195                 200                 205

Gly Trp Ala Ser Val Tyr Ala Asn Arg Asn Glu Val Leu Trp Tyr His
        210                 215                 220
```

-continued

```
Pro Thr Asp Tyr Val Glu Trp His Cys Gly Asn Gln Trp Ala Asn Ala
225                 230                 235                 240

Asn Leu Ile Gly Phe Glu Val Cys Glu Ser Tyr Pro Gly Arg Ile Ser
                245                 250                 255

Asp Lys Leu Phe Leu Glu Asn Glu Glu Ala Thr Leu Lys Val Ala Ala
                260                 265                 270

Asp Val Met Lys Ser Tyr Gly Leu Pro Val Asn Arg Asn Thr Val Arg
        275                 280                 285

Leu His Asn Glu Phe Phe Gly Thr Ser Cys Pro His Arg Ser Trp Asp
        290                 295                 300

Leu His Val Gly Lys Gly Glu Pro Tyr Thr Thr Thr Asn Ile Asn Lys
305                 310                 315                 320

Met Lys Asp Tyr Phe Ile Lys Arg Ile Lys His Tyr Tyr Asp Gly Gly
                325                 330                 335

Lys Leu Glu Val Ser Lys Ala Ala Thr Ile Lys Gln Ser Asp Val Lys
                340                 345                 350

Gln Glu Val Lys Lys Gln Glu Ala Lys Gln Ile Val Lys Ala Thr Asp
                355                 360                 365

Trp Lys Gln Asn Lys Asp Gly Ile Trp Tyr Lys Ala Glu His Ala Ser
        370                 375                 380

Phe Thr Val Thr Ala Pro Glu Gly Ile Ile Thr Arg Tyr Lys Gly Pro
385                 390                 395                 400

Trp Thr Gly His Pro Gln Ala Gly Val Leu Gln Lys Gly Gln Thr Ile
                405                 410                 415

Lys Tyr Asp Glu Val Gln Lys Phe Asp Gly His Val Trp Val Ser Trp
                420                 425                 430

Glu Thr Phe Glu Gly Glu Thr Val Tyr Met Pro Val Arg Thr Trp Asp
        435                 440                 445

Ala Lys Thr Gly Lys Val Gly Lys Leu Trp Gly Glu Ile Lys
        450                 455                 460
```